(12) United States Patent
Kohli et al.

(10) Patent No.: US 10,982,286 B2
(45) Date of Patent: Apr. 20, 2021

(54) ALGORITHMIC APPROACH FOR DETERMINING THE PLASMA GENOME ABNORMALITY PGA AND THE URINE GENOME ABNORMALITY UGA SCORES BASED ON CELL FREE CFDNA COPY NUMBER VARIATIONS IN PLASMA AND URINE

(71) Applicants: Mayo Foundation for Medical Education and Research, a charitable corporation of Minnesota, Rochester, MN (US); The Medical College of Wisconsin, Inc., Milwaukee, WI (US); UWM Research Foundation, Inc., Milwaukee, WI (US)

(72) Inventors: Manish Kohli, Rochester, MN (US); Liang Wang, Hartland, WI (US); Chiang-Ching Huang, Brookfield, WI (US)

(73) Assignees: Mayo Foundation for Medical Education and Research, Rochester, MN (US); The Medical College of Wisconsin, Inc., Milwaukee, WI (US); UWM Research Foundation, Inc., Milwaukee, WI (US)

( * ) Notice: Subject to any disclaimer, the term of this patent is extended or adjusted under 35 U.S.C. 154(b) by 939 days.

(21) Appl. No.: 15/411,772

(22) Filed: Jan. 20, 2017

(65) Prior Publication Data
US 2017/0211153 A1 Jul. 27, 2017

Related U.S. Application Data

(60) Provisional application No. 62/286,114, filed on Jan. 22, 2016.

(51) Int. Cl.
  *C12Q 1/6886* (2018.01)
  *A61K 31/337* (2006.01)
  *G16H 50/20* (2018.01)

(52) U.S. Cl.
  CPC ......... *C12Q 1/6886* (2013.01); *A61K 31/337* (2013.01); *G16H 50/20* (2018.01); *C12Q 2600/106* (2013.01); *C12Q 2600/156* (2013.01); *C12Q 2600/158* (2013.01)

(58) Field of Classification Search
  None
  See application file for complete search history.

(56) References Cited

U.S. PATENT DOCUMENTS

| 4,683,195 A | 7/1987 | Mullis et al. ............... 435/6.11 |
| 4,683,202 A | 7/1987 | Mullis ....................... 435/91.2 |
| 2008/0243398 A1 | 10/2008 | Rabinowitz et al. ......... 702/20 |
| 2011/0039724 A1 | 2/2011 | Lo et al. ...................... 506/9 |
| 2011/0201507 A1 | 8/2011 | Rava et al. ................... 506/7 |
| 2011/0230358 A1 | 9/2011 | Rava .......................... 506/7 |

FOREIGN PATENT DOCUMENTS

| EP | 2774997 | 9/2014 |
| WO | WO 2011041485 | 4/2011 |
| WO | WO 2011051283 | 5/2011 |
| WO | WO 2012115885 | 8/2012 |
| WO | WO 2013086352 | 6/2013 |
| WO | WO 2013159035 | 10/2013 |
| WO | WO 2014014497 | 1/2014 |
| WO | WO 2014151117 | 9/2014 |

OTHER PUBLICATIONS

Antonarakis, et al., "Ar-V7 and Resistance to Enzalutamide and Abiraterone in Prostate Cancer." *New England Journal of Medicine*, 371(11):1028-1038 (2014).
Arora, et al., "Glucocorticoid Receptor Confers Resistance to Antiandrogens by Bypassing Androgen Receptor Blockade." *Cell*, 155(6):1309-1322 (2013).
Attard, et al., "Selective Inhibition of Cyp17 with Abiraterone Acetate Is Highly Active in the Treatment of Castration-Resistant Prostate Cancer." *Journal of clinical oncology : official journal of the American Society of Clinical Oncology*, 27(23):3742-3748 (2009).
Bin Hafeez, et al., "Targeted Knockdown of Notch1 Inhibits Invasion of Human Prostate Cancer Cells Concomitant with Inhibition of Matrix Metalloproteinase-9 and Urokinase Plasminogen Activator." *Clin Cancer Res*, 15(2):452-459 (2009).
Botezatu, et al., "Genetic Analysis of DNA Excreted in Urine: A New Approach for Detecting Specific Genomic DNA Sequences from Cells Dying in an Organism." *Clin Chem*, 46(8 Pt 1):1078-1084 (2000).
Casadio, et al., "Urine Cell-Free DNA Integrity as a Marker for Early Prostate Cancer Diagnosis: A Pilot Study." *BioMed Research International*, vol. 2013, Article ID 270457 (2013).
Chan, et al., "Cancer Genome Scanning in Plasma: Detection of Tumor-Associated Copy Number Aberrations, Single-Nucleotide Variants, and Tumoral Heterogeneity by Massively Parallel Sequencing." *Clinical chemistry*, 59(1):211-224 (2013).
Choi, et al., "Procyanidin B3, an Inhibitor of Histone Acetyltransferase, Enhances the Action of Antagonist for Prostate Cancer Cells Via Inhibition of P300-Dependent Acetylation of Androgen Receptor." *Biochem J*, 433(1):235-244 (2011).

(Continued)

*Primary Examiner* — G Steven Vanni
(74) *Attorney, Agent, or Firm* — Medlen & Carroll, LLP

(57) ABSTRACT

The present invention relates to methods of using cell-free DNA analysis for guiding treatment of advanced prostate cancer. In particular, liquid biopsies are collected from urine and/or plasma of patients for measuring copy number variation in cell-free DNA associated with metastatic prostate cancer. In particular, urine genomic abnormality (UGA) and plasma genomic abnormality (PGA) values are contemplated for use in predicting treatment responses in advanced prostate cancer patients and for use in making decisions related to androgen deprivation therapy (ADT) treatment outcomes in hormone sensitive stage and for starting or changing chemotherapy treatments in castrate resistant advanced cancer stage.

10 Claims, 19 Drawing Sheets
(19 of 19 Drawing Sheet(s) Filed in Color)
Specification includes a Sequence Listing.

(56) References Cited

OTHER PUBLICATIONS

Codony-Servat, et al., "Nuclear Factor-Kappa B and Interleukin-6 Related Docetaxel Resistance in Castration-Resistant Prostate Cancer." *Prostate*, 73(5):512-521 (2013).
Cree, "Liquid Biopsy for Cancer Patients: Principles and Practice." *Pathogenesis*, 2(1):1-4 (2015).
Crowley, et al., "Liquid Biopsy: Monitoring Cancer-Genetics in the Blood." *Nat Rev Clin Oncol*, 10(8):472-484 (2013).
Dawson, et al., "Analysis of Circulating Tumor DNA to Monitor Metastatic Breast Cancer." *N Engl J Med*, 368(13):1199-1209 (2013).
De Bono, et al., "Prednisone Plus Cabazitaxel or Mitoxantrone for Metastatic Castration-Resistant Prostate Cancer Progressing after Docetaxel Treatment: A Randomised Open-Label Trial." *Lancet*, 376(9747):1147-1154 (2010).
De Bono, et al., "Abiraterone and Increased Survival in Metastatic Prostate Cancer." *N Engl J Med*, 364(21):1995-2005 (2011).
De Mattos-Arruda, et al., "Circulating Tumour Cells and Cell-Free DNA as Tools for Managing Breast Cancer." *Nat Rev Clin Oncol*, 10(7):377-389 (2013).
Delgado, et al., "Characterization of Cell-Free Circulating DNA in Plasma in Patients with Prostate Cancer." *Tumour Biol*, 34(2):983-986 (2013).
Denis, et al., "Maximal Androgen Blockade: Final Analysis of Eortc Phase Iii Trial 30853. Eortc Genito-Urinary Tract Cancer Cooperative Group and the Eortc Data Center." *Eur Urol*, 33(2):144-151 (1998).
Diamond, et al., "Detection of an NRAS Mutation in Erdheim-Chester Disease." *Blood*, 122(6):1089-1091 (2013).
Diaz and Bardelli, "Liquid Biopsies: Genotyping Circulating Tumor DNA." *Journal of Clinical Oncology*, 32(6):579-586 (2014).
Diskin, et al., "Adjustment of Genomic Waves in Signal Intensities from Whole-Genome Snp Genotyping Platforms." *Nucleic Acids Research*, 36(19):e126-e126 (2008).
Eisenberger, et al., "Bilateral Orchiectomy with or without Flutamide for Metastatic Prostate Cancer." *New England Journal of Medicine*, 339(15):1036-1042 (1998).
Ellen, et al., "NDRG1, a Growth and Cancer Related Gene: Regulation of Gene Expression and Function in Normal and Disease States." *Carcinogenesis*, 29(1):2-8 (2008).
Emile, et al., "Recurrent Ras and Pik3ca Mutations in Erdheim-Chester Disease." *Blood*, 124(19):3016-3019 (2014).
Esposito, et al., "Monitoring Tumor-Derived Cell-Free DNA in Patients with Solid Tumors: Clinical Perspectives and Research Opportunities." *Cancer Treat Rev*, 40(5):648-655 (2014).
Farris and Trimarchi, "Plasma-Seq: A Novel Strategy for Metastatic Prostate Cancer Analysis." *Genome Medicine*, 5(4):35 (2013).
Feng, et al., "Plasma Cell-Free DNA and Its DNA Integrity as Biomarker to Distinguish Prostate Cancer from Benign Prostatic Hyperplasia in Patients with Increased Serum Prostate-Specific Antigen." *Int Urol Nephrol*, 45(4):1023-1028 (2013).
Fizazi, et al., "Denosumab Versus Zoledronic Acid for Treatment of Bone Metastases in Men with Castration-Resistant Prostate Cancer: A Randomised, Double-Blind Study." *Lancet*, 377(9768):813-822 (2011).
Heemers, et al., "Androgen Deprivation Increases P300 Expression in Prostate Cancer Cells." *Cancer Res*, 67(7):3422-3430 (2007).
Heitzer, et al., "Establishment of Tumor-Specific Copy Number Alterations from Plasma DNA of Patients with Cancer." *Int J Cancer*, 133(2):346-356 (2013a).
Heitzer, et al., "Tumor-Associated Copy Number Changes in the Circulation of Patients with Prostate Cancer Identified through Whole-Genome Sequencing." *Genome Med*, 5(4):30 (2013b).
Heitzer, et al., "Circulating Tumor DNA as a Liquid Biopsy for Cancer." *Clin Chem*, 61(1):000-000 (2015) Epub 2014.
Heitzer, et al., "Circulating Tumor DNA as a Liquid Biopsy for Cancer." *Clin Chem*, 61(1):112-123 (2015).
Hessels and Schalken, "Urinary Biomarkers for Prostate Cancer: A Review." *Asian J Androl*, 15(3):333-339 (2013).
Hsieh, et al., "Myc and Metabolism on the Path to Cancer." *Semin Cell Dev Biol*, 43:11-21 (2015).
Huang, et al., "Exosomal Mir-1290 and Mir-375 as Prognostic Markers in Castration-Resistant Prostate Cancer." *Eur Urol*, 67(1):33-41 (2015).
Huggins and Hodges "Studies on Prostatic Cancer: I. The Effect of Castration, of Estrogen and of Androgen Injection on Serum Phosphatases in Metastatic Carcinoma of the Prostate. 1941." *J Urol*, 168(1):9-12 (2002).
Ignatiadis and Dawson, "Circulating Tumor Cells and Circulating Tumor DNA for Precision Medicine: Dream or Reality?". *Annals of Oncology*, 25(12):2304-2313 (2014).
Kantoff, et al., "Sipuleucel-T Immunotherapy for Castration-Resistant Prostate Cancer." *N Engl J Med*, 363(5):411-422 (2010).
Kato and Janku, "Cell-Free DNA as a Novel Marker in Cancer Therapy." *Biomarkers in medicine*, 9(7):703-712 (2015).
Kim, et al., "Integrative Analysis of Genomic Aberrations Associated with Prostate Cancer Progression." *Cancer Res*, 67(17):8229-8239 (2007).
KohliTindall "New Developments in the Medical Management of Prostate Cancer." *Mayo Clinic Proceedings*, 85(1):77-86 (2010).
Koivisto, et al., "Androgen Receptor Gene Amplification: A Possible Molecular Mechanism for Androgen Deprivation Therapy Failure in Prostate Cancer." *Cancer Res*, 57(2):314-319 (1997).
Kwee, et al., "Measurement of Circulating Cell-Free DNA in Relation to 18f-Fluorocholine Pet/Ct Imaging in Chemotherapy-Treated Advanced Prostate Cancer." *Clin Transl Sci*, 5(1):65-70 (2012).
Leary, et al., "Detection of Chromosomal Alterations in the Circulation of Cancer Patients with Whole-Genome Sequencing." *Science translational medicine*, 4(162):162ra154-162ra154 (2012).
Lewinshtein, et al., "Genomic Predictors of Prostate Cancer Therapy Outcomes." *Expert Rev Mot Diagn*, 10(5):619-636 (2010).
Lichtenstein, et al., "Circulating Nucleic Acids and Apoptosis." *Ann N Y Acad Sci*, 945:239-249 (2001).
Limonta and Manea, "Gonadotropin-Releasing Hormone Receptors as Molecular Therapeutic Targets in Prostate Cancer: Current Options and Emerging Strategies." *Cancer treatment reviews*, 39(6):647-663 (2013).
Liu, et al., "Comprehensive Assessment of DNA Copy Number Alterations in Human Prostate Cancers Using Affymetrix 100k Snp Mapping Array." *Genes, Chromosomes and Cancer*, 45(11):1018-1032 (2006).
Loeb, et al., "Active Surveillance for Prostate Cancer: A Systematic Review of Clinicopathologic Variables and Biomarkers for Risk Stratification." *Eur Urol*, 67(4):619-626 (2015).
Loilome, et al., "Prkarla Is Overexpressed and Represents a Possible Therapeutic Target in Human Cholangiocarcinoma." *Int j Cancer*, 129(1):34-44 (2011).
Ma, et al., "Diagnostic and Prognostic Scoring System for Prostate Cancer Using Urine and Plasma Biomarkers." *Genet Test Mol Biomarkers*, 18(3):156-163 (2014).
Marin-Aguilera, et al., "Epithelial-to-Mesenchymal Transition Mediates Docetaxel Resistance and High Risk of Relapse in Prostate Cancer." *Mol Cancer Ther*, 13(5):1270-1284 (2014).
"Maximum Androgen Blockade in Advanced Prostate Cancer: An Overview of the Randomised Trials." Prostate Cancer Trialists Collaborative Group. *Lancet*, 355(9214):1491-1498 abstract only (2000).
McKiernan, et al., "Exosome Diagnostics Announces Positive Results from Large Clinical Validation Study of Prostate Cancer Liquid Biopsy." www.exosomedx.com/news-events/press-releases/exosome-diagnostics-announce-s-positive-results-large-clinical-validation. May 17, 2015.
Merkle and Hoffmann, "Roles of cAMP and cAMP-Dependent Protein Kinase in the Progression of Prostate Cancer: Cross-Talk with the Androgen Receptor." *Cellular signalling*, 23(3):507-515 (2011).
Murtaza, et al., "Non-Invasive Analysis of Acquired Resistance to Cancer Therapy by Sequencing of Plasma DNA." *Nature*, 497(7447):108 (2013).

(56) References Cited

OTHER PUBLICATIONS

Nakata, et al., "Emerging Role for Leucine-Rich Repeat-Containing G-Protein-Coupled Receptors Lgr5 and Lgr4 in Cancer Stem Cells." *Cancer Management and Research*, 6:171-180 (2014).
Narayan, et al., "Ultrasensitive Measurement of Hotspot Mutations in Tumor DNA in Blood Using Error-Suppressed Multiplexed Deep Sequencing." *Cancer Res*, 72(14):3492-3498 (2012).
Nazareth and Weigel "Activation of the Human Androgen Receptor through a Protein Kinase a Signaling Pathway." *J Biol Chem*, 271(33):19900-19907 (1996).
Ni, et al., "Reproducible Copy No. Variation Patterns among Single Circulating Tumor Cells of Lung Cancer Patients." *Proc Natl Acad Sci U S A*, 110(52):21083-21088 (2013).
O'Neill, et al., "Characterisation and Manipulation of Docetaxel Resistant Prostate Cancer Cell Lines." *Molecular cancer*, 10(1):126 (2011).
Petrylak, et al., "Docetaxel and Estramustine Compared with Mitoxantrone and Prednisone for Advanced Refractory Prostate Cancer." *New England Journal of Medicine*, 351(15):1513-1520 (2004).
Phin, et al., "Genomic Rearrangements of Pten in Prostate Cancer." *Front Oncol*, 3:240 (2013).
Porkka, et al., "Rad21 and Kiaa0196 at 8q24 Are Amplified and Overexpressed in Prostate Cancer." *Genes Chromosomes Cancer*, 39(1):1-10 (2004).
Ryan, et al., "Abiraterone in Metastatic Prostate Cancer without Previous Chemotherapy." *New England Journal of Medicine*, 368(2):138-148 (2013).
Salvi, et al., "Urine Cell-Free DNA Integrity Analysis for Early Detection of Prostate Cancer Patients." *Disease Markers*, 2015:574120 (2015).
Saramäki, et al., "Genetic Aberrations in Prostate Cancer by Microarray Analysis." *International Journal of Cancer*, 119(6):1322-1329 (2006).
Sarwar, et al., "Protein Kinase a (PKA) Pathway Is Functionally Linked to Androgen Receptor (AR) in the Progression of Prostate Cancer." *Urol Oncol*, 32(1):25 e21-12 (2014).
Scher, et al., "Increased Survival with Enzalutamide in Prostate Cancer after Chemotherapy." *N Engl J Med*, 367(13):1187-1197 (2012).
Schutz, et al., "Chromosomal Instability in Cell-Free DNA Is a Serum Biomarker for Prostate Cancer." *Clin Chem*, 61(1):239-248 (2015) Epub Oct 27, 2014.
Schutz, et al., "Chromosomal Instability in Cell-Free DNA Is a Serum Biomarker for Prostate Cancer." *Clin Chem*, 61(1):239-248 (2015) Supplemental Data (clinchem.2014.226571), Epub Oct 27, 2014.
Schwarzenbach, et al., "Cell-Free Tumor DNA in Blood Plasma as a Marker for Circulating Tumor Cells in Prostate Cancer." *Clin Cancer Res*, 15(3):1032-1038 (2009).
Shaw, et al., "Genomic Analysis of Circulating Cell-Free DNA Infers Breast Cancer Dormancy." *Genome Res*, 22(2):220-231 (2012).
Siegel, et al., "Cancer Statistics, 2015." *CA Cancer J Clin*, 65(1):5-29 (2015).
Singh, et al., "Serum Microrna Expression Patterns That Predict Early Treatment Failure in Prostate Cancer Patients." *Oncotarget*, 5(3):824-840 (2014).
Snedecor, et al., "Denosumab Versus Zoledronic Acid for Treatment of Bone Metastases in Men with Castration-Resistant Prostate Cancer: A Cost-Effectiveness Analysis." *J Med Econ*, 16(1):19-29 (2013).
Sweeney, et al., "Chemohormonal Therapy in Metastatic Hormone-Sensitive Prostate Cancer." *N Engl J Med*, 373(8):737-746 (2015).
Tannock, et al., "Docetaxel Plus Prednisone or Mitoxantrone Plus Prednisone for Advanced Prostate Cancer." *New England Journal of Medicine*, 351(15):1502-1512 (2004).
Taplin and Balk, "Androgen Receptor: A Key Molecule in the Progression of Prostate Cancer to Hormone Independence." *Journal of cellular biochemistry*, 91(3):483-190 (2004).
Tindall, et al., "Comprehensive Analysis of the Cytokine-Rich Chromosome 5q31.1 Region Suggests a Role for I1-4 Gene Variants in Prostate Cancer Risk." *Carcinogenesis*, 31(10):1748-1754 (2010).
Tuupanen, et al., "The Common Colorectal Cancer Predisposition Snp Rs6983267 at Chromosome 8q24 Confers Potential to Enhanced Wnt Signaling." *Nat Genet*, 41(8):885-890 (2009).
Wang, et al., "Down-Regulation of Notch-1 and Jagged-1 Inhibits Prostate Cancer Cell Growth, Migration and Invasion, and Induces Apoptosis Via Inactivation of Akt, Mtor, and Nf-Kappab Signaling Pathways." *J Cell Biochem*, 109(4):726-736 (2010).
Williams, et al., "Recurrent Copy Number Alterations in Prostate Cancer: An in Silico Meta-Analysis of Publicly Available Genomic Data." *Cancer Genetics*, 207(10):474-488 (2014).
Witte, et al., "Genomewide Scan for Prostate Cancer—Aggressiveness Loci." *American Journal of Human Genetics*, 67(1):92-99 (2000).
Xie, et al., "The Expression of Glucocorticoid Receptor Is Negatively Regulated by Active Androgen Receptor Signaling in Prostate Tumors." *Int J Cancer*, 136(4):E27-38 (2014).
Xia, et al., "Plasma Genetic and Genomic Abnormalities Predict Treatment Response and Clinical Outcome in Advanced Prostate Cancer." *Oncotarget*, 6(18):16411-16421 (2015).
Xia, et al., "Copy Number Variations in Urine Cell Free DNA as Biomarkers in Advanced Prostate Cancer." *Oncotarget*, 7(24):35818-35831 (2016).
Yan, et al., "Urinary Nucleic Acid TSPAN13-TO-S100A9 Ratio as a Diagnostic Marker in Prostate Cancer." *Journal of Korean Medical Science*, 30(12):1784-1792 (2015).
Yao, et al., "Evaluation of the TMPRSS2: ERG Fusion for the Detection of Prostate Cancer: A Systematic Review and Meta-Analysis." *Tumor Biology*, 35(3):2157-2166 (2014) online 2013.
Yoshimoto, et al., "PTEN Genomic Deletions That Characterize Aggressive Prostate Cancer Originate Close to Segmental Duplications." *Genes Chromosomes Cancer*, 51(2):149-160 (2012).
Yun, et al., "Comparison of mRNA, Protein, and Urinary Nucleic Acid Levels of S100A8 and S100A9 between Prostate Cancer and BPH." *Annals of surgical oncology*, 22(7):2439-2445 (2015).
Zebisch and Jones, "ZNRF3/RNF43—a Direct Linkage of Extracellular Recognition and E3 Ligase Activity to Modulate Cell Surface Signalling." *Prog Biophys Mol Biol*, 118(3):112-118 (2015).

A: Urine CRPC

B: Plasma CRPC

C: Urine HSPC

D: Plasma HSPC though they may appear as US 10,982,286 B2

SEQUENCE LISTING

```
<160> NUMBER OF SEQ ID NOS: 77

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tcatacgccc ttagctgttg g                                          21

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
cggtcccagc actgggtata                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cggtcccagc actgggtatg                                            20
```

-continued

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
cctctggatg accctgaca                                                19

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
gtgggtgaag ctggtggttc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gtgggtgaag ctggtggtta                                               20

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
atgggaaaca cgcagaag                                                 18

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ctgaacgaag agcgagggg                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
ctgaacgaag agcgagggt                                                19

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ctcagtgttc tcctgcttcg                                                   20

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
acttagtctt ctctataccc agcc                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
acttagtctt ctctataccc agca                                              24

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
gcaaggcatg gggtgggt                                                     18

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
ggcatcagct tctcaacaca cc                                                22

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
ggcatcagct tctcaacaca ca                                                22

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
aaccccaaaa ttagacgca                                                    19

<210> SEQ ID NO 17
<211> LENGTH: 25

-continued

<212> TYPE: DNA
<213> ORGANISM: Artificial Sequence
<220> FEATURE:
<223> OTHER INFORMATION: Synthetic

<400> SEQUENCE: 17
aaaaagatga cagattaaac atact                                       25

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
aaaaagatga cagattaaac atacc                                       25

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
tgcccacatc cctccctac                                              19

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
cagtggctgt cctaccaggg                                             20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
cagtggctgt cctaccagga                                             20

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
ccctcggggc actttctaa                                              19

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23

```
<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tccatcttgc ctcttggccg                                              20

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
ggtgggaaga ggcgtcag                                                18

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
caaatgactc cttctctgag cat                                          23

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
caaatgactc cttctctgag caa                                          23

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
ataaacctag aattgggagc tg                                           22

<210> SEQ ID NO 29
<211> LENGTH: 25
<212> TYPE: DNA
<213> ORGANISM: Artificial Sequence
<220> FEATURE:
<223> OTHER INFORMATION: Synthetic

<400> SEQUENCE: 29
tggcaataat agaaggaaag aatag                                        25

<210> SEQ ID NO 30
<211> LENGTH: 25
<212> TYPE: DNA
<213> ORGANISM: Artificial Sequence
```

(preceding line from previous page: `tccatcttgc ctcttggcca   20`)

<220> FEATURE:
<223> OTHER INFORMATION: Synthetic

<400> SEQUENCE: 30
tggcaataat agaaggaaag aataa                                              25

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
gccatcctga ccaacctga                                                     19

<210> SEQ ID NO 32
<211> LENGTH: 26
<212> TYPE: DNA
<213> ORGANISM: Artificial Sequence
<220> FEATURE:
<223> OTHER INFORMATION: Synthetic

<400> SEQUENCE: 32
tctcttcaac tgaaagacta aaatca                                             26

<210> SEQ ID NO 33
<211> LENGTH: 26
<212> TYPE: DNA
<213> ORGANISM: Artificial Sequence
<220> FEATURE:
<223> OTHER INFORMATION: Synthetic

<400> SEQUENCE: 33
tctcttcaac tgaaagacta aaatcc                                             26

<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
tgcccatcca gtcaacgg                                                      18

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
ctcctcacct gctgccagc                                                     19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
ctcctcacct gctgccaga                                                     19

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
tcccggacac cccttgatg                                          19

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
ccgtagtcat tgtcctccag cat                                     23

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ccgtagtcat tgtcctccag cac                                     23

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
atgttgaggg cagtctttg                                          19

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
ggaggaagag tcttttcatc c                                       21

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
ggaggaagag tcttttcatc a                                       21

<210> SEQ ID NO 43
<211> LENGTH: 25
<212> TYPE: DNA
<213> ORGANISM: Artificial Sequence
<220> FEATURE:
<223> OTHER INFORMATION: Synthetic

<400> SEQUENCE: 43
ttgtatggtg gctgttgtat ttatt                                           25

<210> SEQ ID NO 44
<211> LENGTH: 24
<212> TYPE: DNA
<213> ORGANISM: Artificial Sequence
<220> FEATURE:
<223> OTHER INFORMATION: Synthetic

<400> SEQUENCE: 44
ccatttactc ccataggact agcc                                            24

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
ccatttactc ccataggact agca                                            24

<210> SEQ ID NO 46
<211> LENGTH: 22
<212> TYPE: DNA
<213> ORGANISM: Artificial Sequence
<220> FEATURE:
<223> OTHER INFORMATION: Synthetic

<400> SEQUENCE: 46
tatgaaaagt ccccgataag tt                                              22

<210> SEQ ID NO 47
<211> LENGTH: 23
<212> TYPE: DNA
<213> ORGANISM: Artificial Sequence
<220> FEATURE:
<223> OTHER INFORMATION: Synthetic

<400> SEQUENCE: 47
catggagatg ctactgatgt caa                                             23

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
catggagatg ctactgatgt cag                                             23

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
atgcacaatg taccgctcta cc                                              22

<210> SEQ ID NO 50

```
<211> LENGTH: 23
<212> TYPE: DNA
<213> ORGANISM: Artificial Sequence
<220> FEATURE:
<223> OTHER INFORMATION: Synthetic

<400> SEQUENCE: 50
gcacatggta caaaccaatc agg                                              23

<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51
attccatagc attatgtggt gat                                              23

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
ttccgctttc tcagtgtgct ta                                               22

<210> SEQ ID NO 53
<211> LENGTH: 22
<212> TYPE: DNA
<213> ORGANISM: Artificial Sequence
<220> FEATURE:
<223> OTHER INFORMATION: Synthetic

<400> SEQUENCE: 53
ttccgctttc tcagtgtgct tc                                               22

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
tactgttgcc caccctttgc                                                  20

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
ctaatgcctg ctatgcaata cg                                               22

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
```
ctaatgcctg ctatgcaata ca                                              22

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
ctcccaccac ttagatgccg t                                               21

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
tgcagcgatg catccacaca                                                 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
tgcagcgatg catccacacc                                                 20

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
gcctaactgc ccgagatgc                                                  19

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
ccgagcttag acgcgagagt                                                 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
ccgagcttag acgcgagagg                                                 20

<210> SEQ ID NO 63
<211> LENGTH: 20
<212> TYPE: DNA

```
<213> ORGANISM: Artificial Sequence
<220> FEATURE:
<223> OTHER INFORMATION: Synthetic

<400> SEQUENCE: 63
gggttgtggc tgggagactg                                                   20

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
tggtttgccc actaacaagg tatc                                              24

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
tggtttgccc actaacaagg tata                                              24

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
ggacccagga gaaggcagag                                                   20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
gccagcgagt ttcgtgatca                                                   20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gccagcgagt ttcgtgatca                                                   20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
ccaagggatt caggttcaga                                                   20
```

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
ccctcttatt tctgggcagg                                           20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
ccctcttatt tctgggcaga                                           20

<210> SEQ ID NO 72
<211> LENGTH: 22
<212> TYPE: DNA
<213> ORGANISM: Artificial Sequence
<220> FEATURE:
<223> OTHER INFORMATION: Synthetic

<400> SEQUENCE: 72
actccgtggt ctgctgggtg ct                                        22

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ttgttgtggc cctggcaggg                                           20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
ttgttgtggc cctggcaggt                                           20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cacgctcccg gtacaccctg                                           20

<210> SEQ ID NO 76
<211> LENGTH: 20
<212> TYPE: DNA
<213> ORGANISM: Artificial Sequence
<220> FEATURE:

```
<223> OTHER INFORMATION: Synthetic

<400> SEQUENCE: 76
ccatctcctc ctcccccagc                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
ccatctcctc ctcccccaga                                              20
```

ALGORITHMIC APPROACH FOR DETERMINING THE PLASMA GENOME ABNORMALITY PGA AND THE URINE GENOME ABNORMALITY UGA SCORES BASED ON CELL FREE CFDNA COPY NUMBER VARIATIONS IN PLASMA AND URINE

This invention was made with government support under Grant No. CA157881 and Grant No. R01CA157881 awarded by the National Institutes of Health. The government has certain rights in the invention.

FIELD OF THE INVENTION

The present invention relates to methods of using cell-free DNA analysis for guiding treatment of advanced prostate cancer. In particular, liquid biopsies are collected from urine and/or plasma of patients for measuring copy number variation in cell-free DNA associated with metastatic prostate cancer. In particular, urine genomic abnormality (UGA) and plasma genomic abnormality (PGA) values are contemplated for use in predicting treatment responses in advanced prostate cancer patients and for use in making decisions related to androgen deprivation therapy (ADT) treatment outcomes in hormone sensitive stage and for starting or changing chemotherapy treatments in castrate resistant advanced cancer stage.

BACKGROUND

Androgen deprivation therapy (ADT) has been used to treat advanced prostate cancer since 1941 (Huggins and Hodges, "Studies on prostatic cancer: I. The effect of castration, of estrogen and of androgen injection on serum phosphatases in metastatic carcinoma of the prostate." 1941. J Urol. 2002; 168:9-12). In 2011, more than one-third of the estimated 2.71 million prostate cancer patients in the United States received ADT.

Responses to ADT in the hormone-sensitive prostate cancer (HSPC) lasts from a few months to several years (median 18-30 months). However, there are no known predictive factors for duration of ADT response.

After the emergence of castration-resistant prostate cancer (CRPC), several new systemic anti-cancer therapies with overall survival benefit are currently considered (Kohli and Tindall, "New developments in the medical management of prostate cancer." Mayo Clin Proc. 2010; 85:77-86). A biochemical response to these treatments is often estimated by PSA levels. However, this estimate may be unreliable due to disease heterogeneity.

Therefore, more sensitive and specific assays to monitor prostate cancer treatment responses in patients are needed.

SUMMARY

The present invention relates to methods of using cell-free DNA analysis for guiding treatment of advanced prostate cancer. In particular, liquid biopsies are collected from urine and/or plasma of patients for measuring copy number variation in cell-free DNA associated with metastatic prostate cancer. In particular, urine genomic abnormality (UGA) and plasma genomic abnormality (PGA) values are contemplated for use in predicting treatment responses in advanced prostate cancer patients and for use in making decisions related to androgen deprivation therapy (ADT) treatment outcomes in hormone sensitive stage and for starting or changing chemotherapy treatments in castrate resistant advanced cancer stage.

In one embodiment, the present invention provides a method, comprising: i) isolating a first cell free DNA sample from a prostate cancer patient, e.g. a metastatic stage prostate cancer patient, prior to treatment; ii) sequencing said cell free (cf) DNA from said first sample so as to determine a first copy number variation as compared to a control (e.g. a patient's own DNA); iii) calculating a first cfDNA Plasma Genomic Abnormality (PGA) Score based on said copy number variation; iv) treating said prostate cancer patient, e.g. a metastatic stage prostate cancer patient, with Androgen Deprivation Therapy (ADT); v) isolating a second cell free DNA sample from said prostate cancer patient after said treating of step (iv); vi) sequencing said cell free DNA from said second sample so as to determine a second copy number variation as compared to a control; vii) calculating a second cfDNA Plasma Genomic Abnormality (PGA) Score; viii) comparing said first PGA score with said second PGA score; and ix) administering a chemotherapy composition to said subject when said second cfDNA Plasma Genomic Abnormality (PGA) Score is equal to or greater than said first cfDNA Plasma Genomic Abnormality (PGA) Score. In one embodiment, said second cfDNA Plasma Genomic Abnormality Score is obtained at least two weeks after initiating Androgen Deprivation Therapy. In one embodiment, second cfDNA Plasma Genomic Abnormality Score is obtained at least two months after initiating Androgen Deprivation Therapy. In one embodiment, said control comprises genomic DNA from said patient's lymphocytes.

In one embodiment, the present invention provides a method, comprising: i) isolating a first cell free (cf) DNA sample from a prostate cancer patient, e.g. a metastatic stage prostate cancer patient, prior to treatment; ii) sequencing said cell free DNA from said first sample so as to determine a first copy number variation as compared to a control; iii) calculating a first cfDNA Urine Genomic Abnormality (UGA) Score based on said copy number variation; iv) treating said prostate cancer patient, e.g. a metastatic stage prostate cancer patient, with Androgen Deprivation Therapy (ADT); v) isolating a second cell free DNA sample from said prostate cancer patient after said treating of step (iv); vi) sequencing said cell free DNA from said second sample so as to determine a second copy number variation as compared to a control (e.g. a patient's own DNA); vii) calculating a second cfDNA Urine Genomic Abnormality (UGA) Score; viii) comparing said first UGA score with said second UGA score; and ix) administering a chemotherapy composition to said subject when said second cfDNA Urine Genomic Abnormality (UGA) Score is equal to or greater than said first cfDNA Urine Genomic Abnormality (UGA) Score. In one embodiment, said second cfDNA Urine Genomic Abnormality Score is obtained at least two weeks after initiating Androgen Deprivation Therapy. In one embodiment, said second cfDNA Urine Genomic Abnormality Score is obtained at least two months after initiating Androgen Deprivation Therapy. In one embodiment, said control comprises genomic DNA from said patient's lymphocytes.

In one embodiment, the present invention provides a method, comprising: i) isolating a first cell free (cf) DNA sample from a prostate cancer patient prior to treatment; ii) sequencing said cell free DNA from said first sample so as to determine a first copy number variation as compared to a control; iii) calculating a first cell free DNA Plasma Genomic Abnormality (PGA) Score based on said copy number variation; iv) treating said prostate cancer patient with Androgen Deprivation Therapy (ADT); v) isolating a second cell free DNA sample from said prostate cancer patient after said treating of step (iv); vi) sequencing said cell free DNA from said second sample so as to determine a second copy number variation as compared to a control; vii) calculating a second cell free DNA Plasma Genomic Abnormality (PGA) Score; viii) comparing said first PGA score with said second PGA score; and ix) administering a treatment to said subject when said second cell free DNA Plasma Genomic Abnormality (PGA) Score is equal to or greater than said first cell free DNA Plasma Genomic Abnormality (PGA) Score. In one embodiment, said second cfDNA Plasma Genomic Abnormality Score is obtained at least two weeks after initiating Androgen Deprivation Therapy. In one embodiment, said second cfDNA Plasma Genomic Abnormality Score is obtained at least two months after initiating Androgen Deprivation Therapy. In one embodiment, said control comprises genomic DNA from said patient's lymphocytes. In one embodiment, said patient shows symptoms of Androgen Deprivation Therapy failure after step iv). In one embodiment, said symptoms appear before step v). In one embodiment, said second copy number variation is calculated from a 15-gene panel. In one embodiment, said 15-genes are ZDHHC18, MRPS22, SAMD7, DMTN, ZNF704, SPAG1, SNX31, SAMD12, LOC101928197, KLHDC4, SPG7, CHMPIA, PDRG1, PETN and RB1. In one embodiment, said treatment is a chemotherapy composition. In one embodiment, said treatment is selected from the group consisting of hormonal therapy and radiotherapy.

In one embodiment, the present invention provides a method, comprising: i) isolating a first cell free (cf) DNA sample from a prostate cancer patient prior to treatment; ii) sequencing said cell free DNA from said first sample so as to determine a first copy number variation as compared to a control; iii) calculating a first cell free DNA Urine Genomic Abnormality (UGA) Score based on said copy number variation; iv) treating said prostate cancer patient with Androgen Deprivation Therapy (ADT); v) isolating a second cell free DNA sample from said prostate cancer patient after said treating of step (iv); vi) sequencing said cell free DNA from said second sample so as to determine a second copy number variation as compared to a control; vii) calculating a second cell free DNA Urine Genomic Abnormality (UGA) Score; viii) comparing said first UGA score with said second UGA score; and ix) administering a treatment to said subject when said second cell free DNA Urine Genomic Abnormality (UGA) Score is equal to or greater than said first cell free DNA Urine Genomic Abnormality (UGA) Score. In one embodiment, said second cfDNA Urine Genomic Abnormality Score is obtained at least two weeks after initiating Androgen Deprivation Therapy. In one embodiment, said second cfDNA Urine Genomic Abnormality Score is obtained at least two months after initiating Androgen Deprivation Therapy. In one embodiment, said control comprises genomic DNA from said patient's lymphocytes. In one embodiment, said patient shows symptoms of Androgen Deprivation Therapy failure after step iv). In one embodiment, said symptoms appear before step v). In one embodiment, said treatment is a chemotherapy composition. In one embodiment, said treatment is selected from the group consisting of hormonal therapy and radiotherapy. In one embodiment, said second copy number variation is calculated from a 15-gene panel. In one embodiment, said 15-genes are ZDHHC18, MRPS22, SAMD7, DMTN, ZNF704, SPAG1, SNX31, SAMD12, LOC101928197, KLHDC4, SPG7, CHMPIA, PDRG1, PETN and RB1.

In one embodiment, the present invention provides a method, comprising: i) isolating a cell free (cf) DNA sample and a genomic DNA sample from a prostate cancer patient; ii) sequencing said cell free DNA from said sample so as to determine a copy number variation as compared to sequencing said genomic DNA, wherein said sequenced DNA is a 15-gene panel; iii) calculating a cell free DNA Genomic Abnormality Score based on said copy number variation; iv) administering a treatment to said subject when said cell free DNA Genomic Abnormality Score correlates with an overall survival time prediction of 80 months or less (and preferably 60 months or less, and more preferably 50 months or less, and still more preferably 40 months or less, and particularly where the survival prediction is 20 months or less). In one embodiment, said cfDNA is isolated from a plasma sample for calculating a Plasma Genomic Abnormality (PGA) Score. In one embodiment, said cfDNA is isolated from a urine sample for calculating a Urine Genomic Abnormality (UGA) Score. In one embodiment, said patient is treated with Androgen Deprivation Therapy prior to step i). In one embodiment, said cfDNA sample is obtained at least two weeks after initiating Androgen Deprivation Therapy. In one embodiment, said cfDNA sample is obtained at least two months after initiating Androgen Deprivation Therapy. In one embodiment, said patient shows symptoms of Androgen Deprivation Therapy failure. In one embodiment, said cfDNA sample is obtained after symptoms of Androgen Deprivation Therapy failure. In one embodiment, said treatment is a chemotherapy composition. In one embodiment, said treatment is selected from the group consisting of hormonal therapy and radiotherapy. In one embodiment, said 15-genes are ZDHHC18, MRPS22, SAMD7, DMTN, ZNF704, SPAG1, SNX31, SAMD12, LOC101928197, KLHDC4, SPG7, CHMPIA, PDRG1, PETN and RB1. In one embodiment, said genomic DNA is from said patient's lymphocytes.

In one embodiment, the present invention provides a method, comprising: i) isolating a cell free (cf) DNA sample and a genomic DNA sample from a prostate cancer patient; ii) sequencing said cell free DNA from said sample so as to determine a copy number variation as compared to sequencing said genomic DNA, wherein said sequenced DNA is a 15-gene panel; iii) calculating a Leave-one-out cross-validation (LOOCV) score; iv) correlating said Leave-one-out cross-validation (LOOCV) score with a survival probability; and iv) administering a treatment to said subject when said survival probability is 40 months or less. It is not meant to limit the survival probability to 40 months or less, in fact correlation of a LOOCV Score with a survival probability may be a survival probability greater than 0 months and up to or including 20 months or less, 40 months or less, 60 months or less, up to and including 80 months or less.

BRIEF DESCRIPTION OF THE DRAWINGS

The patent application file contains at least one drawing executed in color. Copies of this patent or patent application publication with color drawing (s) will be provided by the office upon request and payment of the necessary fee.

DEFINITIONS

Figure 1:
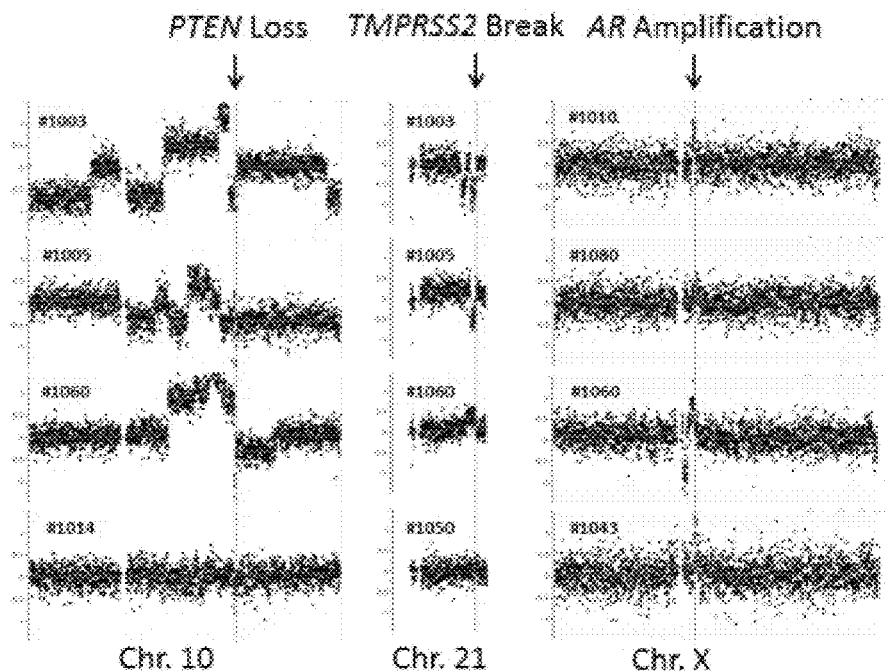
FIG. 1: shows exemplary cfDNA genomic abnormalities detected at specific chromosomal loci. PTEN loss at chromosome 10, TMPRSS2 at chromosome 21, and AR amplification at chromosome X are shown. Arrows indicate the locations of these chromosomal aberrations.

To facilitate an understanding of the present invention, a number of tetras and phrases are defined below. The use of the article "a" or "an" is intended to include one or more. As used herein, terms defined in the singular are intended to include those terms defined in the plural and vice versa.

The term "cell free DNA" or "cell-free DNA" or "cfDNA" refers to strands of deoxyribose nucleic acids (DNA) found free of cells, for example, as extracted or isolated from plasma/serum of circulating blood, extracted from urine or other bodily fluids.

The term "copy number variation" or CNV" or "copy number variability" refers to a comparative numerical change in the presence or absence/gain or loss, of gene fragments having the same nucleotide sequence.

As used herein, the term "gDNA" refers to DNA isolated or extracted from a patient's peripheral mononuclear blood cells, including lymphocytes that are in turn obtained from circulating blood.

As used herein, the term "genome" refers to and includes the genetic material of an organism, both germline and somatic.

The significance of mutations is profoundly influenced by the distinction between germline and soma. Mutations in somatic (body) cells are not transferred to offspring. Mutations that occur in a somatic cell, in the prostate, bone marrow or liver for example, may damage the cell, make the cell cancerous or even kill the cell. Whatever the effect, the ultimate fate of that somatic mutation of DNA, located inside a cell, is to disappear when the cell in which it occurred, or its owner, dies. However, mutated DNA can only be passed to the next generation if it is present in the germline of gametes. Therefore, comparing germline sequences (i.e. using it as a control) allows one to identify changes in somatic cells or cancer cells specific to that patient that are NOT present in noncancerous cells of that same patient. While comparison to germline sequences from gametes can be done, a comparison between cancerous cells and noncancerous cells is also useful. For example, peripheral white blood cells or lymphocytes of the same patient can be used as a control, as representing noncancerous somatic cell sequences. In this manner, mutations found in both cancerous and noncancerous cells can be ignored.

As used herein, the term "aberration" or "abnormality" or "alteration" in singular or plural context refers to a change or deviation. In reference to nucleic acid, an alteration refers to a difference(s) or a change(s) between DNA nucleotide sequences, including differences between CNVs. This actual difference in nucleotides between DNA sequences may be a SNP, and/or a change in a DNA sequence, i.e. fusion, deletion, addition, etc., observed when a fragment of a gDNA sequence is compared to a reference, such as a reference human genome hg19 sequence, when a cfDNA sequence is compared to a control DNA sequence that is not from a tumor cell, such as when cfDNA is compared to reference hg19 sequences; when cfDNA is compared to gDNA, and includes changes over time, such as differences between cfDNA collected during treatment or after treatment compared to pretreatment samples. Differences identified in both gDNA and cfDNA are considered "constitutional."

The term "genomic loci" or "chromosomal loci" refers to a specific physical location or "position" of a gene or other DNA sequence, such as a fragment, on a chromosome, for example, NOTCH1 is considered a locus; 16p11.2 is a positional reference and a region of a chromosome. The plural of locus is "loci".

As used herein, the terms "tumor-associated" or "tumor-related" in reference to cfDNA refers to differences in DNA sequences of cfDNA in a patient whose cancer formed a tumor, such as a prostate cancer patient, when compared to reference DNA, such as when cfDNA is compared to control DNA (gDNA) from a cell that is not a tumor as described herein, or when pre-treatment cfDNA is compared to cfDNA collected during or after treatment.

The term "control" refers to a reference for a test sample, such as control DNA isolated from peripheral mononuclear blood cells and lymphocytes, where these cells are not cancer cells, and the like.

The term "reference genome" or "reference assembly" refers to a digital nucleic acid sequence database, such as the human genome (hg19) database containing hg19 assembly sequences, i.e. accessed through the Human (*Homo sapiens*) University of California Santa Cruz (UCSC) Genome Browser Gateway created by the Genome Bioinformatics Group of UCSC. Hg19 is an alternative name for The February 2009 human reference sequence (GRCh37) produced by the Genome Reference Consortium. (Alternatively the Genome Reference Consortium Human Build 37 (GRCh37)).

The term "genomic window" refers to a region of DNA within chosen nucleotide sequence boundaries. Windows may be separate or overlap.

The term "bin" refers to a group of DNA sequences grouped together, such as in a "genomic bin". A "genomic bin window" refers to grouping DNA sequences using genomic windows.

The term "SNP" or "single plymorphic nucleotide" in reference to a mutation refers to one nucleotide difference in a sequence in comparison to another sequence.

The term "whole genome sequencing" or "complete genome sequencing" or "entire genome sequencing" refers to a laboratory process that determines the DNA sequence of each DNA strand in a sample. The resulting sequences may be referred to as "Raw sequencing data" or read. As used herein, a read is a "mappable" read when the sequence has similarity to a region of a reference chromosomal DNA sequence.

The term "targeted sequencing" refers to a laboratory process that determines the DNA sequence of chosen DNA loci or genes in a sample, for example sequencing a chosen group of cancer-related genes.

The term "sequencing" or "sequence" as a verb refers to a process whereby the nucleotide sequence of DNA, or order of nucleotides, is determined, such as a nucleotide order AGTCC, etc.

The term "sequence" as a noun refers to the actual nucleotide sequence obtained from sequencing; for example, DNA having the sequence AGTCC.

The term "sequencing" in reference to a library refers to a collection of DNA fragments used for sequencing that is stored and propagated in a population of microorganisms through the process of molecular cloning.

The term "genomic library" refers to a collection of the total genomic DNA from a single organism, such as genomic DNA isolated from lymphocytes. The DNA is stored in a population of identical vectors, each containing a different insert of DNA.

The term "mappable" refers to areas that show similarity to and thus "mapped" to a reference sequence, for example, a segment of cfDNA showing similarity to reference sequence in a database, for example, cfDNA having a high percentage of similarity to 8q24.3 in the human genome (hg19) database, is a "mappable read".

The term "biomarker" refers to a characteristic that can be objectively measured as an indicator of normal biological processes, pathogenic processes or a pharmacological response to a therapeutic intervention, for example, an individual biomarker, such a protein, i.e. PSA, or a molecular change, such as an AR gene duplication or a group of differences, such as specific somatic alterations in cfDNA as described herein.

The term "molecular profiling" refers to assigning a specific pattern, or signature, based upon a DNA profile, including one or more polymorphisms; copy number variations, etc.

As used herein, the term "genetic profiling" refers to detecting genetic aberrations (i.e. abnormalities or alterations). One example of "genetic profiling" in relation to prostate cancer patients refers to detecting genomic abnormalities in cfDNA.

The term "molecular biomarker profiling" refers to using specific DNA sequences as biomarkers for detecting genetic aberrations.

As used herein, the term "substantially purified" refers to cfDNA molecules that are removed from their natural environment, isolated or separated or extracted, and are at least 60% free, preferably 75% free, more preferably 90% free, and most preferably 100% free from other components with which they are naturally associated.

The terms "sample" and "specimen" in the present specification and claims are used in their broadest sense. These terms are also used interchangeably. On the one hand they are meant to include a tissue biopsy sample or a liquid sample such as a blood sample, a plasma sample or a urine sample. On the other hand, they are meant to include isolated or purified samples, such as cfDNA samples. In addition, a "sample" may or may not contain cfDNA. Furthermore, it may or may not represent "tumor DNA" and/or "cancer cell associated DNA."

A "test sample" refers to a sample compared to a reference sample or control sample. For example, when comparing samples from a patient before treatment, the first sample is considered a "reference sample" while the second or subsequent samples (after treatment) are considered test samples. A reference sample may also refer to a patient's lymphocyte genomic DNA.

The term "tissue sample" refers to a non liquid sample, such as noncancerous tissue, tissue that is suspected of being cancerous, tissue that is known to be cancerous, and tumor tissue.

The term "blood sample" refers to whole blood, obtained directly from a subject or during a procedure. Procedures such as clotting, or filtering, or treating with EDTA or Sodium Citrate, and the like, are then used for providing a plasma sample from a blood sample and for isolating white blood cells, such as peripheral blood mononuclear cells (PBMC), including lymphocytes.

The term "plasma sample" refers to a liquid sample wherein whole blood cells, i.e. red and white cells, were removed, as an example, isolating plasma from a sample of whole blood as described herein. A plasma sample in reference to plasma cfDNA refers to cfDNA isolated or extracted from plasma.

The term "urine sample" refers to a liquid sample of urine. Urine cfDNA refers to cfDNA isolated or extracted from urine.

The term "obtaining a tissue sample" in reference to removing a tissue sample, such as a biopsy from a subject, refers to conventional biopsy or surgery techniques used for removing a tissue biopsy.

The term "obtaining a liquid sample" or "obtaining a liquid biopsy" in reference to fluid from a subject, refers to methods for obtaining a liquid sample, such as removing a blood sample from a subject by phlebotomy, or collecting a urine sample in a sterile container after it leaves the body of a subject, or by collecting urine by catheter, and the like.

The terms "nucleic acid sequence" or "nucleotide sequence" or "polynucleotide sequence" as used herein, refer to an oligonucleotide or polynucleotide, and fragments or portions thereof, and to DNA or RNA of genomic, cellular, cell free or synthetic origin which may be single- or double-stranded, and represent the sense or antisense strand.

A "variant" of a first nucleotide sequence is defined as a nucleotide sequence that differs from a similar reference sequence or control sequence, e.g., by having one or more deletions, insertions, or substitutions that may be detected using DNA sequencing and/or digital DNA sequence comparison. For example, comparative digital methods may be used to match an entire region or loci or gene or selected fragment of a first DNA sequence to second DNA sequence.

A "deletion" is defined as a change in either nucleotide in which one or more nucleotides are absent as compared to, for example, a reference sequence or control sequence.

An "insertion" or "addition" is that change in a nucleotide sequence which has resulted in the addition of one or more nucleotides as compared to, for example, a reference sequence or control sequence.

A "substitution" results from the replacement of one or more nucleotides by different nucleotides as compared to, for example, a reference sequence or control sequence.

The term "prostate" refers to an organ comprising gland cells, epithelial cells, stem cells, etc., having an outer fibrous covering (capsule) that typically forms a ring around the urethra. The majority of seminal fluid is made by the seminal vesicles that are located next to the prostate. The urethra, which is the tube that carries urine and semen out of the body through the penis, typically goes through the center of the prostate. The prostate gland makes and transports seminal fluid for nourishing, protecting, and transporting sperm. The prostate grows rapidly during puberty, fueled by an increase in male hormones (i.e. androgens) in the body, such as testosterone and dihydrotestosterone (DHT). The prostate usually stays about the same size or grows slowly in adults, as long as male hormones are present.

The term "prostatic" is a general tend for being 'of' or 'from' or 'related' to the prostate gland.

The term "cancer" is intended herein to encompass all forms of abnormal or improperly regulated reproduction of cells in a subject unless prefaced with a particular origin of cancer, such as prostate cancer. The term "cancer" also refers to a disease characterized by uncontrolled cell growth and cell proliferation, i.e. cancer cells, wherein cancer cells often form tumors. A cancer cell has changes in their DNA (deoxyribonucleic acid) that may include germline mutations and/or somatic mutations.

The term "tumor" refers to an abnormal lump or collection of cells, wherein a cancerous tumor contains cancer cells.

The term "prostate cancer" or "prostatic cancer" or "Prostate Carcinoma" or "PCa" refers to a disease where cancer cells develop from the gland cells (i.e. the cells that make the prostate fluid that is added to the semen) and from other cells found in a prostate, such as stem cells. In other words, "prostate cancer" refers to a primary cancer of the prostate. Other types of prostate cancer that starts in the prostate gland include sarcomas, such as small cell carcinomas (small-cell tumors), intralobular acinar carcinomas, ductal carcinomas, clear cell carcinomas, mucinous carcinomas, transitional cell carcinomas; neuroendocrine tumors (other than small cell carcinomas), and the like.

The term "primary cancer" refers to cancer cells that arise in the organ or tissue itself, such as prostate cancer that arose from cells normally found in the prostate.

As used herein, the term "metastatic prostate cancer" refers to patients having prostate cancer cells that migrated (spread) to areas of the body outside of the prostate, such as in metastatic hormone sensitive and metastatic castrate resistant stages.

The term "hormone sensitive prostate cancer" or "HSPC" refers to cancer that responds to androgen hormone treatment.

The term "castrate-resistant prostate cancer" or "CRPC" refers to cancer that shows signs of growing during or after using hormone therapy, such as ADT.

The term "locally advanced prostate cancer" refers to cancer cells that have spread outside the prostate gland, to areas such as the seminal vesicles.

The term "localized cancer" refers to cancer cells that are completely contained within the prostate gland.

The term "early prostate cancer" refers to prostate cancer that has not spread outside of the prostate.

The term "PSA" or "prostate-specific antigen" or "serum prostate-specific antigen" refers to a protein produced by both normal and cancerous prostate cells. A high level of PSA maybe a sign of cancer however the PSA level can also be raised in prostate conditions that are not cancer (i.e. are benign) or when the patient has an infection.

The term "prostate cancer stage" in general refers to a designation used to describe, and is based upon, the size, aggressiveness, and spread of a cancer. A determination of the cancer's designated stage helps to guide treatment and can help predict the chance of curing the cancer. Stages include, stage I to II referring to localized cancer (within the prostate) typically small tumors that are unlikely to grow quickly; while stage III refers to locally advanced prostate cancer considered moderate to large tumors or any size of tumor that could behave aggressively. Stages may include several types of categories, such as tumor (T), lymph node involvement (N) and metastasis status (M). The PSA (prostate-specific antigen) level and the Gleason grade are often used to gauge how aggressive the tumor is and determine which treatment options are available.

The term "Gleason classification system" or "Gleason score" is intended to reflect the amount of cancer and aggressiveness of the tumor estimated from a prostate tissue biopsy. The Gleason grade depends on how the tumor looks under the microscope using methods based on standard light microscopic interpretation of H&E-stained tissue sections reflecting how different the tumor tissue is from normal prostate tissue using a scale from 1 to 5. The higher the Gleason grade, the more likely the tumor is to behave aggressively (i.e. grow faster). The medical professional gives the cancer a number based on the patterns and growth of the cancer cells. The lower the number, the more normal the cancer cells look and the lower the grade. The higher the number, the less normal the cancer cells look and the higher the grade. Grades 1 and 2 are not commonly used because the tumor tissue looks and acts like normal tissue. Most prostate tumors are grade 3 or higher. To assign a "Gleason score" or "Gleason sum", the pathologist looks at the biopsy sample of the tumor to find the 2 most common types of glandular growth patterns within the tumor. A grade from the scale is given to each of these 2 patterns. The 2 grades are added together to get the total "Gleason score". A Gleason score is between 6 and 10. For example, if the grade given to the most common growth pattern is 3 and the grade given to the second most common growth pattern is 4, the total Gleason score is 7. Low and intermediate grades are Gleason scores 6-7. A Gleason score of 7 is an intermediate indication that will grow at a moderate rate. A Gleason score of 8 to 10 is a high grade cancer that is likely to grow more quickly, thus higher Gleason scores indicate more aggressive tumors. A Gleason score might not reflect the actual state of cancer types or growth rates due to other factors.

The term "low-grade" in reference to cancer in a patient refers to a slowly growing cancer.

The term "high grade" in reference to cancer in a patient refers to cancers that are likely to grow more quickly.

The term "high volume" refers to a patient having either or both a visceral (non-lymph nodal) metastasis or >4 bone lesions with at least one present outside the spine or pelvis skeleton at the time of initiating chemotherapy for the CRPC stage, in other words the presence of visceral metastatic disease (i.e. non lymph node disease) and/or 4 or more metastatic skeletal lesions on a bone scan with at least 1 of the 4 being present outside the pelvic or spinal skeleton.

The term "low volume" refers to prostate cancer patients who do not show characteristics of high volume cancer.

The term "active surveillance" refers to a "watch and wait" approach to observe whether a cancer continues to grow.

A prostatectomy is a surgery that completely removes the prostate gland.

The term "androgen" refers to a male hormone, such as testosterone, which acts as a growth factor for prostate tissue, including prostate cancer.

The term "androgen deprivation therapy" or "ADT" refers to a treatment that decreases the body's levels of androgens in order to decrease the size and slow the growth of prostate cancer. ADT can be done by taking medicines that interfere with androgens or by having surgery to remove the testicles (called castration or an orchiectomy). Androgen deprivation therapy is intended to starve cancer cells and cause the prostate gland to shrink.

The term "chemotherapy" or "chemo" refers to medicants administered as treatments, for examples, docetaxel, cabazitaxel, doxorubicin, mitoxantrone, etc., used to treat cancer.

The term "remission" refers to when a cancer patient has cancer that cannot be detected in the body and there are no observable symptoms.

The term "recurrence" refers to a patient that was in remission when a cancer continues to grow or spread after treatment.

The terms "patient" and "subject" refer to a mammal that may be treated using the methods of the present invention. "Subject" and "patient" are used herein interchangeably, and a subject may be any mammal but is preferably a human.

A "reference subject" as used herein refers to an individual that provides a basis to which another subject can be compared. In some embodiments, the term "reference subject" refers to a subject that has cancer. In some embodiments, the term "reference subject" refers to a subject that does not have cancer, such as a "control subject".

The term "control" refers to subjects or samples, such as reference samples, which provide a basis for comparison for experimental subjects or samples.

A "reference tissue" or "reference cells" as used herein in reference to a sample, i.e. a "reference sample", refers to a sample of tissue or cells that may or may not have cancer that are used for comparisons. Thus a "reference" sample thereby provides a basis to which another tissue or cell, for example cancerous tissues or cancer cells can be compared. A pre-treatment sample of tissues or cells may be a reference sample which can be compared to post-treatment sample of tissues or cells. A reference need not be cancer free, such as when a reference sample and a test sample are obtained from the same patient separated by time.

A "reference sample" may also be a "reference cfDNA" sample, such as a "nontumor cfDNA" or a "pretreatment cfDNA" refers to cfDNA used as a control for comparison to cfDNA that may contain tumor cfDNA or cancer cell related DNA, i.e. control cfDNA.

As used herein, the terms "PCR product" and "amplification product" refer to the resultant mixture of compounds after two or more cycles of the PCR steps of denaturation, annealing and extension are complete. These teens encompass the case where there has been amplification of one or more segments of one or more target sequences.

As used herein, the term "allele-specific PCR" or "AS-PCR" refers to amplifying certain alleles or allelic regions of DNA.

As used herein, the term "allele" refers to alternative forms of a gene that arise by mutation and are found at the same place on a chromosome.

As used herein, and incorporated by reference, the term "polymerase chain reaction" ("PCR") refers to the method of K. B. Mullis U.S. Pat. Nos. 4,683,195 and 4,683,202. which describe a method for increasing the concentration of a segment (or fragment) of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced. (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "diagnose" or "diagnosis", as used herein, refers to the determination, recognition, or identification of the nature, cause, or manifestation of a condition based on signs, symptoms, and/or laboratory findings, such as diagnosing a subject having PCa.

The term "administering" in reference to a treatment refers to giving a treatment systemically or locally to inhibit tumor cell spread and/or remove cancer cells from cancer patients, including treating cancer cells to inhibit cancer cell division and/or cancer cell growth and/or kill cancer cells, including by inducing apoptotic cell death. Treatments can be administered by a number of routes, including without limitation, intravenously, intrathecally, intraperitoneally, transmucosal, transepithelially, i.e. transdermally, topically, including, for example, patches and iontophoresis devices, as well as topical application of pastes, salves, or ointments, rectally, orally, vaginally, nasally; alone or in combination with, i.e. co-administering a treatment or therapeutic, such as anti-proliferative drugs to reduce the metastatic load in the patient prior to surgery; or administered after surgery.

The term "co-administer", as used herein, refers to a therapy of the administration of two or more agents, drugs, and/or compounds together (i.e. at the same time), such as when administering a combination therapy, for example, administering a chemotherapeutic agent and ADT.

The term "therapy," used interchangeably herein with "treatment" and variants (e.g., "treating," "administering"), refers to an attempt to prevent or ameliorate a disease ("abnormal condition," "disorder," "syndrome," etc.), such as cancer, or the symptoms thereof, in a patient or a subject. It is not intended that "treating" a disease require curing or eradicating it, such that the treatment may or may not have a therapeutic effect. Therapy can be primary treatment, the first treatment after the initial diagnosis, such as surgery, therapeutics, chemotherapy, radiation, immunotherapy, etc. Therapy can also be treatments after the primary treatment, including follow-up surgery, the same or different therapeutics, chemotherapy, radiation, immunotherapy, etc.

The term "adjuvant therapy" as used herein, refers to additional treatment given after the primary treatment to increase the chances of a cure. In some instances, adjuvant therapy is administered after surgery where all detectable disease has been removed, but where there remains a statistical risk of relapse. Adjuvant therapy may include chemotherapy, radiation therapy, hormone therapy, or biological therapy. For example, hormonal therapy, chemotherapy and radiotherapy are often given following surgery for many types of cancer, including prostate cancer.

The term "changing" in reference to a therapy refers to such actions as stopping the administration of one or more current therapeutics, or administering at least one new therapeutic, for example, for a subject receiving ADT where the cancer cells show continued growth then changing the therapy by beginning co-administering a chemotherapeutic agent.

The "therapeutic agent" or a "chemotherapeutic agent" refers to any agent or compound that is intended to confer a desired therapeutic effect on a subject.

The term "altering" and grammatical equivalents as used herein in reference to the level of any substance and/or phenomenon refers to an increase and/or decrease or change as in substitution, in the quantity of the substance and/or phenomenon, regardless of whether the quantity is determined objectively, and/or subjectively. Examples include altering a nucleotide, such as changing a nucleotide, or altering treatment, such as adding an additional therapeutic.

The term "wild type" refers to a gene or gene product or level of expression that has the characteristics of that gene or gene product or level of expression when isolated or measured from/in a naturally occurring source. A wild type gene is the variant most frequently observed, such as in a population of non-cancer cells, and is thus arbitrarily designed the "normal" or "wild-type" form of the gene. Similarly, a "normal" expression level is a relative amount of mRNA or protein when measured from noncancerous cells or noncancerous tissues.

The term "electropherogram" refers to a plot of results from an analysis done by electrophoresis using an automated DNA sequencer. Electropherograms may be used to determine DNA sequence genotypes, or genotypes that are based on the length of specific DNA fragments.

The term "eluent" refers to a fluid used to a solvent to elute a substance for separating materials, for example, for separating cfDNA from urine.

DESCRIPTION OF THE INVENTION

The present invention relates to methods of using cell-free DNA analysis for guiding treatment of advanced prostate cancer. In particular, liquid biopsies are collected from urine and/or plasma of patients for measuring copy number variation in cell-free DNA associated with metastatic prostate cancer. In particular, urine genomic abnormality (UGA) and plasma genomic abnormality (PGA) values are contemplated for use in predicting treatment responses in advanced prostate cancer patients and for use in making decisions related to androgen deprivation therapy (ADT) treatment outcomes in hormone sensitive stage and for starting or changing chemotherapy treatments in castrate resistant advanced cancer stage, for starting chemotherapy treatments. Currently, prognostic factors for evaluating prostatic carcinoma recommended for routine reporting include TNM stage, serum prostate-specific antigen (PSA), and Gleason grade (score). For higher accuracy in prognostic and predictive use, as in guidance of therapy, an algorithmic method is contemplated herein for use in predicting the outcome of advanced prostate cancer patient therapy based upon a liquid biopsy collected before and during therapy using a algorithmic approach based on counting copy number variations observed in the plasma and/or urine sample of the patient undergoing cancer treatments. In particular, two patient groups were followed in order to determine whether a calculated plasma genome abnormality score (PGA) or urine genome abnormality score (UGA) might be useful in predicting patient response to therapy as in patients having advanced/metastatic prostate cancer: 1) hormone sensitive prostate cancer (HSPC) receiving Androgen Deprivation Therapy (ADT) (earlier substage of metastatic prostate cancer) and 2) Castration resistant prostate cancer (CRPC) (later substage of metastatic prostate cancer) receiving ADT and undergoing docetaxel chemotherapy.

In general, the methods comprise using gDNA from blood lymphocytes as a baseline normal (control) and cfDNA (from blood plasma) as representing tumor DNA. Copy number variation (CNV) was determined by preparing libraries of cfDNA and fragmented gDNA then amplifying the represented DNA sequences. Each fragment was mapped to a reference gene in a human genome (gh19) database for gene identification of the fragment. Then CNVs were counted within each reference gene in the cfDNA sample and compared to the number found in the corresponding reference gene in the gDNA sample for use in determining sequencing-based copy number variation (CNV). A CNV may represent gene duplications (additional DNA), mutational analysis, i.e. presence/change in gene mutations, fusions due to loss of nucleic acids, gene deletions (loss of DNA), etc. before and after/during treatment. Part of this sequence information was used to calculate a PGA/UGA Score.

During the development of the present inventions, predictive methods using copy number variations (CNVs) in cell free DNA (cfDNA), which may include providing a score, for a response to therapy and/or survival from cancer, with or without therapy, and/or for changing therapy, are developed and shown using cfDNA from 'liquid biopsies', i.e. from plasma and/or urine. It is not meant to limit the type of liquid or fluid use as a source of cell free DNA, indeed, a variety of fluids may be used, additionally including blood, peritoneal fluid, seminal fluid, semen, fluids surrounding tumors, and the like. Thus in one embodiment, a predictive method may find use in sorting out patients who are not responding to a therapy, such as ADT alone, who are thereby candidates for additional chemotherapy or if they are already receiving chemotherapy of a particular kind then to switch it to another type of treatment instead. In one embodiment, the therapy is ADT. In one embodiment, the therapy is chemotherapy. In one embodiment, the therapy is ADT and chemotherapy.

In brief, the types of calculations based upon cell-free DNA (i.e. liquid biopsies) include: 1) total genomic cell-free DNA from plasma (blood) is a PGA score as described herein in section I; 2) a 10 gene PGA analysis of cell-free DNA from plasma (a 10-PGA score) as described herein in section II; 3) a 10 gene UGA analysis of cell-free DNA from urine as a UGA (10-UGA score) as described herein in section II; 4) a ratio of PGA/UGA (or 10-PGA/10-UGA) as a score as described herein in section II; 5) a 23 gene analysis from cell-free DNA from plasma PGA (or a 23-PGA score) as described herein in section III; 6) a 23 gene UGA analysis from cell-free DNA from urine (or a 23-UGA score) as described herein in section III; and 7) a ratio of PGA/UGA (as 23-PGA/23-UGA score) as described herein in section III. Indication of a patient whose cancer is progressing is when a UGA or PGA score comparison to a previous UGA or PGA score, from the same patient, stays the same or increases. Thus in one embodiment, a PGA and/or UGA score is used to guide treatment choices for patients having advanced prostate cancer, e.g. metastatic prostate cancer. In one embodiment, a PGA and/or UGA score is used to guide treatment choices for patients treated with ADT having advanced prostate cancer, e.g. metastatic prostate cancer.

Figure 22:
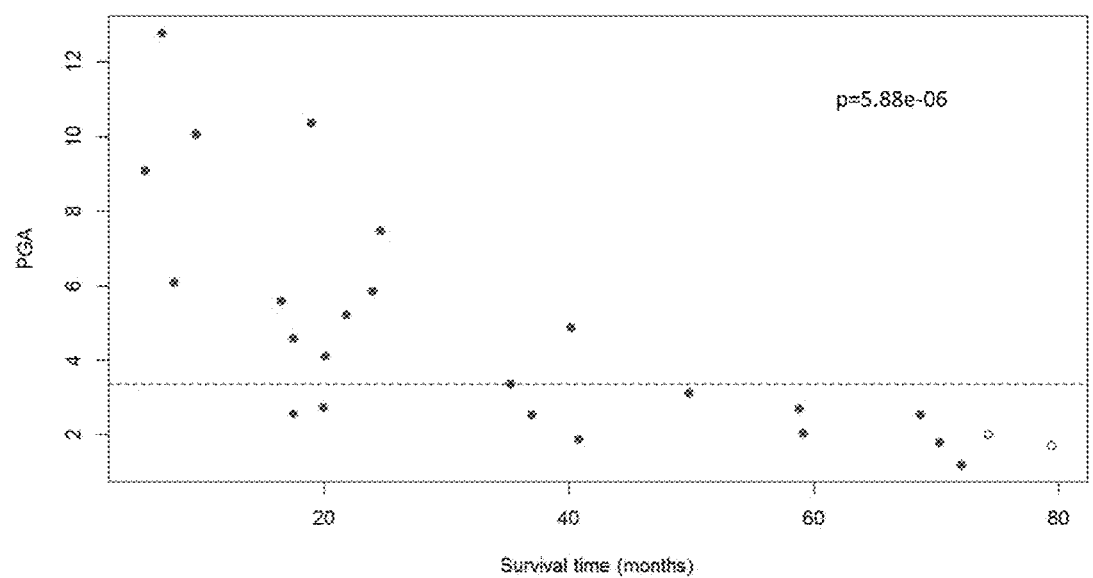
FIG. 22: shows an exemplary scatter plot graphing a 15-gene-based PGA score vs. survival time among 25 CRPC patients. The higher PGA score is significantly associated with poor OS. Y-axis is PGA score. X-axis is follow-up time. P=5.88e-06.
Figure 23:
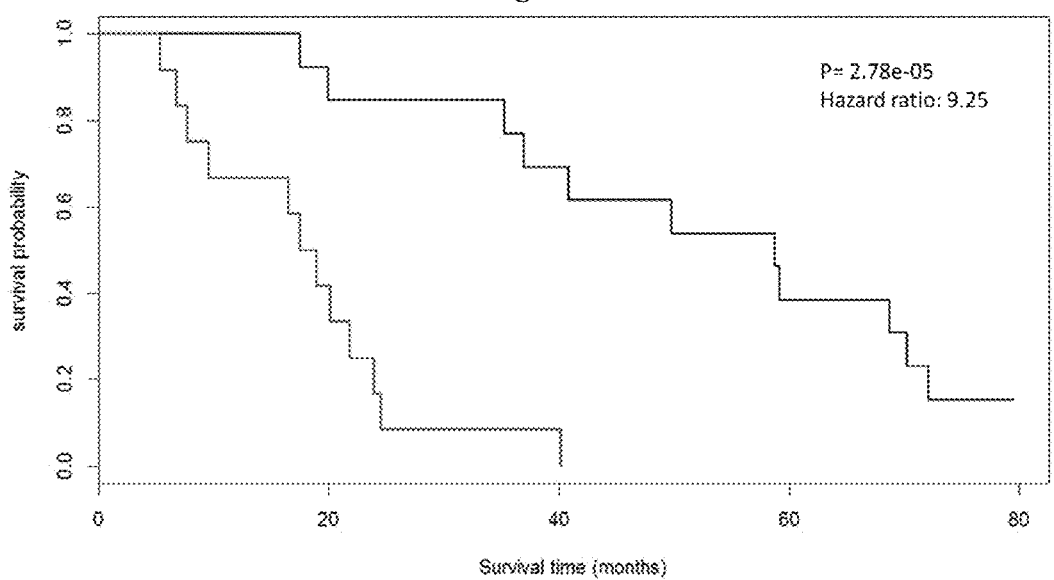
FIG. 23: shows an exemplary risk stratification (high PGA (red line) vs. low PGA (black line): median cut-off) using 15-gene PGA from LOOCV; survival probability vs. survival time (months). Kaplan-Meier analysis shows significant association of higher PGA score and shorter OS (HR=9.25, P=2.78E-05).

In another embodiment, the types of calculations based upon cell-free DNA (i.e. liquid biopsies) include: 1) total genomic cell-free DNA from plasma (blood) as a PGA score as described herein in sections I and IV; 2) a 13 gene PGA analysis of cell-free DNA from plasma (a 13-PGA score) as described herein in sections I and IV; 3) a 13 gene UGA analysis of cell-free DNA from urine as a UGA (13-UGA score) as described herein in sections II and IV; 4) a ratio of PGA/UGA (or 13-PGA/13-UGA) as a score as described herein in sections II and IV; 5) a 15 gene PGA analysis of cell-free DNA from plasma (a 15-PGA score) as described herein in sections I and IV; 6) a 15 gene UGA analysis of cell-free DNA from urine as a UGA (15-UGA score) as described herein in sections II and IV; 7) a ratio of PGA/UGA (or 15-PGA/15-UGA) as a score as describe herein in sections II and IV; 8) Leave-one-out cross-validation (LOOCV) scores as described in sections IV and Example IV; and 9) Overall survival (OS) associations as described in sections IV and Example IV, as shown in FIGS. 22 and 23. Thus, indication of a patient whose cancer is progressing is when a UGA or PGA score comparison to a previous UGA or PGA score, from the same patient, stays the same or increases. Additionally, indication of a patient whose cancer is progressing is when a PGC score is either 1) above 4 (e.g. FIG. 22) or 2) correlates with survival probability of less than 1.0 (e.g. FIG. 23) or 3) associates with a survival time above 0 months and including or less than 80 months (e.g. FIG. 22 and FIG. 23).

Thus in one embodiment, a PGA and/or UGA score is used to guide treatment choices for patients having advanced prostate cancer, e.g. metastatic prostate cancer. In one embodiment, a PGA and/or UGA score is used to guide treatment choices for patients treated with ADT having advanced prostate cancer, e.g. metastatic prostate cancer, ADT failure, etc.

Further, Treatment Efficacy (TEff) indexes were developed based upon pre-PGA/post PGA scores or pre-UGA/post-UGA scores. In particular, TEff index=log 2(prePGA/postPGA)×10, 10-PGA TEff index=log 2(pre10-PGA/post10-PGA)×100; 13-PGA TEff index=log 2(pre13-PGA/post13-PGA)×100; 15-PGA TEff index=log 2(pre15-PGA/post15-PGA)×100; 23-PGA TEff index=log 2(pre23-PGA/post23-PGA)×10, as described accordingly in corresponding sections I, II, III and IV, respectively. For urine, a TEff index=log 2(preUGA/postUGA)×100, 10-UGA TEff index=log 2(pre10-UGA/post10-UGA)×100; 13-UGA TEff index=log 2(pre13-UGA/post13-UGA)×100; 15-UGA TEff index=log 2(pre15-UGA/post15-UGA)×100; and 23-UGA TEff index=log 2(pre23-UGA/post23-UGA)×10, as described accordingly in corresponding sections I, II, III, and IV, respectively. A TEff index of less than or close to zero indicates no response to treatment while a higher TEff index is indicative of a better treatment response. In one embodiment, a TEff index is used to guide treatment choices for patients having advanced prostate cancer. In one embodiment, a TEff index is used to guide treatment choices for patients treated with ADT having advanced prostate cancer.

Thus predictive/guidance methods described herein, based upon copy number variation, for advanced prostate cancer patients receiving ADT alone, are in contrast to numerous other methods used for detecting cancer or prostate cancer using plasma or urine cell free DNA. Examples of other methods are shown in the following publications: Heitzer, et al., "Tumor Associated Copy Number Changes In The Circulation Of Patients With Prostate cancer Identified Through Whole-Genome Sequencing." Genome Med., 5:30 (2013a); WO 2013086352 A1, "Prostate cancer Associated Circulating Nucleic Acid Biomarkers." Schutz, et al., Published Jun. 13, 2013; Kwee, et al., "Measurement of circulating cell-free DNA in relation to 18F-fluorocholine PET/CT imaging in chemotherapy-treated advanced prostate cancer." Clin Transl Sci. 5(1):65-70. Epub 2012 Feb. 23; EP 2774997 A1, "Detection of Androgen Receptor (AR) mutations in circulating tumor DNA from plasma samples of castration-resistant prostate cancer patients using locked nucleic acid-clamp PCR." Published Sep. 10, 2014; Schwarzenbach, et al., "Cell-free Tumor DNA in Blood Plasma As a Marker for Circulating Tumor Cells in Prostate cancer." Clin Cancer Res 15(3) (2009); Ignatiadis, et al., "Circulating Tumor Cells And Circulating Tumor DNA For Precision Medicine: Dream Or Reality?" Annals of Oncology 25: 2304-2313, 2014; Singh, et al., "Serum microRNA expression patterns that predict early treatment failure in prostate cancer patients." Oncotarget, Vol. 5, No. 3: 824 (2014).

In fact, although liquid biopsies are suggested for use in providing cell free DNA and/or RNA in certain clinical applications, such as a diagnostic, predictive for treatment responses, predictive for targeted therapy and prognostic, these publications refer to other types of cancer, cancer in general, or prenatal testing: for examples, Heitzer, et al., "Circulating Tumor DNA as a Liquid Biopsy for Cancer." Clinical Chemistry 61:1 (2014). (Clinchem. 2014). Dawson, et al., "Analysis of Circulating Tumor DNA to Monitor Metastatic Breast Cancer." New Engl J Med., 368; 13:1199 (2013a); Heitzer, et al., "Establishment Of Tumor-Specific Copy Number Alterations From Plasma DNA Of Patients With Cancer." Int. J. Cancer: 133, 346-357 (2013b); Leary, et al., "Detection of Chromosomal Alterations in the Circulation of Cancer Patients with Whole-Genome Sequencing." Sci Transl Med., 4(162): 162ra154 (2012); WO2011/041485, "Method For Non-Invasive Prenatal Ploidy Calling." Apr. 7, 2011; WO2011/051283, "Means And Methods For Non-Invasive Diagnosis Of Chromosomal Aneuploidy." May 5, 2011; US 2011/0039724 A1, "Method For Detecting Chromosomal Aneuploidy." Published Feb. 17, 2011.

Moreover, when liquid biopsies are described in methods for providing cell free DNA in association with prostate cancer, see examples below, the analysis is usually limited to a few genes and/or there is no actual description of scoring patients, in particular for providing a score for a prostate cancer patient undergoing only ADT based on CNV in cfDNA, in order to sort out those patients who are not responding and are thereby candidates for chemotherapy; US 20110230358 A1 "Identification Of Polymorphic Sequences In Mixtures Of Genomic DNA By Whole Genome Sequencing." Published Sep. 22, 2011; Latz, et al., "Diagnostic and Therapeutic Value of Cell-free Circulating DNA as a Non-invasive Biomarker in Patients with Prostate cancer." Current Cancer Therapy Reviews, Volume 9, Number 4:258-264(7) (2013). Abstract only; WO 2012115885 A1 "Circulating Biomarkers." Published Aug. 30, 2012; WO 2014151117 A1 "Identification And Use Of Circulating Nucleic Acid Tumor Markers." Published Sep. 25, 2014; WO 2014014497 A1, "Detecting And Classifying Copy Number Variation In A Cancer Genome." Published Jan. 23, 2014; WO 2013159035 A2, "Highly Sensitive Surveillance Using Detection Of Cell Free DNA." Published Oct. 24, 2013; US 20110230358 A1, "Identification Of Polymorphic Sequences In Mixtures Of Genomic DNA By Whole Genome Sequencing." Published Sep. 22, 2011; Schatz, et al., "Chromosomal Instability in Cell-Free DNA Is a Serum Biomarker for Prostate cancer." Clin Chem. 2014 Oct. 27. pii: clinchem.2014.226571. [Epub ahead of print] abstract only; Feng, et al., "Plasma Cell-Free DNA And Its DNA Integrity As Biomarker To Distinguish Prostate cancer From Benign Prostatic Hyperplasia In Patients With Increased Serum Prostate-Specific Antigen." Int Urol Nephrol. 2013 August; 45(4):1023-8. Epub 2013. Abstract only; Lewinshtein, et al. "Genomic Predictors Of Prostate cancer Therapy Outcomes." Expert Rev Mol Diagn. 10(5):619-36 (2010) abstract only; Shaw, et al., "Genomic Analysis Of Circulating Cell Free DNA Infers Breast Cancer Dormancy." Genome Research 1-10, 2011. (Gr.123497.111). Esposito, et al., "Monitoring Tumor-Derived Cell-Free DNA In Patients With Solid Tumors: Clinical Perspectives And Research Opportunities." Cancer Treatment Reviews, 40(5): 648-655, 2014 abstract only; US 20110201507, "Sequencing Methods And Compositions For Prenatal Diagnoses." Published Aug. 18, 2011. A reference by Delgado, et al., "Characterization of cell-free circulating DNA in plasma in patients with prostate cancer." Tumor Biology, Volume 34, Issue 2, pp 983-986, 2012, describes that prostate cancer patients whose plasma was collected before and 3 months after diagnosis showed cell-free circulating DNA released by apoptotic and non-apoptotic cell death, and suggested that the type of cell-free circulating DNA might change during treatment and suggested it should be followed.

Numerous references list urine as a source of cell free DNA used for cancer detection and/or prognosis, however either do not mention advanced prostate cancer or do not describe a specific method of using urine cell free DNA copy number variation as described herein for advanced prostate cancer. In fact, cell free urine DNA is proposed as a diagnostic to discriminate between prostate cancer and benign prostatic hyperplasia (BPH) in several publications. An example of a recent publication that discusses urine cell free DNA in early prostate cancer without mentioning advanced cancer is by Salvi, et al., "Urine Cell-Free DNA Integrity Analysis for Early Detection of Prostate Cancer Patients." Disease Markers, Volume 2015 (2015), Article ID 574120; the following publications mention cell free DNA and PCR relative copy numbers in relation to specific genes for diagnosing early prostate cancer while not mentioning copy number variations: Yan, et al., "Urinary Nucleic Acid TSPAN13-to-S100A9 Ratio as a Diagnostic Marker in Prostate cancer." J Korean Med Sci. 2015 30(12):1784-1792; and Yun, et al., "Comparison of mRNA, protein, and urinary nucleic acid levels of S100A8 and S100A9 between prostate cancer and BPH." Ann Surg Oncol 2015; 22:2439-2445. Another by Casadio, et al., "Urine Cell-Free DNA Integrity as a Marker for Early Prostate Cancer Diagnosis: A Pilot Study." BioMed Research International, Volume 2013, Article ID 270457 (2013), mentions copy number alterations in one of the genes but does not suggest using CNV for analysis of urine cfDNA. Another reference to DNA biomarkers in urine of prostate cancer patients refer to urinary sediments and do not mention cell free DNA, for example, Hessels and Schalken, "Urinary biomarkers for prostate cancer: a review." Asian J Androl. 15(3): 333-339 2013.

One reference that does not mention cell free DNA or copy number variation describes a scoring system incorporating algorithms using urine and plasma biomarker genes developed for detecting PCa and a prediction of aggressiveness from patients with PCa or benign prostatic hyperplasia (BPH). Levels of UAP1, PDLIM5, IMPDH2, HSPD1, PCA3, PSA, TMPRSS2, ERG, GAPDH, and B2M genes were analyzed. One algorithm distinguished patients with PCa from BPH, another separating Gleason score (GS) of ≥7 from GS of <7 cancer or BPH. By incorporating two algorithms into a scoring system, 75% of the analyzed samples showed concordance between the two models (99% specificity and 68% sensitivity for predicting GS ≥7 in this group). These algorithms are contemplated to assist with both biopsy indication and patient prognosis. Ma, et al., "Diagnostic and prognostic scoring system for prostate cancer using urine and plasma biomarkers." *Genet Test Mol Biomarkers*. 18(3):156-63Epub 2014, Abstract. Analysis of copy number variation in cell-free DNA from prostate patients as described herein is also in contrast with copy number variation or alterations reported using prostate tumor DNA (tissues) for diagnosing prostate cancer, as examples, Liu, et al., "Comprehensive assessment of DNA copy number alterations in human prostate cancers using Affymetrix 100K SNP mapping array."—Tumors. Genes, Chromosomes and Cancer, Volume 45, Issue 11, pages 1018-1032, 2006; and Williams, et al., "Recurrent copy number alterations in prostate cancer: an in silico meta-analysis of publicly available genomic data." Cancer Genetics 207:474-488 (2014) for advanced prostate tumors.

Thus none of these publications describe the methods of the present inventions for scoring advanced prostate cancer patients, nor methods for monitoring patients undergoing ADT treatment for guiding treatment responses, such as starting chemotherapy treatment or changing to different treatments.

Further, although there are several molecular biology tests (and kits) for genetic abnormality analysis of patients for detecting cancer, of which one type of cancer is prostate cancer, and at least one described for monitoring prostate cancer, these tests do not describe the methods of the present inventions. The following are examples of each type of genetic test, such as needle biopsies of prostate/cancer tissue, cfDNA, circulating tumor DNA, or combined exosomal RNA/DNA (exoRNA/DNA) with cell-free DNA (cfDNA). As one example of a test on a needle biopsy, the Oncotype DX prostate cancer test is described by the company to provide a Genomic Prostate Score (GPS) based upon the activity of certain unnamed genes intended to be used for men recently diagnosed with early-stage prostate cancer. The company description actually states that "If your prostate cancer is considered high risk, then you are not a candidate for the Oncotype DX test."

A molecular biology based liquid biopsy test for diagnosing prostate cancer, including high grade cancer, contemplates using plasma and urine exosome RNA/DNA for analyzing three genes, along with cfDNA (no specific genes mentioned), to add these results to prognostic care for high grade cancer patients including prostate cancer patients. Although both blood plasma and urine are mentioned, there is no mention of how their algorithm provides a score other than additional factors such as PSA, age, race, and family history are involved or how it is to be used. In fact, the website states: "the test is intended for use in men 50 years or older with a PSA 2-10 ng/mL presenting for an initial biopsy and it "assigns an individualized risk score for patients that predicts the presence of high-grade (Gleason Score ≥7) prostate cancer." Their website on prostate cancer indicates that results will be used to monitor patients undergoing treatment for adjusting treatment approach, and contemplates cell-free DNA-only platforms. Specifically, Exosome Diagnostics, Inc., describes a plasma-based liquid biopsy for use with patients having solid tumors, which co-isolates and analyzes exosomal RNA/DNA (exoRNA/DNA) with cell-free DNA (cfDNA) across multiple cancers, for example, monitoring BRAF mutant melanoma. Exosome Diagnostics is apparently developing plasma- and urine-based liquid biopsies tests that analyze exoRNA/DNA for cancer biomarkers and can simultaneously isolate and analyze cfDNA to enhance detection of rare mutations, covering 26 genes and 1000 associated mutations in cancer pathways, including EGFR/MAPK and PI3K. This test was reportedly able to predict high-grade prostate cancer biopsy results with 91.9 percent sensitivity. ""Sensitivity" (also called the true positive rate) measures the percentage of high-grade prostate cancer that the test correctly identified. "May 17, 2015. However, there is no mention of advanced prostate cancer or specific treatment that might benefit from using their contemplative cfDNA analysis.

Additionally, a liquid biopsy kit for providing circulating tumor DNA from patients with prostate cancer is advertised for monitoring patients undergoing cancer treatment to check the development of the patient's tumor progression and/or tumor evolution (changes in the type of mutations within a tumor) as it "can lend information about potential drug sensitivity and resistance." (CancerIntercept™-Monitor, Pathway Genomics. However, there is no information on what type of treatment a prostate cancer patient is receiving or type of prostate cancer.

Therefore, in one embodiment, cell-free DNA analysis from advanced prostate cancer patients, as described herein, is contemplated for use in predicting patient outcome from ADT alone for guiding subsequent treatment. In one embodiment, PGA and/or UGA scores are determined from cfDNA obtained using a kit. The following description provides details of the development of scoring methods using cell-free DNA.

I. Plasma Genetic And Genomic Abnormalities Predict Treatment Response And Clinical Outcome In Advanced Prostate Cancer. Xia, Kohli, Huang, Wang, et al., Oncotarget, Vol. 6, No. 18. Apr. 15, 2015.

The following describes the development of a predictive Plasma Genomic Abnormality (PGA) score based upon analysis of cell-free DNA from 2 blood samples collected from each patient, pre and post-treatment, in a set of prostate cancer patients.

A. Overview of Using Plasma Genomic Abnormalities (PGA) Scores (From Liquid Biopsies) For Predicting Disease Progression In Patients Having Advanced Prostate Cancer.

Liquid biopsies, examinations of tumor components in body fluids, have shown promise for predicting clinical outcomes. To evaluate tumor-associated genomic and genetic variations in plasma cell-free DNA (cfDNA) and their associations with treatment response and overall survival, we applied whole genome and targeted sequencing to examine the plasma cfDNAs derived from a set of 20 patients with advanced prostate cancer. Sequencing-based genomic abnormality analysis revealed locus-specific gains or losses that were common in prostate cancer, such as 8q gains, AR amplifications, PTEN losses and TMPRSS2-ERG fusions. To estimate tumor burden in cfDNA, we developed a Plasma Genomic Abnormality (PGA) score by summing the most significant copy number variations from a sample containing total DNA as described herein. Cox regression analysis showed that PGA scores were significantly associated with overall survival (p<0.04). After androgen deprivation therapy or chemotherapy, targeted sequencing showed significant mutational profile changes in genes involved in androgen biosynthesis, AR activation, DNA repair, and chemotherapy resistance. These changes may reflect the dynamic evolution of heterozygous tumor populations in response to these treatments. Thus, non-invasive liquid biopsies are tools to study biological mechanisms underlying therapy-specific resistance and to predict disease progression in patients having advanced prostate cancer.

B. Overview of Biopsy Types.

Traditional biopsies use solid tumor tissues to assess genomic architecture. However, multiple or serial traditional biopsies are impractical because they are hazardous to patients and technically challenging to collect and process. The assessment of tumor-released DNA in body fluids such as cell-free DNAs (cfDNAs) in plasma has the advantage of representing the net effect of the host-tumor genetic fraction in cancer patients (Crowley, et al., "Liquid Biopsy: Monitoring Cancer-Genetics in the Blood." *Nat Rev Clin Oncol*, 10:472-484 2013; Diaz and Bardelli, "Liquid Biopsies: Genotyping Circulating Tumor DNA." *J Clin Oncol*, 32:579-586 2014; Kohli and Tindall, "New Developments in the Medical Management of Prostate Cancer." *Mayo Clinic proceedings*, 85:77-86 2010). Further, whole genome sequencing comparisons has revealed significant copy number variations (CNVs) both in somatic tumor tissues as well as in the cfDNA fractions of cancer patients (Chan, et al., "Cancer Genome Scanning in Plasma: Detection of Tumor-Associated Copy Number Aberrations, Single-Nucleotide Variants, and Tumoral Heterogeneity by Massively Parallel Sequencing." *Clin Chem*, 59:211-224 2013; Heitzer, et al., "Tumor-Associated Copy Number Changes in the Circulation of Patients with Prostate Cancer Identified through Whole-Genome Sequencing." *Genome Mcd*, 5:30 2013; Leary, et al., "Detection of Chromosomal Alterations in the Circulation of Cancer Patients with Whole-Genome Sequencing." *Sci Transl Med*, 4:162ra154 2012; Murtaza, et al., "Non-Invasive Analysis of Acquired Resistance to Cancer Therapy by Sequencing of Plasma DNA." *Nature*, 497: 108-112 2013; Ni, et al., "Reproducible Copy Number Variation Patterns among Single Circulating Tumor Cells of Lung Cancer Patients." *Proc Natl Acad Sci USA*, 110:21083-21088 2013). With the accessibility of sampling as well as the ability to capture the genetic heterogeneity of cancer in peripheral fluids, developing tumor-derived cfDNA as a biomarker for detecting the presence of malignancies, monitoring treatment response, judging prognosis, or evaluating recurrence is contemplated. The examination of tumor components including circulating tumor cells and nucleic acids such as cfDNA in body fluids is often referred to as a liquid biopsy (Crowley, et al., "Liquid Biopsy: Monitoring Cancer-Genetics in the Blood." *Nat Rev Clin Oncol*, 10:472-484 2013; Diaz and Bardelli, "Liquid Biopsies: Genotyping Circulating Tumor DNA." *J Clin Oncol*, 32:579-586 2014; Heitzer, et al., "Circulating Tumor DNA as a Liquid Biopsy for Cancer." *Clinical Chemistry*, 61:112-123 2015).

C. Use of Liquid Biopsies During the Development of the Present Inventions.

Whole genome sequencing-based CNV and targeted sequencing-based mutational analysis in cfDNAs derived from a set of patients with advanced prostate cancer was done during the development of the present inventions. Tumor-related genomic abnormalities in plasma cfDNAs and their association with treatment response and clinical outcome was determined in relation to the patient's clinical status. In order to more precisely reflect tumor burden and estimate treatment response, two types of scoring algorithms were developed based on a composite score from the cfDNA genomic abnormality profiles. The results demonstrated herein, as shown below in section D and the Examples, indicate that non-invasive liquid biopsy technology can serve as a tool for personalized health-care management of advanced prostate cancer.

D. Observed Genomic Abnormalities And Total Genomic PGA Scores (t-PGA) From HSPC Prostate Cancer Patients Treated With ADT Alone Or CRPC Patients Treated With ADT And Chemotherapy.

1. Overall cfDNA Genomic Abnormality In Advanced Prostate Cancer Patients.

Figure 7:
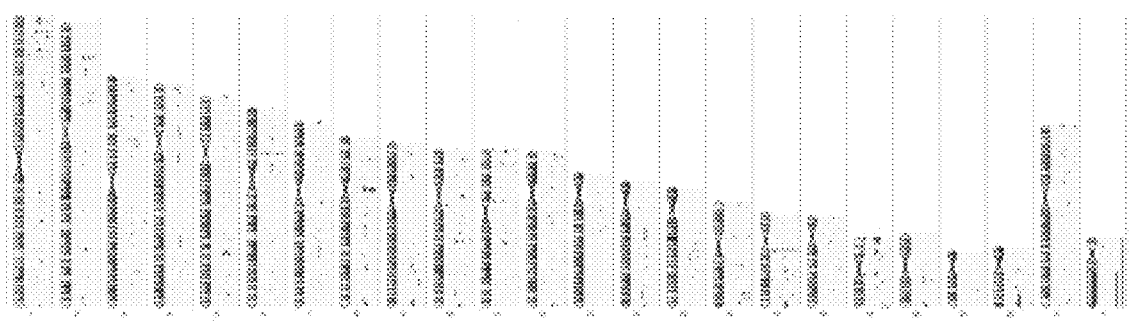
FIG. 7: shows exemplary overall copy number variations in cfDNAs derived from advanced prostate cancer patients. Copy number variations determined by log 2 ratios between cfDNA and matched gDNA were shown in chromosomes 1 through X and Y. Red bars represent chromosome segment amplification (log 2 ratios >0.2) while blue bars represent segment deletion (log 2 ratios <−0.2). There were more copy number changes in CRPC (lower panel) than in HSPC (upper panel) patients.
Figure 7:
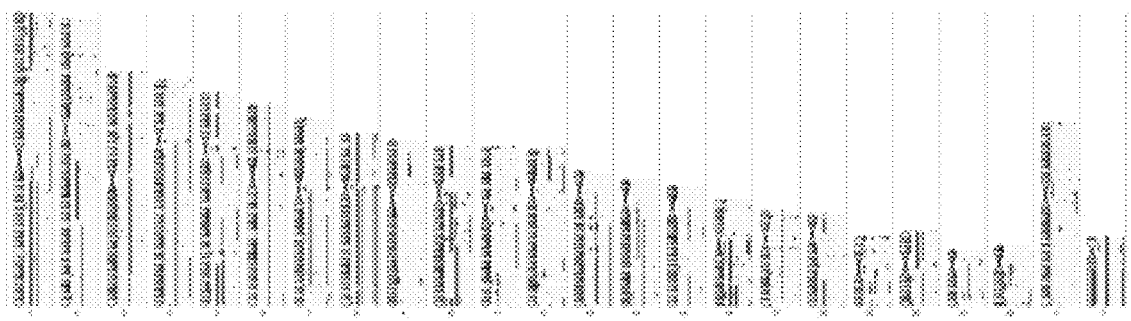

We examined three samples for each patient including pre-treatment cfDNA, post-treatment cfDNA and matched lymphocyte-derived germline DNA (gDNA). Whole genome sequencing generated approximately 14.48 million (ranged from 9.19 to 21.72) mappable reads per sample and approximately 4,560 mappable reads per genomic bin window (1 Mb). CNV analysis using log 2 ratios between cfDNA and matched gDNA showed somatic genomic abnormalities in the 20 patients tested. Overall, we observed more genomic abnormalities in the CRPC cohort undergoing chemotherapy than in the HSPC cohort receiving ADT alone (FIG. 7).

To further define the CNVs, we performed a detailed analysis at chromosomal regions showing frequent aberrations in prostate cancer. Among these, the genomic region at the androgen receptor (AR) was most frequently reported to be amplified (Koivisto, et al., "Androgen Receptor Gene Amplification: A Possible Molecular Mechanism for Androgen Deprivation Therapy Failure in Prostate Cancer." *Cancer Res*, 57:314-319 1997; Taplin and Balk, "Androgen Receptor: A Key Molecule in the Progression of Prostate Cancer to Hormone Independence." *J Cell Biochem*, 91:483-490 2004). To examine the amplification status, we zoomed into the genomic region containing AR and observed AR locus amplification in 1 of 10 HSPC (#1080) and 3 of 10 CRPC cases (#1010, #1043 and #1060) (FIG. 1).

Another common genomic aberration in prostate cancer was various fusion genes at the TMPRSS2 locus (Loeb, et al., "Active Surveillance for Prostate Cancer: A Systematic Review of Clinicopathologic Variables and Biomarkers for Risk Stratification." *Eur Urol*, 67:619-626 2015; Yao, et al., "Evaluation of the Tmprss2:Erg Fusion for the Detection of Prostate Cancer: A Systematic Review and Meta-Analysis." *Tumour Biol*, 35:2157-2166 2014). We observed two CRPC patients (#1003 and #1005) with genomic loss and two patients with genomic gain-one CRPC patient (#1060) and one HSPC patient (#1050). Both genomic losses resulted in the TMPRSS2-ERG fusion gene (FIG. 1). The genomic loss at the TMPRSS2 locus was present in two CRPC patients with a pathological diagnosis of small cell carcinoma (neuro-endocrine origin). These two patients did not show AR amplification. The third most common genomic abnormality was PTEN deletion (Phin, et al., "Genomic Rearrangements of Pten in Prostate Cancer." *Front Oncol*, 3:240 2013; Yoshimoto, et al., "Pten Genomic Deletions That Characterize Aggressive Prostate Cancer Originate Close to Segmental Duplications." *Genes Chromosomes Cancer*, 51:149-160 2012), which was detected in four CRPC cases (#1003, #1005, #1014 and #1060) but not in any of the HSPC cases (FIG. 1).

2. Plasma Genomic Abnormality (PGA) Score And Its Clinical Association.

Figure 2:
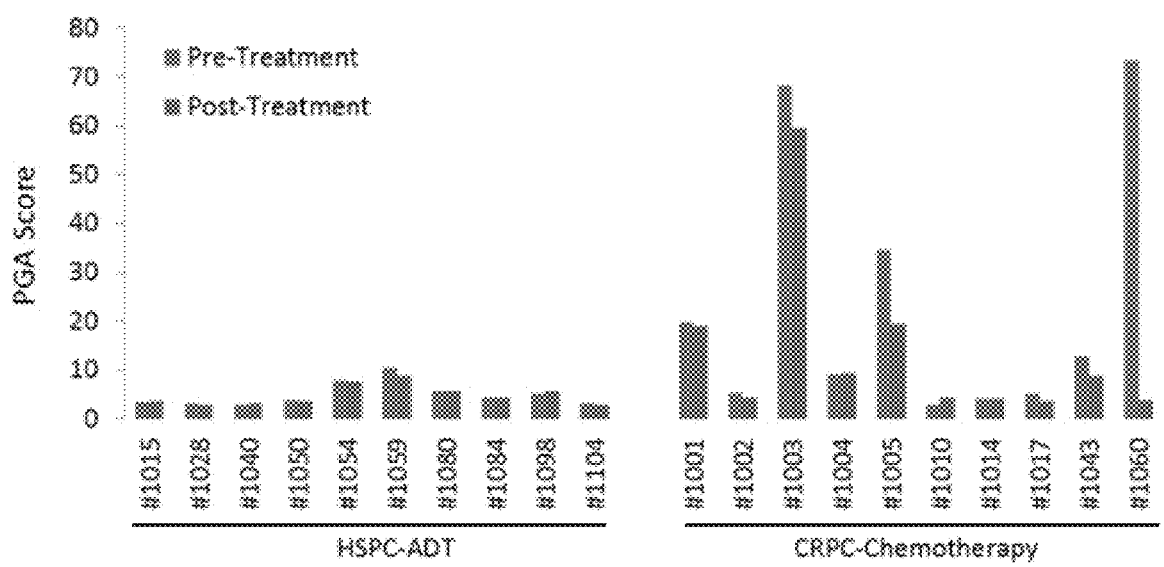
FIG. 2: shows exemplary Plasma genomic abnormality (PGA) scores in 20 patients with advanced prostate cancer. Higher PGA scores indicated more tumor-associated somatic abnormalities in cfDNA and were associated with disease progression and overall survival.
Figure 3:
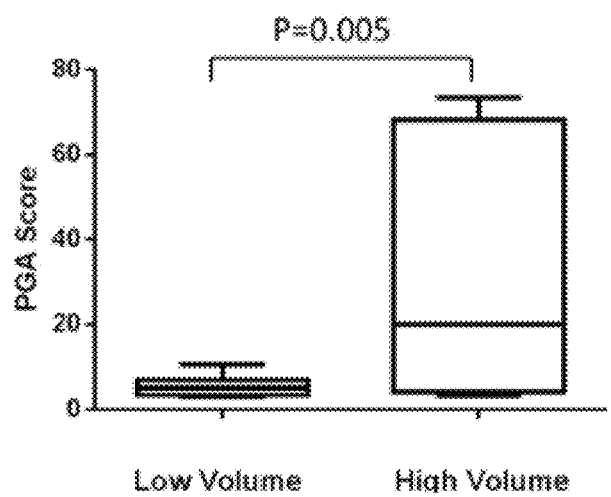
FIG. 3: shows exemplary PGA score differences between high and low volume prostate cancer patients (see main text for definition). Average PGA score before treatment is significantly lower in low volume patients (n=13) than in high volume patients (n=7).

To quantify the tumor DNA fraction in cfDNA, we summed the squared 95th-99th absolute log 2 ratios as the PGA score. Similar to gross chromosomal abnormality, the PGA scores were significantly higher in the CRPC cohort than in the HSPC cohort (FIG. 2). To estimate potential association of PGA scores with overall survival, we performed Cox regression analysis in 19 of the 20 patients with complete follow-up data. We found that elevated PGA scores in pre-treatment samples were significantly associated with short survival (p=0.01, 95% CI=1.01-1.08). We also observed this association in post-treatment samples (p=0.04, 95% CI=1.00-1.20). Among the 20 patients, 7 were classified as having high volume disease (Table 1), defined by the presence of either a visceral (non-lymph nodal) metastasis or >4 bone lesions with at least one present outside the spine or pelvis skeleton at the time of initiating chemotherapy for the CRPC stage. Five of the 7 high volume cancer patients showed high initial PGA scores (cutoff value >10) but only 1 of 13 low volume patients demonstrated high initial PGA score (p=0.005, unpaired t test) (FIG. 3).

Figure 4:
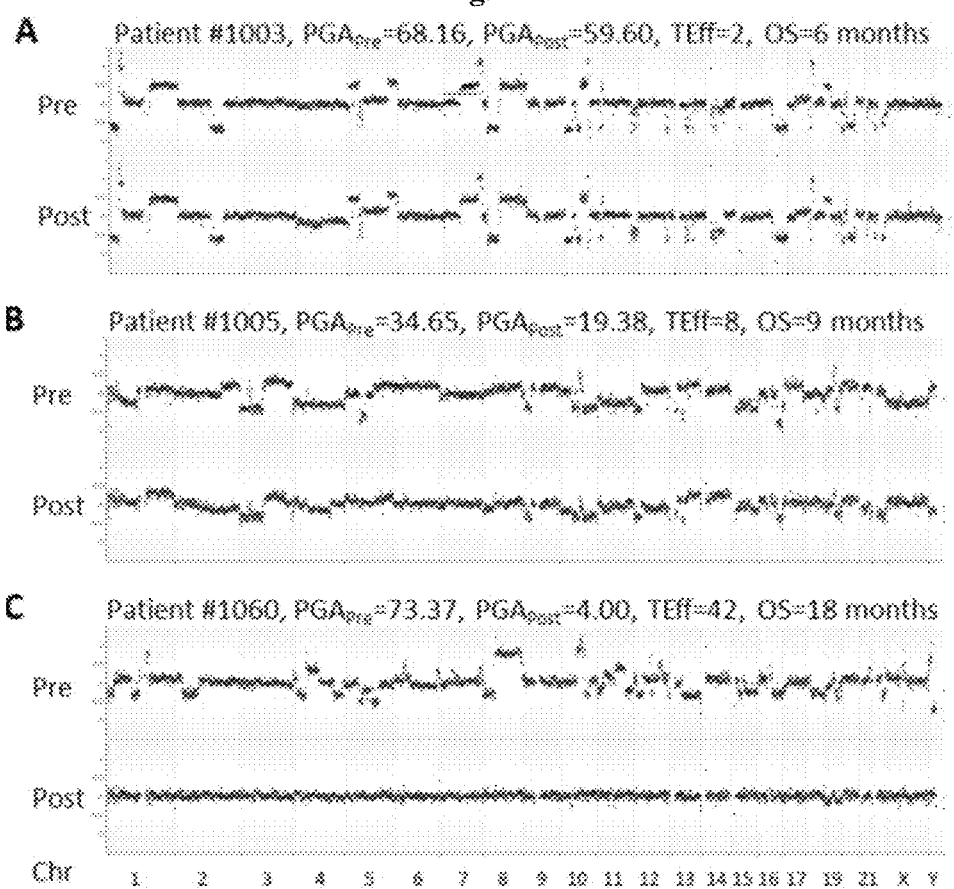
FIG. 4: shows an exemplary comparison of PGA scores and TEff indexes in three representative CRPC patients. Chromosomes were shown on the x-axis while GC-adjusted log 2 ratios (black dots) in 1 Mb windows were on the y-axis. Red lines indicate the trend of copy number variations. Complete, partial and no responses to chemotherapy were displayed in A (patient 1060), B (patient 1005), and C (patient 1003), respectively. OS=overall survival.

For the 10 HSPC patients undergoing ADT, PGA score changes between treatments were minor. This was attributable to relatively low tumor burden in this group of patients. After a median follow-up time of 53.8 months (range 42-95 months), only one patient (#1054) was deceased due to disease. This patient showed relatively high PGA scores in both pre- and post-ADT in the HSPC cohort (FIG. 2). For the 10 CRPC patients receiving chemotherapy, the patients with the highest initial PGA score included #1003, 1005 and 1060. These three patients died with relatively short survival time. To estimate patients' response to treatment, we calculated their Treatment Efficacy (TEff) indexes by transforming PGA score differences between pre- and post-treatments (see method section). We found that the TEff indexes in patients 1003, 1005, and 1060 were 2, 8, and 42, respectively. Correspondingly, their overall survival times were 6, 9 and 18 months (FIG. 4).

3. Cancer Gene Mutational Profiles.

Figure 8:
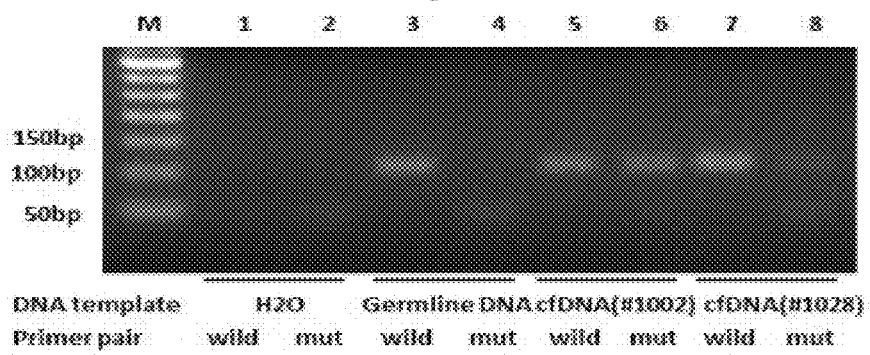
FIG. 8: shows exemplary representative AS-PCR for mutation validation. 103 bp fragments in NUP214 were amplified by AS-PCR and subjected to agarose gel electrophoresis. Lanes 1, 3, 5 and 7 were wild type-specific primer pairs. Lane 2, 4, 6 and 8 are mutant-specific primer pairs. Lanes 1 and 2 were blank control without DNA template. Lanes 3 and 4 were wild type genomic DNA. Lanes 5 and 6 were cfDNAs from patient #1002. Lanes 7 and 8 were cfDNAs from patient #1028. Mutants were detected in lanes 6 and 8.

To identify somatic mutations in cfDNAs, we performed the targeted sequencing of 578 cancer-related genes in the 20 patients. The average mapped reads per patient was 14.46 million (range 9.11-19.74) with 44% of reads on target (range 41-48%). Sequences of the samples achieved a mean coverage of 79× (range 54-87). Among 10 HSPC patients, we identified somatic mutations in 66 genes in pre-ADT and 68 genes in post-ADT samples after removing constitutional polymorphisms (cfDNA vs. matched gDNA). Of these mutated genes, 17 were shared between pre- and post-treatment samples. Among 10 CRPC patients, we identified somatic mutations in 52 genes in pre-chemotherapy and 63 genes in post-chemotherapy samples, of which 18 genes were shared (Supplementary Tables S1-S4). To validate these mutations, we applied allele-specific PCR (AS-PCR) to examine 26 mutations in 41 samples with mutations found by sequencing technology. AS-PCR successfully confirmed 20 of these mutations (FIG. 8). The remaining 6 mutations were uncertain due to difficulty in establishing high quality AS-PCR assays.

4. Gene Mutation Profile Changes Between Pre- and Post-Treatment.

Figure 5:
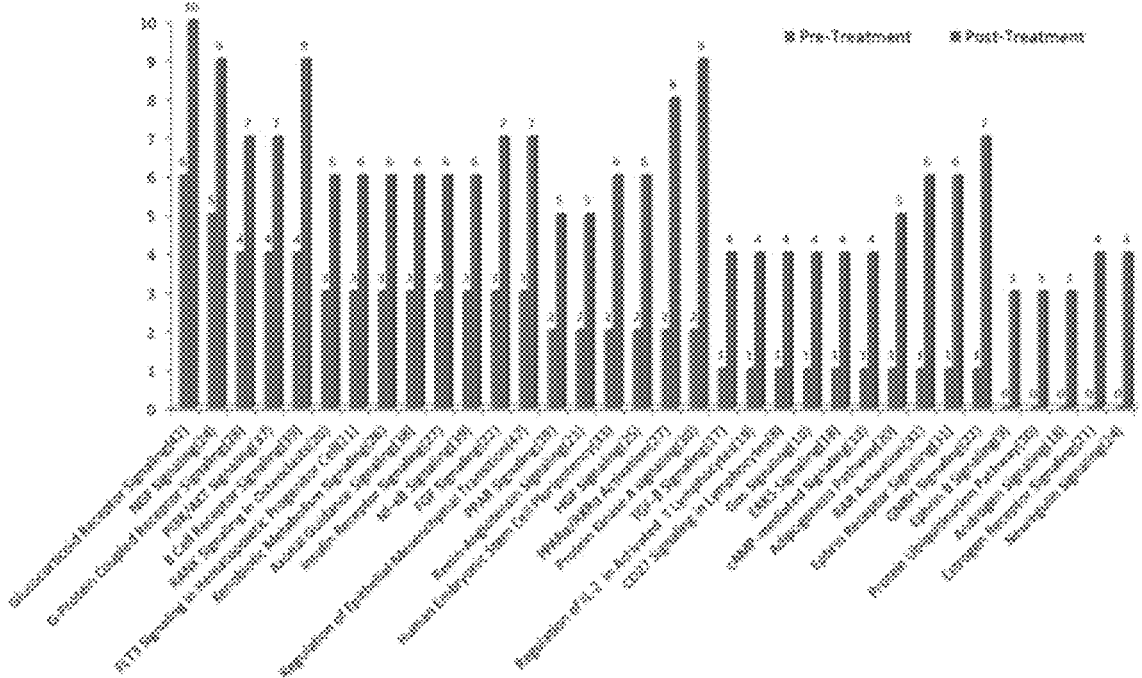
FIG. 5: shows exemplary mutational profile changes between pre-ADT and post-ADT. Gene mutation pathway enrichment analysis was performed in the HSPC cohort receiving standard ADT. More gene mutations were observed in post- than in pre-treatment samples. Pathways involved in androgen biosynthesis, metabolism, and androgen receptor activation are among the most commonly mutated.

To examine treatment-associated pathway alterations, we analyzed the two patient cohorts separately. Overall, we observed 34 and 35 pathways showing >3 gene differences between pre- and post-treatment samples in the HSPC and CRPC cohorts, respectively. Compared to pre-treatment samples, mutations in post-treatment samples were more diverse, reflecting more pathways involved. For HSPC patients, we observed more gene mutations in post-than in pre-treatment samples in these pathways (FIG. 5). The genes involving androgen biosynthesis and metabolism including androgen signaling, estrogen receptor signaling and GNRH signaling pathways were among the most commonly mutated. For example, GNRH signaling pathway is a target of ADT and contains 22 genes. Of those, only 1 gene mutation was detected before ADT with 7 gene mutations detected after ADT.

Figure 6:
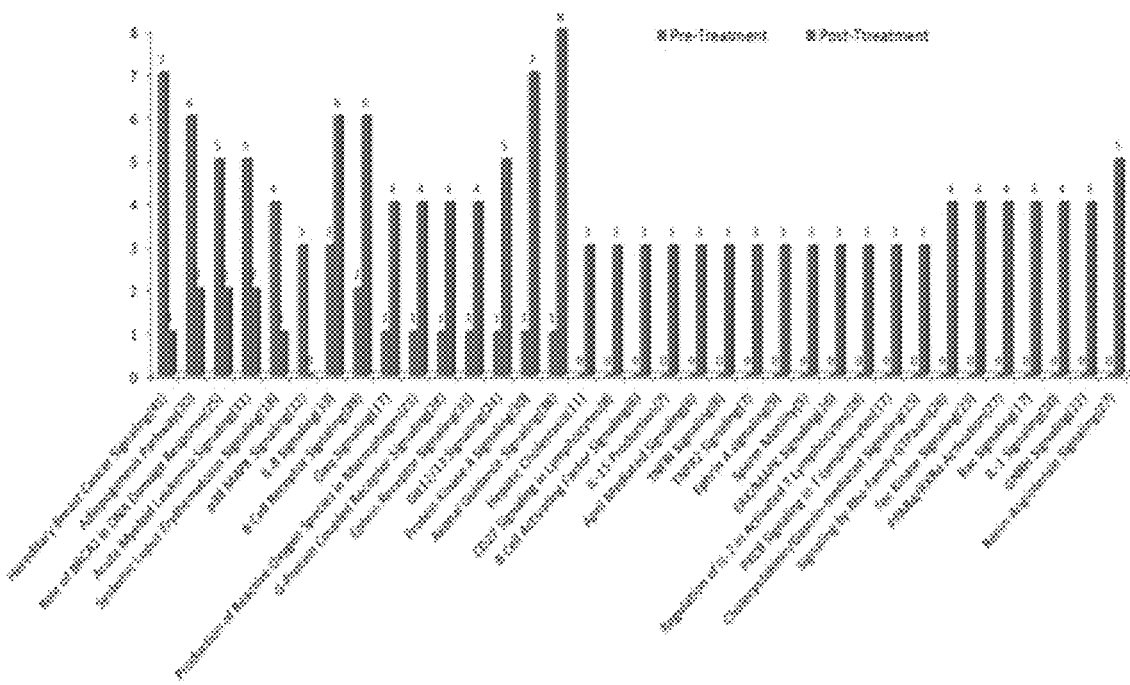
FIG. 6: shows exemplary mutational profile changes between pre- and post-chemotherapy. Many mutations detected after chemotherapy were not present in pre-treatment samples. The most common mutations in pre-treatment samples were in DNA repair-related hereditary breast cancer signaling pathways. The most common mutations in post-treatment samples occurred in the pathways related to AR regulation and resistance to chemotherapy including axonal guidance signaling, protein kinase A signaling, and renin-angiotensin signaling pathways.

For CRPC patients, 20 of 35 pathways had gene mutations in post-treatment patients, not in the pretreatment patients. The most common mutations in the post-treatment group included axonal guidance signaling, protein kinase A signaling and renin-angiotensin signaling pathways. Meanwhile, 6 pathways showed less gene mutations in post-than in pre-treatment samples (FIG. 6). The most common mutations before chemotherapy occurred in DNA repair-related hereditary breast cancer signaling genes. Among 41 genes in the pathway, 7 mutations were detected in the pre-treatment while merely 1 mutation was found in the post-treatment samples.

For CRPC patients, 20 of 35 pathways had gene mutations in post-treatment patients, not in the pretreatment patients. The most common mutations in the post-treatment group included axonal guidance signaling, protein kinase A signaling and renin-angiotensin signaling pathways. Meanwhile, 6 pathways showed less gene mutations in post-than in pre-treatment samples (FIG. 6). The most common mutations before chemotherapy occurred in DNA repair-related hereditary breast cancer signaling genes. Among 41 genes in the pathway, 7 mutations were detected in the pre-treatment while merely 1 mutation was found in the post-treatment samples.

Table 1. Clinical Characteristics of 20 Advanced Prostate Cancer Patients.

TABLE 1

Clinical Characteristics Of 20 Advanced Prostate Cancer Patients

| Patient ID | Age at time of Diagnosis (years) | Patient Group | Treatment | Gleason Score at Diagnosis | TNM staging at Diagnosis | Metastatic status before treatment* | PSA (ng/ml) at time of 1st sample collection in advanced stage | PSa (ng/ml) at time of 2nd sample collection in advanced stage | Time period (days) between two sample collections | Vital status Alive = 0; Dead = 1 | Follow-up time (months) |
|---|---|---|---|---|---|---|---|---|---|---|---|
| 1001 | 62 | CRPC | Chemo | 9 | T4N1M1 | High Volume | 8.2 | 0.42 | 147 | 0 | 37.12 |
| 1002 | 66 | CRPC | Chemo | 7 | T2cNxM0 | Low Volume | 9.3 | 1.6 | 89 | 1 | 17.23 |
| 1003 | 54 | CRPC | Chemo | 7 | T3aN0M0 | High Volume | 107 | 162 | 84 | 1 | 6.64 |
| 1004 | 69 | CRPC | Chemo | 8 | T3aNxM0 | Low Volume | 3.4 | 4.6 | 84 | 0 | 49.18 |
| 1005 | 69 | CRPC | Chemo | 9 | T3bN2M1 | High Volume | 0.48 | 0.1 | 92 | 1 | 9.07 |
| 1010 | 72 | CRPC | Chemo | 9 | T3bN1M0 | High Volume | 5 | NA | 140 | 1 | 21.53 |
| 1014 | 61 | CRPC | Chemo | 7 | T2bN1M1 | High Volume | 126 | 56.8 | 99 | 1 | 19.82 |
| 1017 | 63 | CRPC | Chemo | 5 | T2aN0M0 | Low Volume | 22 | 104 | 139 | 0 | 16.21 |
| 1043 | 73 | CRPC | Chemo | 7 | T2aNxM1 | High Volume | 15.5 | 8 | 80 | 0 | 32.22 |
| 1060 | 78 | CRPC | Chemo | 7 | TxNxM1 | High Volume | 3.7 | 1.4 | 104 | 1 | 18.48 |
| 1015 | 69 | HSPC | ADT | 7 | T2cNxM0 | Low Volume | 1 | 0.9 | 98 | 0 | 53.77 |
| 1028 | 49 | HSPC | ADT | 9 | T3bN0M0 | Low Volume | 0.33 | 0.12 | 154 | 0 | 95.27 |
| 1040 | 53 | HSPC | ADT | 9 | T2NxM0 | Low Volume | 2.5 | <0.10 | 165 | 0 | 42.93 |
| 1050 | 64 | HSPC | ADT | 9 | T3bN1M1 | Low Volume | 4.2 | <0.10 | 136 | 0 | 57.47 |
| 1054 | 51 | HSPC | ADT | 7 | T2aNxMo | Low Volume | 6.4 | <0.10 | 154 | 1 | 54.33 |
| 1059 | 62 | HSPC | ADT | 9 | T3bN1M0 | Low Volume | 2.9 | <0.10 | 116 | 0 | 55.20 |
| 1080 | 65 | HSPC | ADT | 8 | T3bN1M0 | Low Volume | 16 | 0.77 | 172 | 0 | 49.27 |
| 1084 | 57 | HSPC | ADT | 9 | T3bN0M0 | High Volume | 2.2 | 0.24 | 78 | 0 | 53.80 |
| 1098 | 78 | HSPC | ADT | 6 | T2aNxM0 | Low Volume | 5.7 | 0.54 | 131 | 0 | NA |
| 1104 | 67 | HSPC | ADT | 9 | T2cN1M1 | Low Volume | 37 | <0.10 | 99 | 0 | 51.60 |

*High Volume Metastatic disease definition: 4 of more metastatic skeletal lesions on bone scan with at least 1 of the 4 being present outside the pelvic or spinal skeleton and/or presence of visceral metastatic disease (non lymph node disease).

Supplementary Table 1. Gene Mutations In Pre-Treatment Patients.

SUPPLEMENTARY TABLE 1

Gene mutations in pre-treatment patients only.

| Chromosome | Position | Patient ID | Treatment | Mutant Allele Frequency % Pre-Treatment | Depth | Gene name | DNA Change | Amino Acid Change |
|---|---|---|---|---|---|---|---|---|
| chr10 | 81465798 | 1043 | Chemotherapy | 25.9 | 54 | NUTM2B | c.383C>T | p.A128V |
| chr02 | 48040930 | 1001 | Chemotherapy | 7.9 | 164 | FBXO11 | c.2083G>A | p.G695S |
| chr01 | 27101460 | 1010 | Chemotherapy | 7.8 | 64 | ARID1A | c.4742A>C | p.H1581P |
| chr01 | 11199588 | 1043 | Chemotherapy | 7.2 | 69 | MTOR | c.5000T>G | p.V1667G |
| chr10 | 114711242 | 1002 | Chemotherapy | 5.3 | 130 | TCF7L2 | c.257C>T | p.A86V |
| chr20 | 39742611 | 1005 | Chemotherapy | 4.9 | 101 | TOP1 | c.1454T>C | p.L485P |
| chr14 | 105239429 | 1017 | Chemotherapy | 4.9 | 141 | AKT1 | c.958G>A | p.V320M |
| chr14 | 56145161 | 1002 | Chemotherapy | 4.8 | 124 | KTN1 | c.3947C>T | p.T1316M |
| chr01 | 157550138 | 1060 | Chemotherapy | 4.8 | 83 | FCRL4 | c.1250G>T | p.G417V |
| chr09 | 134106018 | 1017 | Chemotherapy | 4.1 | 97 | NUP214 | c.6202T>G | p.F2068V |
| chr05 | 149437068 | 1002 | Chemotherapy | 3.8 | 129 | CSF1R | c.2220A>T | p.O740H |
| chr17 | 8050789 | 1002 | Chemotherapy | 3.5 | 57 | PER1 | c.1496A>C | p.O499P |
| chr13 | 29041658 | 1005 | Chemotherapy | 3.5 | 170 | FLT1 | c.161G>T | p.R54M |
| chr14 | 105239428 | 1005 | Chemotherapy | 3.4 | 144 | AKT1 | c.959T>G | p.V320G |
| chr01 | 16248745 | 1001 | Chemotherapy | 3.3 | 219 | SPEN | c.1751T>G | p.V584G |
| chr23 | 44833911 | 1003 | Chemotherapy | 3.3 | 59 | KDMGA | c.335C>A | p.A112E |
| chr09 | 134015937 | 1002 | Chemotherapy | 3.3 | 121 | NUP214 | c.1257T>G | p.5419R |
| chr02 | 113984674 | 1005 | Chemotherapy | 3.2 | 153 | PAX8 | c.1339T>G | p.W447G |
| chr04 | 153271195 | 1001 | Chemotherapy | 3.2 | 91 | FBXW7 | c.583A>G | p.S195G |
| chr03 | 37053312 | 1003 | Chemotherapy | 3.1 | 129 | MLH1 | c.547T>A | p.Y183N |
| chr11 | 117096648 | 1010 | Chemotherapy | 3.1 | 96 | PCSK7 | c.859A>G | p.S287G |
| chr01 | 164818578 | 1003 | Chemotherapy | 3.1 | 189 | PBX1 | c.1202A>C | p.H401P |
| chr05 | 176715820 | 1003 | Chemotherapy | 3.1 | 95 | NSD1 | c.6152G>T | p.G2051V |
| chr17 | 17124847 | 1003 | Chemotherapy | 3.0 | 66 | FLCN | c.875A>G | p.E292G |
| chr13 | 28979918 | 1002 | Chemotherapy | 3.0 | 164 | FLT1 | c.1550A>G | p.K517R |
| chr16 | 89849267 | 1003 | Chemotherapy | 2.9 | 203 | FANCA | c.1626G>T | p.E542D |
| chr06 | 168291542 | 1001 | Chemotherapy | 2.9 | 302 | MLLT4 | c.1007G>T | p.G336V |
| chr05 | 170827158 | 1001 | Chemotherapy | 2.8 | 321 | NPM1 | c.526delG | p.M176fs |
| chro5 | 170827159 | 1001 | Chemotherapy | 2.8 | 321 | NPM1 | c.527delA | p.V175fs |
| chr02 | 216191545 | 1005 | Chemotherapy | 2.8 | 211 | ATIC | c.532G>A | p.A178T |
| chr01 | 154143187 | 1043 | Chemotherapy | 2.7 | 72 | TPM3 | c.643T>A | p.Y215N |
| chr11 | 71735321 | 1010 | Chemotheram | 2.6 | 113 | NUMA1 | c.207G>T | p.O69H |
| chr17 | 8053751 | 1003 | Chemotherapy | 2.5 | 78 | PER1 | c.274A>T | p.S92C |
| chr19 | 11130287 | 1010 | Chemotherapy | 2.5 | 159 | SMARCA4 | c.2506G>T | p.G836. |
| chr19 | 16192724 | 1010 | Cheroothreapy | 2.5 | 118 | TPM4 | c.242C>T | p.A81V |
| chr06 | 33290639 | 1005 | Chemotherapy | 2.5 | 78 | DAXX | c.53G>T | p.S18I |
| chr20 | 40141486 | 1001 | Chemotherapy | 2.5 | 347 | CHD5 | c.851A>G | p.E284G |
| chr15 | 74326873 | 1005 | Chemotherapy | 2.5 | 118 | PML | c.1712T>G | p.V571G |
| chr15 | 74327477 | 1010 | Chemotherapy | 2.5 | 80 | PML | c.1715C>T | p.S572F |
| chr06 | 117704481 | 1017 | Chemotherapy | 2.5 | 198 | ROS1 | c.2495delA | p.K832fs |
| chr02 | 128017023 | 1010 | Chemotherapy | 2.5 | 159 | ERCC3 | c.2066T>G | p.V689G |
| chr17 | 7579508 | 1003 | Chemotherapy | 2.4 | 82 | TP53 | c.179C>A | p.P60Q |
| chr07 | 26233195 | 1010 | Chemotherapy | 2.4 | 122 | HNRNPA2B1 | c.877G>T | p.G293. |
| chr16 | 10989527 | 1043 | Chemotherapy | 2.3 | 347 | CHTA | c.246A>C | p.E82D |
| chr06 | 168289896 | 1002 | Chemotherapy | 2.3 | 129 | MLLT4 | c.896T>A | p.V299D |
| chr17 | 7578553 | 1001 | Chemotherapy | 2.2 | 226 | TP53 | c.377A>C | p.Y1265 |
| chr19 | 7705606 | 1017 | Chemotherapy | 2.2 | 134 | STXBP2 | c.269A>C | p.H90P |
| chr17 | 29557279 | 1002 | Chemotherapy | 2.2 | 87 | NF1 | c.2992T>C | p.Y998H |
| chr08 | 38274934 | 1010 | Chemotherapy | 2.2 | 136 | FGFR1 | c.1646C>A | p.S549. |
| chr11 | 119199899 | 1005 | Chemotherapy | 2.2 | 88 | CBL | c.1564G>T | p.A522S |
| chr04 | 1932354 | 1005 | Chemotherapy | 2.1 | 140 | WHSC1 | c.1412T>G | p.V471G |
| chr22 | 40831504 | 1060 | Chemotherapy | 2.1 | 189 | MKL1 | c.167G>A | p.R56K |
| chr12 | 57911053 | 1010 | Chemotherapy | 2.1 | 139 | DDIT3 | c.204_206delAGA | p.E68_E69delinsE |
| chr01 | 92752047 | 1060 | Chemotherapy | 2.1 | 93 | GLMN | c.735A>G | p.I245M |
| chr06 | 167453392 | 1010 | Chemotherapy | 2.1 | 94 | FGFR1OP | c.1126C>T | p.L376F |
| chr02 | 25552009 | 1010 | Chemotherapy | 2.0 | 143 | DNMT3A | c.176delC | p.P59fs |
| chr22 | 29120965 | 1060 | Chemotherapy | 2.0 | 148 | CHEK2 | c.721G>A | p.V241I |
| chr23 | 70320535 | 1059 | ADT | 7.9 | 50 | FOXO4 | c.455A>C | p.N152T |
| chr03 | 178951883 | 1028 | ADT | 6.4 | 78 | PIK3CA | c.2938T>G | p.F980V |
| chr05 | 131325794 | 1080 | ADT | 6.2 | 96 | ACSLG | c.449A>G | p.E150G |
| chr08 | 134271412 | 1080 | ADT | 6.0 | 116 | NDRG1 | c.388G>T | p.G130W |
| chr19 | 1220373 | 1028 | ADT | 5.3 | 56 | STK11 | c.466T>G | p.Y156D |
| chr16 | 15851685 | 1028 | ADT | 5.2 | 57 | MYH11 | c.1595C>T | p.P532L |
| chr08 | 90949302 | 1084 | ADT | 5.1 | 78 | NBN | c.2186T>A | p.V729E |
| chr23 | 133547521 | 1015 | ADT | 4.7 | 87 | PHF6 | c.422C>A | p.A141D |
| chr10 | 102896426 | 1104 | ADT | 4.6 | 65 | TLX1 | c.772T>G | p..258E |
| chr02 | 25505304 | 1104 | ADT | 4.4 | 89 | DNMT3A | c.454T>G | p.S152A |
| chr03 | 188426055 | 1028 | ADT | 4.4 | 89 | LPP | c.1204G>T | p.G402C |
| chr17 | 17127456 | 1028 | ADT | 4.0 | 98 | FLCN | c.398T>G | p.V133G |

SUPPLEMENTARY TABLE 1-continued

Gene mutations in pre-treatment patients only.

| Chromosome | Position | Patient ID | Treatment | Mutant Allele Frequency % Pre-Treatment | Depth | Gene name | DNA Change | Amino Acid Change |
|---|---|---|---|---|---|---|---|---|
| chr09 | 139413043 | 1028 | ADT | 3.9 | 51 | NOTCH1 | c.1099T>G | p.G367S |
| chr02 | 223066160 | 1028 | ADT | 3.8 | 103 | PAX3 | c.1422T>G | p.S474R |
| chr17 | 5286418 | 1028 | ADT | 3.7 | 80 | RABEP1 | c.2489T>G | p.V830G |
| chr02 | 100721967 | 1080 | ADT | 3.5 | 84 | AFF3 | c.322C>T | p.R108C |
| chr09 | 134015937 | 1028 | ADT | 3.4 | 88 | NUP214 | c.1257T>G | p.S419R |
| chr09 | 135985684 | 1050 | ADT | 3.4 | 88 | RALGDS | c.487T>G | p.R163G |
| chr24 | 15470400 | 1098 | ADT | 3.2 | 61 | UTY | c.1420C>A | p.Q474K |
| chr03 | 142168444 | 1084 | ADT | 3.2 | 62 | ATR | c.7762G>A | p.A2588T |
| chr10 | 63816877 | 1084 | ADT | 3.1 | 159 | ARID5B | c.848T>G | p.V283G |
| chr15 | 91185167 | 1104 | ADT | 3.1 | 96 | CRTC3 | c.1655A>C | p.D552A |
| chr11 | 108205697 | 1104 | ADT | 3.1 | 129 | ATM | c.8012T>G | p.V2671G |
| chr11 | 106856796 | 1028 | ADT | 3.0 | 132 | GUCY1A2 | c.365G>T | p.G122V |
| chr01 | 206669446 | 1028 | ADT | 3.0 | 99 | IKBKE | c.2119C>A | p.L707I |
| chr01 | 2489166 | 1104 | ADT | 2.9 | 103 | TNFRSF14 | c.71T>G | p.V24G |
| chr06 | 28872442 | 1015 | ADT | 2.9 | 300 | TRIM27 | c.947T>A | p.V316E |
| chr19 | 30311610 | 1015 | ADT | 2.9 | 100 | CCNE1 | c.464T>G | p.V155G |
| chr02 | 190670379 | 1015 | ADT | 2.9 | 101 | PMS1 | c.317T>A | p.V106D |
| chr11 | 67257510 | 1104 | ADT | 2.8 | 107 | AIP | c.470T>G | p.V157G |
| chr11 | 68177382 | 1028 | ADT | 2.8 | 173 | LRP5 | c.2092A>C | p.T698P |
| chr11 | 118363772 | 1015 | ADT | 2.8 | 107 | KMT2A | c.5005G>A | p.A1669T |
| chr11 | 128846306 | 1028 | ADT | 2.8 | 173 | LRP5 | c.2092A>C | p.T698P |
| chr09 | 132686221 | 1098 | ADT | 2.8 | 141 | FNBP1 | c.1042delC | p.Q348fs |
| chr17 | 37054666 | 1015 | ADT | 2.7 | 146 | LASP1 | c.251T>G | p.V84G |
| chr10 | 70442594 | 1098 | ADT | 2.7 | 185 | TET1 | c.4916T>G | p.V1639G |
| chr16 | 89805887 | 1015 | ADT | 2.7 | 110 | FANCA | c.4009delA | p.S1337fs |
| chr15 | 99500291 | 1015 | ADT | 2.7 | 109 | IGF1R | c.3724T>G | p.F1242V |
| chr02 | 208442312 | 1084 | ADT | 2.7 | 182 | CREB1 | c.814C>T | p.P2725 |
| chr14 | 68758602 | 1084 | ADT | 2.6 | 151 | RAD51B | c.758T>G | p.V253G |
| chr02 | 97215059 | 1028 | ADT | 2.6 | 75 | ARID5A | c.122A>C | p.D41A |
| chr15 | 99500291 | 1104 | ADT | 2.5 | 150 | IGF1R | c.3724T>G | p.F1242V |
| chr01 | 3348531 | 1050 | ADT | 2.5 | 116 | PRDM16 | c.3526T>G | p.C1176 |
| chr19 | 4364128 | 1104 | ADT | 2.5 | 118 | SH3GL1 | c.422A>C | p.D141A |
| chr12 | 4398155 | 1028 | ADT | 2.5 | 118 | CCND2 | c.719T>G | p.V240G |
| chr03 | 52584764 | 1080 | ADT | 2.5 | 238 | PBRM1 | c.4778A>C | p.Q1593P |
| chr15 | 74883901 | 1098 | ADT | 2.5 | 78 | ARID3B | c.1166G>T | p.G389V |
| chr19 | 45297462 | 1028 | ADT | 2.4 | 124 | CBLC | c.1286T>G | p.V429G |
| chr09 | 123933826 | 1050 | ADT | 2.4 | 121 | CNTRL | c.6417G>T | p.Q2139H |
| chr17 | 29685988 | 1040 | ADT | 2.3 | 84 | NF1 | c.8115delT | p.S2705fs |
| chr10 | 43620332 | 1028 | ADT | 2.3 | 127 | RET | c.2941T>G | p.Y981D |
| chr03 | 186502485 | 1028 | ADT | 2.3 | 85 | EIF4A2 | c.211G>T | p.G71W |
| chr01 | 3348531 | 1104 | ADT | 2.2 | 218 | PRDM16 | c.3526T>G | p.C1176G |
| chr17 | 9862581 | 1028 | ADT | 2.2 | 131 | GAS7 | c.43T>C | p.S15P |
| chr14 | 51196242 | 1040 | ADT | 2.2 | 135 | NIN | c.6077A>G | p.Q2026R |
| chr06 | 135511266 | 1015 | ADT | 2.2 | 175 | MYB | c.308T>G | p.V103G |
| chr02 | 25470026 | 1050 | ADT | 2.1 | 182 | DNMT3A | c.1016T>G | p.V339G |
| chr19 | 45561447 | 1080 | ADT | 2.1 | 137 | ERCC1 | c.845T>A | p.V282E |
| chr09 | 98211605 | 1040 | ADT | 2.1 | 93 | PTCH1 | c.3550G>A | p.V1184M |
| chr13 | 103518017 | 1040 | ADT | 2.1 | 91 | ERCC5 | c.1955G>T | p.G652V |
| chr13 | 103518017 | 1040 | ADT | 2.1 | 91 | BIVM-ERCC5 | c.3317G>T | p.G1106V |
| chr08 | 134274395 | 1104 | ADT | 2.1 | 322 | NDRG1 | c.221A>C | p.N74T |
| chr04 | 1932354 | 1028 | ADT | 2.0 | 197 | WHSC1 | c.1412T>G | p.V471G |
| chr17 | 30315340 | 1054 | ADT | 2.0 | 146 | SUZ12 | c.1025G>T | p.R342M |
| chr17 | 36881810 | 1104 | ADT | 2.0 | 143 | MLLT6 | c.3322A>T | p.T1108S |
| chr11 | 68177382 | 1098 | ADT | 2.0 | 147 | LRP5 | c.2092A>C | p.T698P |
| chr17 | 79941431 | 1050 | ADT | 2.0 | 149 | ASPSCR1 | c.160T>G | p.F54V |
| chr11 | 125514408 | 1028 | ADT | 2.0 | 146 | CHEK1 | c.1103A>C | p.N368T |

Supplementary Table 2. Gene Mutations In Post-Treatment Patients.

SUPPLEMENTARY TABLE 2

Gene Mutations In Post-Treatment Patients.

| Chromosome | Position | Patient ID | Treatment | Mutant Allele Frequency % Post-Treatment | Depth | Gene name | DNA Change | Amino Acid Change |
|---|---|---|---|---|---|---|---|---|
| chr23 | 44918252 | 1001 | Chemotherapy | 15.6 | 51 | KDM6A | c.877T>G | p.C293G |
| chr01 | 11199588 | 1005 | Chemotherapy | 8.3 | 84 | MTOR | c.500T>G | p.V1667G |
| chr17 | 5036205 | 1001 | Chemotherapy | 6.9 | 472 | USP6 | c.196A>C | p.K66Q |
| chr17 | 39778604 | 1005 | Chemotherapy | 6.5 | 55 | KRT17 | c.673_675delGTG | p.V225del |
| chr01 | 11199588 | 1001 | Chemotherapy | 6.5 | 138 | MTOR | c.5000T>G | p.V1667G |
| chr02 | 1.28E+08 | 1017 | Chemotherapy | 5.8 | 102 | ERCC3 | c.2066T>G | p.V689G |
| chr19 | 18856633 | 1017 | Chemotherapy | 5.5 | 90 | CRTC1 | c.292A>C | p.T98P |
| chr19 | 18856633 | 1001 | Chemotherapy | 5.5 | 179 | CRTC1 | c.292A>C | p.T98P |
| chr08 | 1.42E+08 | 1002 | Chemotherapy | 5.5 | 217 | PTK2 | c.2478_2483delTTACCA | p.H826_Q828delinsQ |
| chr09 | 21974675 | 1017 | Chemotherapy | 5.3 | 56 | CDKN2A | c.152T>G | p.V51G |
| chr05 | 1.12E+08 | 1017 | Chemotherapy | 5.0 | 79 | APC | c.935T>G | p.V312G |
| chr01 | 1.65E+08 | 1001 | Chemotherapy | 5.0 | 179 | PBX1 | c.1202A>C | p.H401P |
| chr10 | 88988020 | 1001 | Chemotherapy | 4.9 | 101 | NUTM2A | c.383C>T | p.A128V |
| chr10 | 43622023 | 1005 | Chemotherapy | 4.4 | 89 | RET | c.3040G>T | p.D1014Y |
| chr09 | 21974675 | 1005 | Chemotherapy | 4.3 | 91 | CDKN2A | c.152T>G | p.V51G |
| chr17 | 66523982 | 1005 | Chemotherapy | 4.2 | 165 | PRKAR1A | c.710G>T | p.G237V |
| chr09 | 98268880 | 1014 | Chemotherapy | 4.2 | 94 | PTCH1 | c.203G>C | p.G68A |
| chr06 | 1.18E+08 | 1017 | Chemotherapy | 4.1 | 193 | ROS1 | c.5777A>G | p.H1926R |
| chr01 | 1.57E+08 | 1043 | Chemotherapy | 3.8 | 77 | NTRK1 | c.2117T>G | p.V706G |
| chr14 | 56107845 | 1001 | Chemotherapy | 3.7 | 107 | KTN1 | c.2022T>G | p.S674R |
| chr22 | 24143268 | 1017 | Chemotheraoy | 3.6 | 222 | SMARCB1 | c.473G>T | p.W158L |
| chr03 | 47088110 | 1005 | Chemotherapy | 3.6 | 111 | SETD2 | c.6964_6965insT | p.S2322fs |
| chr08 | 1.42E+08 | 1017 | Chemotherapy | 3.5 | 57 | PTK2 | c.662G>T | p.R221L |
| chr03 | 47088111 | 1005 | Chemotherapy | 3.5 | 113 | SETD2 | c.6964A>T | p.S2322C |
| chr05 | 1.77E+08 | 1002 | Chemotherapy | 3.4 | 176 | NSD1 | c.5147G>A | p.G1716E |
| chr07 | 1.43E+08 | 1003 | Chemotherapy | 3.2 | 91 | EPHB6 | c.2959G>A | p.D987N |
| chr01 | 1.86E+08 | 1060 | Chemotherapy | 3.2 | 124 | TPR | c.6796G>T | p.62266C |
| chr17 | 12920437 | 1043 | Chemotherapy | 3.1 | 95 | ELAC2 | c.247T>G | p.Y83D |
| chr16 | 23693386 | 1001 | Chemotherapy | 3.1 | 352 | PLK1 | c.724T>G | p.Y242D |
| chr03 | 52620442 | 1003 | Chemotherapy | 3.1 | 129 | PBRM1 | c.3485delA | p.K1162fs |
| chr01 | 2.07E+08 | 1017 | Chemotherapy | 3.1 | 64 | IKBKE | c.1342G>A | p.E448K |
| chr23 | 70354208 | 1043 | Chemotherapy | 3.0 | 98 | MED12 | c.4619T>G | p.V1540G |
| chr14 | 56105903 | 1017 | Chemotherapy | 3.0 | 98 | KTN1 | c.1786A>C | p.T596P |
| chr05 | 56184054 | 1017 | Chemotherapy | 3.0 | 65 | MAP3K1 | c.4259T>A | p.V1420E |
| chr23 | 70354208 | 1010 | Chemotherapy | 2.9 | 134 | MED12 | c.4619T>G | p.V1540G |
| chr07 | 91674323 | 1014 | Chemotherapy | 2.9 | 101 | AKAP9 | c.5260T>A | p.Y1754N |
| chr11 | 65836145 | 1005 | Chemotherapy | 2.8 | 107 | SF3B2 | c.2617_2617insA | p.Q873fs |
| chr09 | 14146688 | 1002 | Chemotherapy | 2.8 | 138 | NFIB | c.925G>A | p.D309N |
| chr02 | 25470026 | 1010 | Chemotherapy | 2.8 | 177 | DNMT3A | c.1016T>G | p.V339G |
| chr19 | 7705606 | 1014 | Chemotherapy | 2.7 | 108 | STXBP2 | c.269A>T | p.H90L |
| chr19 | 45296732 | 1017 | Chemotherapy | 2.7 | 144 | CBLC | c.1139A>C | p.H380P |
| chr10 | 1.04E+08 | 1001 | Chemotherapy | 2.7 | 71 | NFKB2 | c.2073_2084delTGCTGACATCCA | p.G691_H695delinsG |
| chr08 | 57128992 | 1060 | Chemotherapy | 2.7 | 111 | CHCHD7 | c.130G>T | p.E44, |
| chr01 | 10434375 | 1001 | Chemotherapy | 2.7 | 220 | KIF1B | c.4948A>C | p.T1650P |
| chr09 | 1.34E+08 | 1003 | Chemotherapy | 2.6 | 149 | NUP214 | c.1894T>G | p.F632V |
| chr09 | 1.39E+08 | 1017 | Chemotherapy | 2.6 | 76 | NOTCH1 | c.2352C>G | p.S784R |
| chr01 | 19062126 | 1043 | Chemotherapy | 2.6 | 75 | PAX7 | c.1156G>T | p.V386L |
| chr01 | 1.65E+08 | 1014 | Chemc therapy | 2.6 | 153 | PBX1 | c.1202A>C | p.H401P |
| chr22 | 31724773 | 1005 | Chemotherapy | 2.5 | 117 | PATZ1 | c.1645G>T | p.E549. |
| chr16 | 15269766 | 1043 | Chemotherapy | 2.5 | 120 | ABCC6 | c.2326T>G | p..776G |
| chr16 | 23693386 | 1043 | Chemotherapy | 2.5 | 240 | PLK1 | c.724T>G | p.Y242O |
| chr10 | 1.03E+08 | 1043 | Chemotherapy | 2.4 | 124 | PAX2 | c.307T>G | p.Y103D |
| chr07 | 1.43E+08 | 1017 | Chemotherapy | 2.4 | 123 | EPHB6 | c.101A>T | p.E34V |
| chr04 | 1941510 | 1060 | Chemotherapy | 2.4 | 82 | WHSC1 | c.1886_1888delAAT | p.K629_630delinsK |
| chr02 | 1.28E+08 | 1001 | Chemotherapy | 2.4 | 250 | ERCC3 | c.2066T>G | p.V689G |
| chr10 | 1.04E+08 | 1010 | Chemotherapy | 2.3 | 127 | NFKB2 | c.2225T>C | p.V742A |
| chr08 | 48846525 | 1010 | Chemotherapy | 2.3 | 211 | PRKDC | c.1621_1623delATG | p.M541del |
| chr07 | 1.43E+08 | 1003 | Chemotherapy | 2.3 | 126 | EPHB6 | c.101A>G | p.E34G |
| chr11 | 1.17E+08 | 1003 | Chemotherapy | 2.2 | 90 | PCSK7 | c.914A>C | p.K305T |
| chr09 | 1.33E+08 | 1003 | Chemotherapy | 2.2 | 132 | FNBP1 | c.1036G>T | p.G346C |
| chr06 | 1.07E+08 | 1017 | Chemotherapy | 2.2 | 132 | PRDM1 | c.1775T>G | p.V592G |
| chr03 | 97367131 | 1014 | Chemotherapy | 2.2 | 90 | EPHA6 | c.1154A>C | p.D385A |
| chr03 | 1.85E+08 | 1014 | Chemotherapy | 2.2 | 89 | ETV5 | c.495C>A | p.N165K |
| chr17 | 8050569 | 1017 | Chemotherapy | 2.1 | 94 | PER1 | c.1628C>A | p.P543Q |
| chr17 | 79941431 | 1027 | Chemotherapy | 2.1 | 139 | ASPSCR1 | c.160T>G | p.F54V |
| chr16 | 16269766 | 1060 | Chemotherapy | 2.1 | 188 | FANCG | c.2326T>G | p..776 |
| chr09 | 35076430 | 1060 | Chemotherapy | 2.1 | 139 | ABCC6 | c.1075A>G | p.R359G |
| chr03 | 48719479 | 1005 | Chemotherapy | 2.1 | 93 | NCKIPSD | c.597T>A | p.5199R |
| chr01 | 38188713 | 1010 | Chemotherapy | 2.1 | 95 | EPHA10 | c.1960G>A | p.G654R |

SUPPLEMENTARY TABLE 2-continued

Gene Mutations In Post-Treatment Patients.

| Chromosome | Position | Patient ID | Treatment | Mutant Allele Frequency % Post-Treatment | Depth | Gene name | DNA Change | Amino Acid Change |
|---|---|---|---|---|---|---|---|---|
| chr23 | 44969325 | 1003 | Chemotherapy | 2.0 | 99 | KDM6A | c.4163T>G | p.V1388G |
| chr22 | 40831504 | 1010 | Chemotherapy | 2.0 | 243 | MKL1 | c.167G>T | p.R56M |
| chr09 | 87563377 | 1017 | Chemotherapy | 2.0 | 198 | NTRK2 | c.1765A>C | p.T589P |
| chr08 | 27303312 | 1017 | Chemotherapy | 2.0 | 288 | PTK2B | c.2216T>G | p.V739G |
| chr04 | 55968064 | 1014 | Chemotherapy | 2.0 | 146 | KDR | c.2266G>T | p.G756C |
| chr01 | 1.45E+08 | 1017 | Chemotherapy | 2.0 | 199 | PDE4DIP | c.3490T>G | p.C1164G |
| chr19 | 4365568 | 1084 | ADT | 8.1 | 74 | SH3GL1 | c.242T>G | p.V81G |
| chr17 | 39778607 | 1028 | ADT | 7.7 | 51 | KRT17 | c.672_673delAG | p.224fs |
| chr22 | 41531818 | 1028 | ADT | 7.0 | 128 | EP300 | c.1530T>G | p.S510R |
| chr08 | 1.42E+08 | 1080 | ADT | 6.3 | 141 | PTK2 | c.326G>A | p.R109K |
| chr01 | 3322060 | 1028 | ADT | 5.9 | 50 | PRDM16 | c.1037T>G | p.V346G |
| chr05 | 1.5E+08 | 1028 | ADT | 5.5 | 90 | PDGFRB | c.40G>A | p.G14S |
| chr12 | 1.13E+08 | 1084 | ADT | 5.1 | 58 | PTPN11 | c.1881T>G | p..461G |
| chr09 | 1.24E+08 | 1080 | ADT | 4.8 | 104 | CNTRL | c.1652C>T | p.S551F |
| chr05 | 1.77E+08 | 1040 | ADT | 4.6 | 65 | NSD1 | c.4303T>C | p.C1435R |
| chr19 | 7703906 | 1028 | ADT | 4.5 | 66 | STXBP2 | c.89T>G | p.V30G |
| chr06 | 18258586 | 1104 | ADT | 4.4 | 67 | DEK | c.196T>G | p.L66V |
| chr19 | 16186858 | 1104 | ADT | 4.2 | 95 | TPM4 | c.116T>G | p.V39G |
| chr11 | 65836146 | 1098 | ADT | 4.2 | 70 | SF3B2 | c.2618delA | p.Q873fs |
| chr06 | 41654832 | 1080 | ADT | 4.2 | 94 | TFEB | c.845T>C | p.L282P |
| chr01 | 10434375 | 1040 | ADT | 3.7 | 134 | KIF1B | c.4948A>C | p.T1650P |
| chr03 | 52441975 | 1028 | ADT | 3.6 | 82 | BAP1 | c.374A>G | p.E125G |
| chr02 | 2.08E+08 | 1084 | ADT | 3.6 | 55 | CREB1 | c.304A>C | p.I102L |
| chr11 | 1.19E+08 | 1080 | ADT | 3.3 | 141 | CBL | c.2038C>A | p.P680T |
| chr23 | 70354208 | 1098 | ADT | 3.4 | 88 | MED12 | c.4619T>G | p.V1540G |
| chr06 | 44220782 | 1050 | ADT | 3.4 | 86 | HSP90AB1 | c.1732G>T | p.V578L |
| chr23 | 70357576 | 1054 | ADT | 3.3 | 59 | MED12 | c.5836G>T | p.G1946C |
| chr11 | 1.19E+08 | 1084 | ADT | 3.2 | 124 | CBL | c.197T>G | p.V66G |
| chr03 | 1.29E+08 | 1028 | ADT | 3.2 | 123 | CNBP | c.223G>A | p.A75T |
| chr01 | 18960797 | 1080 | ADT | 3.2 | 93 | PAX7 | c.86T>G | p.V29G |
| chr12 | 1.12E+08 | 1054 | ADT | 3.1 | 96 | ALDH2 | c.1523T>G | p.V508G |
| chr07 | 13978742 | 1059 | ADT | 3.1 | 161 | ETV1 | c.365G>A | p.5122N |
| chr01 | 45798063 | 1054 | ADT | 3.1 | 63 | MUTYH | c.788G>A | p.W263, |
| chr09 | 1.34E+08 | 1028 | ADT | 3.0 | 98 | NUP214 | c.6202T>G | p.F2068V |
| chr10 | 30727845 | 1104 | ADT | 2.9 | 102 | MAP3K8 | c.283A>C | p.D98A |
| chr03 | 10134970 | 1080 | ADT | 2.9 | 103 | FANCD2 | c.3851T>G | p.V1284G |
| chr03 | 1.56E+08 | 1098 | ADT | 2.9 | 100 | GMPS | c.1982T>G | p.V661G |
| chr22 | 29107898 | 1104 | ADT | 2.8 | 71 | CHEK2 | c.920C>T | p.A307V |
| chr22 | 41556647 | 1080 | ADT | 2.8 | 175 | EP300 | c.3592T>G | p.Y1198D |
| chr20 | 54958042 | 1054 | ADT | 2.8 | 142 | AURKA | c.565C>T | p.R189W |
| chr20 | 57484405 | 1028 | ADT | 2.8 | 142 | GNAS | c.2516A>C | p.D839A |
| chr09 | 1.24E+08 | 1050 | ADT | 2.8 | 107 | CNTRL | c.6956delA | p.E2319fs |
| chr01 | 10342447 | 1040 | ADT | 2.8 | 106 | KIF1B | c.1290delT | p.H430fs |
| chr15 | 66782841 | 1015 | ADT | 2.7 | 111 | MAP2K1 | c.1070T>G | p.V357G |
| chr15 | 67457234 | 1098 | ADT | 2.7 | 147 | SMAD3 | c.208T>G | p.S70A |
| chr09 | 1.34E+08 | 1040 | ADT | 2.7 | 108 | NUP214 | c.1924A>T | p.S642C |
| chr04 | 1941510 | 1028 | ADT | 2.7 | 73 | WHSC1 | c.1886_1888delAAT | p.K629_630delinsK |
| chr01 | 6194779 | 1028 | ADT | 2.7 | 219 | CHD5 | c.3011T>G | p.V1004G |
| chr13 | 48934263 | 1050 | ADT | 2.6 | 115 | RB1 | c.718A>T | p.K240. |
| chr05 | 56170860 | 1084 | ADT | 2.6 | 153 | MAP3K1 | c.1688T>G | p.V563G |
| chr17 | 57752063 | 1104 | ADT | 2.5 | 120 | CLTC | c.2423T>G | p.V808G |
| chr14 | 95572016 | 1080 | ADT | 2.5 | 78 | DICER1 | c.3092A>C | p.Q1031P |
| chr13 | 1.03E+08 | 1080 | ADT | 2.5 | 159 | BIVM | c.1238A>G | p.Q413R |
| chr12 | 416113 | 1040 | ADT | 2.5 | 155 | KDM5A | c.4073A>T | p.K1358M |
| chr11 | 1.08E+08 | 1080 | ADT | 2.5 | 118 | ATM | c.3578T>G | p.V1193G |
| chr03 | 1.56E+08 | 1084 | ADT | 2.5 | 158 | GMP5 | c.722T>G | p.V241G |
| chr02 | 2.13E+08 | 1028 | ADT | 2.5 | 240 | ERBB4 | c.1123G>A | p.G375R |
| chr17 | 78896525 | 1054 | ADT | 2.4 | 123 | RPTOR | c.2522C>A | p.A841D |
| chr16 | 16269767 | 1028 | ADT | 2.4 | 163 | ABCC6 | c.2325G>T | p.R775S |
| chr08 | 38275890 | 1080 | ADT | 2.4 | 123 | FGFR1 | c.1379T>G | p.V460G |
| chr06 | 1.18E+08 | 1104 | ADT | 2.4 | 163 | ROS1 | c.2495delA | p.K832fs |
| chr02 | 2.13E+08 | 1028 | ADT | 2.4 | 202 | ERBB4 | c.1488T>A | p.C496. |
| chr01 | 6185160 | 1084 | ADT | 2.4 | 122 | CHD5 | c.4394G>A | p.R1465K |
| chr01 | 1.71E+08 | 1017 | ADT | 2.4 | 121 | PRRX1 | c.419T>G | p.V140G |
| chr03 | 52436896 | 1080 | ADT | 2.3 | 84 | BAP1 | c.1951T>G | p.F651V |
| chr01 | 16247366 | 1104 | ADT | 2.3 | 128 | SPEN | c.1637T>G | p.V546G |
| chr19 | 15350204 | 1054 | ADT | 2.2 | 87 | BRD4 | c.3575delA | p.K1192fs |
| chr15 | 67457591 | 1080 | ADT | 2.2 | 174 | SMAD3 | c.401T>G | p.V134G |
| chr12 | 46211636 | 1084 | ADT | 2.2 | 89 | ARID2 | c.602C>A | p.T201N |
| chr09 | 1.34E+08 | 1084 | ADT | 2.2 | 88 | NUP214 | c.1705G>T | p.A569S |
| chr07 | 1.29E+08 | 1080 | ADT | 2.2 | 174 | SMO | c.1654T>G | p.L552V |
| chr03 | 10140501 | 1080 | ADT | 2.2 | 131 | FANCD2 | c.4283T>G | p.V1428G |

SUPPLEMENTARY TABLE 2-continued

Gene Mutations In Post-Treatment Patients.

| Chromosome | Position | Patient ID | Treatment | Mutant Allele Frequency % Post-Treatment | Depth | Gene name | DNA Change | Amino Acid Change |
|---|---|---|---|---|---|---|---|---|
| chr01 | 1.51E+08 | 1080 | ADT | 2.2 | 133 | SETDB1 | c.1268G>T | p.G423V |
| chr01 | 2.07E+08 | 1098 | ADT | 2.2 | 227 | IKBKE | c.1429T>G | p.F477V |
| chr12 | 4398008 | 1028 | ADT | 2.1 | 141 | CCND2 | c.572A>C | p.D191A |
| chr10 | 88991779 | 1098 | ADT | 2.1 | 138 | NUTM2A | c.1213T>G | p.F405V |
| chr10 | 1.03E+08 | 1054 | ADT | 2.1 | 137 | PAX2 | c.307T>G | p.Y103D |
| chr03 | 1.42E+08 | 1080 | ADT | 2.1 | 142 | ATR | c.6318delA | p.K210Gfs |
| chr22 | 29115384 | 1098 | ADT | 2.0 | 98 | CHEK2 | c.811A>G | p.S271G |
| chr16 | 2111872 | 1098 | ADT | 2.0 | 147 | TSC2 | c.1393A>C | p.T465P |
| chr14 | 74994051 | 1104 | ADT | 2.0 | 149 | LTBP2 | c.2387A>C | p.Q796P |
| chr06 | 1.18E+08 | 1054 | ADT | 2.0 | 146 | ROS1 | c.6134C>T | p.T2045M |
| chr01 | 45798358 | 1104 | ADT | 2.0 | 143 | MUTYH | c.578T>G | p.V193G |

Supplementary Table 3. Gene Mutations Shared Between Pre-Treatment And Post-Treatment Patients.

SUPPLEMENTARY TABLE 3

Gene Mutations Shared Between Pre-Treatment And Post-Treatment Patients.

| Chromosome | Position | Patient ID | Treatment | Mutant Allele Frequency % Pre-Treatment | Depth In Pre-Treatment | Mutant Allele Frequency % Post-Treatment | Depth IN Post-Treatment | Gene name | DNA Change | Amino Acid Change |
|---|---|---|---|---|---|---|---|---|---|---|
| chr10 | 81465798 | 1001 | Chemotherapy | 15.7 | 57 | 22.9 | 74 | NUTM2B | c.353C>T | p.A128V |
| chr23 | 70320535 | 1014 | Chemotherapy | 7.8 | 51 | 3.8 | 77 | FOXO4 | c.455A>C | p.N152T |
| chr16 | 16267139 | 1043 | Chemotherapy | 12.8 | 109 | 11.4 | 87 | ABCC6 | c.2917T>G | p..973E |
| chr15 | 99500291 | 1043 | Chemotherapy | 2.3 | 128 | 3.6 | 110 | IGF1R | c.3724T>G | p.F1242V |
| chr17 | 7578553 | 1028 | ADT | 2.7 | 145 | 2.4 | 125 | TP53 | c.377A>C | p.Y126V |
| chr06 | 168352869 | 1028 | ADT | 3.0 | 98 | 2.1 | 142 | MLLT4 | c.4766T>G | p.V1589G |
| chr17 | 5268418 | 1050 | ADT | 2.3 | 126 | 3.4 | 87 | RABEP1 | c.1670T>G | p.V557G |
| chr18 | 60985313 | 1059 | ADT | 2.0 | 149 | 2.3 | 130 | BCLZ | c.587T>G | p.V196G |
| chr01 | 164818578 | 1080 | ADT | 4.2 | 95 | 4.5 | 87 | PBX1 | c.1202A>C | p.H401P |
| chr02 | 25470026 | 1104 | ADT | 2.2 | 180 | 4.7 | 127 | DNMT3A | c.1016T>G | p.V339G |
| chr17 | 36874099 | 1104 | ADT | 4.8 | 165 | 2.8 | 107 | MLLT6 | c.1916T>G | p.V639G |

Supplementary Table 4. List of Mutated Genes in Different Treatment Status.

SUPPLEMENTARY TABLE S4

List of all mutated genes i different treatment status

| Pre-chemotherapy | post-chemotherapy | Pre-ADT | Post-ADT |
|---|---|---|---|
| NUTM2B | KDM6A | FOXO4 | SH3GL1 |
| FBXO11 | MTOR | PIK3CA | KRT17 |
| ARID1A | USP6 | ACSL6 | EP300 |
| MTOR | KRT17 | NDRG1 | PTK2 |
| TCF7L2 | ERCC3 | STK11 | PRDM16 |
| TOP1 | CRTC1 | MYH11 | PDGFRB |
| AKT1 | PTK2 | NBN | PTPN11 |
| KTN1 | CDKN2A | PHF6 | CNTRL |
| FCRL4 | APC | TLX1 | NSD1 |
| NUP214 | PBX1 | DNMT3A | STXBP2 |
| CSF1R | NUTM2A | LPP | DEK |
| PER1 | RET | FLCN | TPM4 |
| FLT1 | PRKAR1A | NOTCH1 | SF3B2 |
| SPEN | PTCH1 | PAX3 | TFEB |
| KDM6A | ROS1 | RABEP1 | KIF1B |
| PAX8 | NTRK1 | AFF3 | BAP1 |
| FBXW7 | KTN1 | NUP214 | CREB1 |
| MLH1 | SMARCB1 | RALGDS | CBL |
| PCSK7 | SETD2 | UTY | MED12 |
| PBX1 | NSD1 | ATR | HSP90AB1 |
| NSD1 | EPHB6 | ARID5B | CNBP |
| FLCN | TPR | CRTC3 | PAX7 |
| FANCA | ELAC2 | ATM | ALDH2 |
| MLLT4 | PLK1 | GUCY1A2 | ETV1 |
| NPM1 | PBRM1 | IKBKE | MUTYH |
| ATIC | IKBKE | TNFRSF14 | NUP214 |
| TPM3 | MED12 | TRIM27 | MAP3K8 |
| NUMA1 | MAP3K1 | CCNE1 | FANCD2 |
| SMARCA4 | AKAP9 | PMS1 | GMPS |
| TPM4 | SF382 | AIP | CHEK2 |
| DAXX | NFIB | LRP5 | AURKA |
| CHD6 | DNMT3A | KMT2A | GNAS |
| PML | STXBP2 | FNBP1 | MAP2K1 |
| ROS1 | CBLC | LASP1 | SMAD3 |
| ERCC3 | NFKB2 | TET1 | WHSC1 |
| TP53 | CHCHD7 | FANCA | CHD5 |
| HNRNPA2B1 | KIF18 | IGF1R | RB1 |
| CIITA | NUP214 | CREB1 | MAP3K1 |
| STXBP2 | NOTCH1 | RAD51B | CLTC |
| NF1 | PAX7 | ARID5A | DICER1 |
| FGFR1 | PATZ1 | PRDM16 | BIVM |
| CBL | ABCC6 | SH3GL1 | KDM5A |
| WHSC1 | PAX2 | CCND2 | ATM |
| MKL1 | WHSC1 | P8RM1 | ERBB4 |

SUPPLEMENTARY TABLE S4-continued

List of all mutated genes i different treatment status

| Pre-chemotherapy | post-chemotherapy | Pre-ADT | Post-ADT |
|---|---|---|---|
| DDIT3 | PRKDC | ARID3B | RPTOR |
| GLMN | PCSK7 | CBLC | ABCC6 |
| FGFR1OP | FNBP1 | CNTRL | FGFR1 |
| DNMT3A | PRDM1 | NF1 | ROS1 |
| CHEK2 | EPHA6 | RET | PRRX1 |
| FOXO4 | ETV5 | EIF4A2 | SPEN |
| ABCC6 | PER1 | GAS7 | BRD4 |
| IGF1R | ASPSCR1 | NIN | ARID2 |
|  | FANCG | MYB | SMO |
|  | NCKIPSD | ERCC1 | SETDB1 |
|  | EPHA10 | PTCH1 | IKBKE |
|  | MKL1 | ERCC5 | CCND2 |
|  | NTRK2 | BIVM-ERCC5 | NUTM2A |
|  | PTK2B | WHSC1 | PAX2 |
|  | KDR | SUZ12 | ATR |
|  | PDE4DIP | MLLT6 | TSC2 |
|  | NUTM2B | ASP5CR1 | LTBP2 |
|  | FOXO4 | CHEK1 | TP53 |
|  | IGF1R | TP53 | MLLT4 |
|  |  | MLLT4 | RABEP1 |
|  |  | BCL2 | BCL2 |
|  |  | PBX1 | PBK1 |
|  |  |  | DNMT3A |
|  |  |  | MLLT5 |

Supplementary Table 5. Primer List And PCR.

SUPPLEMENTARY TABLE S5

Primer list and PCR conditions

| GENES | POSITION | PRIMERS | SEQUENCES | Tm | PRODUCT (bp) | PATIENT ID | Treatment Type | Treatment Status | VALIDATED |
|---|---|---|---|---|---|---|---|---|---|
| NUTM23 | R1455798 | Forward Primer | 5'-TCA TAC GCC CTT AGC TGT TGG-3' SEQ ID NO: 1 | 68 | 119 | 1001 | Chemo-therapy | Pre | Yes |
| | | Reverse Primer (mutant) | 5'-CGG TCC CAG CAC TGG GTA TA-3' SEQ ID NO: 2 | | | 1001 | Chemo-therapy | Post | Yes |
| | | Reverse Primer (wild type) | 5'-CGG TCC CAG CAC TGG GTA TG-3' SEQ ID NO: 3 | | | 1043 | Chemo-therapy | Pre | Yes |
| ABCC6 | 16267139 | Forward Primer | 5'-CCT CTG GAT GAC CCT GAC A-3' SEQ ID NO: 4 | 64 | 84 | 1043 | Chemo-therapy | Pre | Yes |
| | | Reverse Primer (mutant) | 5'-GTG GGT GAA GCT GGT GGT TC-3' SEQ ID NO: 5 | | | 1043 | Chemo-therapy | Post | Yes |
| | | Reverse Primer (wild type) | 5'-GTG GGT GAA GCT GGT GGT TA-3' SEQ ID NO: 6 | | | | | | |
| MILT4 | 165352869 | Forward Primer | 5'-ATG GGA AAC ACG CAG AAG C-3' SEQ ID NO: 7 | Uncertain | 83 | 1028 | ADT | Pre | Uncertain |
| | | Reverse Primer (mutant) | 5'-CTG AAC GAA GAG CGA GGG G-3' SEQ ID NO: 8 | | | 1028 | ADT | Post | Uncertain |
| | | Reverse Primer (wild type) | 5'-CTG AAC GAA GAG CGA GGG T-3' SEQ ID NO: 9 | | | | | | |
| PDX1 | 164818578 | Forward Primer | 5'-CTC AGT GTT CTC CTG CTT CG-3' SEQ ID NO: 10 | 52 | 122 | 1080 | ADT | Pre | Yes |
| | | Reverse Primer (mutant) | 5'-ACT TAG TCT TCT CTA TAC CCA GCC-3' SEQ ID NO: 11 | | | 1080 | ADT | Post | Yes |
| | | Reverse Primer (wildtype) | 5'-ACT TAG TCT TCT CTA TAC CCA GCA-3' SEQ ID NO: 12 | | | | | | |
| DNMT3A | 25470020 | Forward Primer | 5'-GCA AGG CAT GGG GTG GGT-3' SEQ ID NO: 13 | 61 | 89 | 1104 | ADT | Pre | Uncertain |
| | | Reverse Primer (mutant) | 5'-GGC ATC AGC TTC TCA ACA CAC C-3' SEQ ID NO: 14 | | | 1104 | ADT | Post | Yes |
| | | Reverse Primer (wild type) | 5'-GGC ATC AGC TTC TCA ACA CAC A-3' SEQ ID NO: 15 | | | | | | |
| FBXD11 | 48040930 | Forward Primer | 5'-AAC CCC AAA ATT AGA CGC A-3' SEQ ID NO: 16 | Uncertain | 91 | 1001 | Chemo-therapy | Pre | Uncertain |
| | | Reverse Primer (mutant) | 5'-AAA AAG ATG ACA GAT TAA ACA TAC T-3' SEQ ID NO: 17 | | | | | | |
| | | Reverse Primer (wild type) | 5'-AAA AAG ATG ACA GAT TAA ACA TAC C-3' SEQ ID NO: 18 | | | | | | |
| ACSL6 | 131325794 | Forward Primer | 5'-TGC CCA CAT CCC TCC CTA C-3' SEQ ID NO: 19 | Uncertain | 99 | 1080 | ADT | Pre | Uncertain |
| | | Reverse Primer (mutant) | 5'-CAG TGG CTG TCC TAC CAG GG-3' SEQ ID NO: 20 | | | | | | |

SUPPLEMENTARY TABLE S5-continued

Primer list and PCR conditions

| GENES | POSITION | PRIMERS | SEQUENCES | Tm | PRODUCT (bp) | PATIENT ID | Treatment Type | Treatment Status | VALIDATED |
|---|---|---|---|---|---|---|---|---|---|
| | | Reverse Primer (wild type) | 5'-CAG TGG CTG TCC TAC CAG GA-3' SEQ ID NO: 21 | | | | | | |
| TCF7L2 | 114711242 | Forward Primer | 5'-CCC TCG GGG CAC TTT CTA A-3' SEQ ID NO: 22 | 61 | 106 | 1002 | Chemo-therapy | Pre | Yes |
| | | Reverse Primer (mutant) | 5'-TCC ATC TTG CCT CTT GGC CA-3' SEQ ID NO: 23 | | | | | | |
| | | Reverse Primer (wild type) | 5'-TCC ATC TTG CCT CTT GGC CG-3' SEQ ID NO: 24 | | | | | | |
| CSF1R | 149437063 | Forward Primer | 5'-GGT GGG AAG AGG CGT CAG-3' SEQ ID NO: 25 | 66 | 139 | 1002 | Chemo-therapy | Pre | Yes |
| | | Reverse Primer (mutant) | 5'-CAA ATG ACT CCT TCT CTG AGC-AT-3' SEQ ID NO: 26 | | | | | | |
| | | Reverse Primer (wild type) | 5'-CAA ATG ACT CCT TCT CTG AGC AA-3' SEQ ID NO: 27 | | | | | | |
| PLT1 | 28979918 | Forward Primer | 5'-ATA AAC CTA GAA TTG GGA GCT G-3' SEQ ID NO: 28 | 59 | 99 | 1002 | Chemo-therapy | Pre | Yes |
| | | Reverse Primer (mutant) | 5'-TGG CAA TAA TAG AAG GAA AGA ATA G-3' SEQ ID NO: 29 | | | | | | |
| | | Reverse Primer (wild type) | 5'-TGG CAA TAA TAG AAG GAA AGA ATA A-3' SEQ ID NO: 30 | | | | | | |
| MILT4 | 168291542 | Forward Primer | 5'-GCC ATC CTG ACC AAC CTG A-3' SEQ ID NO: 31 | Uncertain | 81 | 1001 | Chemo-therapy | Pre | Uncertain |
| | | Reverse Primer (mutant) | 5'-TCT CTT CAA CTG AAA GAC TAA AAT CA-3' SEQ ID NO: 32 | | | | | | |
| | | Reverse Primer (wild type) | 5'-TCT CTT CAA CTG AAA GAC TAA AAT CC-3' SEQ ID NO: 33 | | | | | | |
| LRP5 | 68177382 | Forward Primer | 5'-TGC CCA TCC AGT CAA CGG-3' SEQ ID NO: 34 | 61 | 115 | 1028 | ADT | Pre | Yes |
| | | Reverse Primer (mutant) | 5'-CTC CTC ACC TGC TGC CAG C-3' SEQ ID NO: 35 | | | | | | |
| | | Reverse Primer (wild type) | 5'-CTC CTC ACC TGC TGC CAG A-3 SEQ ID NO: 36 | | | 1098 | ADT | Pre | Yes |
| ACT1 | 100239425 | Forward Primer | 5'-TCC CGG ACA CCC CTT GAT G-3' SEQ ID NO: 37 | Uncertain | 72 | 1005 | Chemo-therapy | Pre | Uncertain |
| | | Reverse Primer (mutant) | 5'-CCG TAG TCA TTG TCC TCC AGC AT-3' SEQ ID NO: 38 | | | 1017 | Chemo-therapy | Post | Uncertain |
| | | Reverse Primer (wild type) | 5'-CCG TAG TCA TTG TCC TCC AGC AC-3 SEQ ID NO: 39 | | | | | | |

SUPPLEMENTARY TABLE S5-continued

Primer list and PCR conditions

| GENES | POSITION | PRIMERS | SEQUENCES | Tm | PRODUCT (bp) | PATIENT ID | Treatment Type | Treatment Status | VALIDATED |
|---|---|---|---|---|---|---|---|---|---|
| NUP214 | 134015937 | Forward Primer | 5'-ATG TTG AGG GCA GTC TTT G-3' SEQ ID NO: 40 | 56 | 103 | 1002 | Chemo-therapy | Pre | Yes |
| | | Reverse Primer (mutant) | 5'-GGA GGA AGA GTC TTT TCA TCC-3' SEQ ID NO: 41 | | | | | | |
| | | Reverse Primer (wild type) | 5'-GGA AGA AGA GTC TTT TCA TCA-3' SEQ ID NO: 42 | | | | | | |
| EP303 | 41531818 | Forward Primer | 5'-TTG TAT GGT GGC TGT TGT ATT TAT T-3' SEQ ID NO: 43 | 63 | 80 | 1028 | ADT | Pre | Yes |
| | | Reverse Primer (mutant) | 5'-CCA TTT ACT CCC ATA GGA CTA GCC-3' SEQ ID NO: 44 | | | | | | |
| | | Reverse Primer (wild type) | 5'-CCA TTT ACT CCC ATA GGA CTA GCA-3' SEQ ID NO: 45 | | | | | | |
| PTK2 | 141900642 | Forward Primer | 5'-TAT GAA AAG TCC CCG ATA AGT T-3' SEQ ID NO: 46 | 62 | 139 | 1028 | ADT | Post | Yes |
| | | Reverse Primer (mutant) | 5'-CAT GGA GAT GCT ACT GAT GTC AA-3' SEQ ID NO: 47 | | | | | | |
| | | Reverse Primer (wild type) | 5'-CAT GGA GAT GCT ACT GAT GTC AG-3' SEQ ID NO: 48 | | | | | | |
| PTK2 | 141716119 | Forward Primer | 5'-ATG CAC AAT GTA CCG CTC TAC C-3' SEQ ID NO: 49 | 63 | 97 | 1080 | ADT | Post | Yes |
| | | Reverse Primer (mutant) | 5'-GCA CAT GGT ACA AAC CAA TCA GG-3' SEQ ID NO: 50 | | | | | | |
| | | Reverse Primer N/A (wild type) | | | | | | | |
| PFKAB5A | 66523982 | Forward Primer | 5'-ATT CCA TAG CAT TAT GTG GTG AT-3' SEQ ID NO: 51 | 52 | 91 | 1002 | Chemo-therapy | Post | Yes |
| | | Reverse Primer (mutant) | 5'-TTC CGC TTT CTC AGT GTG CTT A-3' SEQ ID NO: 52 | | | | | | |
| | | Reverse Primer (wild type) | 5'-TTC CGC TTT CTC AGT GTG CTT C-3' SEQ ID NO: 53 | | | | | | |
| RO51 | 117642422 | Forward Primer | 5'-TAC TGT TGC CCA CCC TTT GC-3' SEQ ID NO: 54 | 67 | 77 | 1005 | Chemo-therapy | Post | Yes |
| | | Reverse Primer (mutant) | 5'-CTA ATG CCT GCT ATG CAA TAC G-3' SEQ ID NO: 55 | | | | | | |
| | | Reverse Primer (wild type) | 5'-CTA ATG CCT GCT ATG CAA TAC A-3' SEQ ID NO: 56 | | | | | | |
| SMARC31 | 24143268 | Forward Primer | 5'-CTC CCA CCA CTT AGA TGC CGT-3' SEQ ID NO: 57 | Uncertain | 106 | 1017 | Chemo-therapy | Post | Uncertain |
| | | Reverse Primer (mutant) | 5'-TGC AGC GAT GCA TCC ACA CA-3' SEQ ID NO: 58 | | | | | | |
| | | Reverse Primer (wild type) | 5'-TGC AGC GAT GCA TCC ACA CC-3' SEQ ID NO: 59 | | | | | | |

SUPPLEMENTARY TABLE S5-continued

Primer list and PCR conditions

| GENES | POSITION | PRIMERS | SEQUENCES | Tm | PRODUCT (bp) | PATIENT ID | Treatment Type | Treatment Status | VALIDATED |
|---|---|---|---|---|---|---|---|---|---|
| ABCC6 | 16269767 | Forward Primer | 5'-GCC TAA GTG CCC GAG ATG C-3'  SEQ ID NO: 60 | 67 | 106 | 1028 | ADT | Post | Yes |
| | | Reverse Primer (mutant) | 5'-CCG AGC TTA GAC GCG AGA GT-3'  SEQ ID NO: 61 | | | | | | |
| | | Reverse Primer (wild type) | 5'-CCG AGC TTA GAC GCG AGA GG-3'  SEQ ID NO: 62 | | | | | | |
| PLK1 | 23693386 | Forward Primer | 5'-GGG TTG TGG CTG GGA GAC TG-3'  SEQ ID NO: 63 | 67 | 74 | 1001 | Chemo-therapy | Post | Yes |
| | | Reverse Primer (mutant) | 5'-TGG TTT GCC CAC TAA CAA GGT ATC-3'  SEQ ID NO: 64 | | | 1043 | Chemo-therapy | Post | Yes |
| | | Reverse Primer (wild type) | 5'-TGG TTT GCC CAC TAA CAA GGT ATA-3'  SEQ ID NO: 65 | | | | | | |
| ERCC3 | 128017023 | Forward Primer | 5'-GGA CCC AGG AGA AGG CAG AG-3  SEQ ID NO: 66 | 68 | 96 | 1001 | Chemo-therapy | Post | Yes |
| | | Reverse Primer (mutant) | 5'-GCC AGC GAG TTT CGT GAT CC-3'  SEQ ID NO: 67 | | | 1017 | Chemo-therapy | Post | Yes |
| | | Reverse Primer (wild type) | 5'-GCC AGC GAG TTT CGT GAT CA-3'  SEQ ID NO: 68 | | | | | | |
| EPH86 | 142561389 | Forward Primer | 5'-CCA AGG GAT TCA GGT TCA GA-3'  SEQ ID NO: 69 | 59 | 121 | 1003 | Chemo-therapy | Post | Yes |
| | | Reverse Primer (mutant) | 5'-CCC TCT TAT TTC TGG GCA GG-3'  SEQ ID NO: 70 | | | 1017 | Chemo-therapy | Post | Yes |
| | | Reverse Primer (wild type) | 5'-CCC TCT TAT TTC TGG GCA GA-3'  SEQ ID NO: 71 | | | | | | |
| MED12 | 70354208 | Forward Primer | 5'-ACT CCG TGG TCT GCT GGG TGC T-3'  SEQ ID NO: 72 | 61 | 70 | 1010 | Chemo-therapy | Post | Yes |
| | | Reverse Primer (mutant) | 5'-TTG TTG TGG CCC TGG CAG GG-3'  SEQ ID NO: 73 | | | 1043 | Chemo-therapy | Post | Yes |
| | | Reverse Primer (wild type) | 5'-TTG TTG TGG CCC TGG CAG GT-3'  SEQ ID NO: 74 | | | 1098 | ADT | Post | Yes |
| CRTC1 | 18858533 | Forward Primer | 5'-CAC GCT CCC GGT ACA CCC TG-3'  SEQ ID NO: 75 | 58 | 101 | 1001 | Chemo-therapy | Post | Yes |
| | | Reverse Primer (mutant) | 5'-CCA TCT CCT CCT CCC CCA GC-3'  SEQ ID NO: 76 | | | 1017 | Chemo-therapy | Post | Yes |
| | | Reverse Primer (wild type) | 5'-CCA TCT CCT CCT CCC CCA GA-3'  SEQ ID NO: 77 | | | | | | |

E. Summary.

Cancer is characterized by massive genomic abnormalities, some of which are targets for therapy or are used for monitoring response to specific treatments. Recent studies have reported that genomic abnormalities in cfDNA resemble genomic signatures of primary tumors in human cancers (Crowley, et al., "Liquid Biopsy: Monitoring Cancer-Genetics in the Blood." *Nat Rev Clin Oncol*, 10:472-484 2013; Diaz and Bardelli, "Liquid Biopsies: Genotyping Circulating Tumor DNA." *J Clin Oncol*, 32:579-586 2014; Farris and Trimarchi, "Plasma-Seq: A Novel Strategy for Metastatic Prostate Cancer Analysis." *Genome Med*, 5:35 2013; Heitzer, et al., "Tumor-Associated Copy Number Changes in the Circulation of Patients with Prostate Cancer Identified through Whole-Genome Sequencing." *Genome Med*, 5:30 2013). In this study, we examined plasma cfDNAs in advanced prostate cancer and were able to detect somatic mutations and genomic aberrations in the patient groups after accounting for constitutional genomic abnormalities. These aberrations were often different between pre- and post-treatment, reflecting dynamic genomic evolution during stage-specific therapies.

Our results suggest that somatic alterations in cfDNA may serve as sensitive biomarkers for predicting treatment response and clinical outcome in advanced prostate cancer. To examine the repertoire of genomic aberrations in tumor tissues, biopsies are often performed. However, tissue biopsy in advanced prostate cancer is challenging because bone metastasis are predominant. Many patients do not have residual disease at their primary site due to surgical removal of the prostate. Biopsies at sites of bone or nodal metastasis are invasive, morbid, and inaccurate. These biopsies are subject to sampling bias and may not represent the overall tumor mass. Due to these limitations, liquid biopsy by sensitive detection of tumor components has emerged as an attractive alternative option. This approach is minimally invasive and can be more frequently scheduled in clinical laboratories. Because blood stream contains the cfDNAs derived from the tumor sites, the liquid biopsy assay may detect more complete repertoire of tumor genome variations (Chan, et al., "Cancer Genome Scanning in Plasma: Detection of Tumor-Associated Copy Number Aberrations, Single-Nucleotide Variants, and Tumoral Heterogeneity by Massively Parallel Sequencing." *Clin Chem*, 59:211-224 2013; Crowley, et al., "Liquid Biopsy: Monitoring Cancer-Genetics in the Blood." *Nat Rev Clin Oncol*, 10:472-484 2013; Diaz and Bardelli, "Liquid Biopsies: Genotyping Circulating Tumor DNA." *J Clin Oncol*, 32:579-586 2014; Farris and Trimarchi, "Plasma-Seq: A Novel Strategy for Metastatic Prostate Cancer Analysis." *Genome Med*, 5:35 2013; Heitzer, et al., "Tumor-Associated Copy Number Changes in the Circulation of Patients with Prostate Cancer Identified through Whole-Genome Sequencing." *Genome Med*, 5:30 2013).

It was shown that tumor genomic abnormalities were well reflected in cfDNA during cancer progression (Heitzer, et al., "Tumor-Associated Copy Number Changes in the Circulation of Patients with Prostate Cancer Identified through Whole-Genome Sequencing." *Genome Med*, 5:30 2013; Leary, et al., "Detection of Chromosomal Alterations in the Circulation of Cancer Patients with Whole-Genome Sequencing." *Sci Transl Med*, 4:162ra154 2012). By comparing the differences between multiregional sequencing of 2 synchronous cancer tissues and shotgun sequencing of cfDNA, Chan, et al., (Chan, et al., "Cancer Genome Scanning in Plasma: Detection of Tumor-Associated Copy Number Aberrations, Single-Nucleotide Variants, and Tumoral Heterogeneity by Massively Parallel Sequencing." *Clin Chem*, 59:211-224 2013), show that cfDNA sequencing is able to detect genomic variations originated from different tumor sites. Recently, Schutz, et al. (Schutz, et al., "Chromosomal Instability in Cell-Free DNA Is a Serum Biomarker for Prostate Cancer." *Clin Chem*, 61:239-248 2015), found that cfDNA genomic variations are able to distinguish both benign prostatic hypertrophy and prostatitis from prostate cancer with accuracy of 90%. Clearly, liquid biopsy may provide a useful tool for cancer detection, monitoring and research.

To estimate tumor DNA content, previous studies applied "genomewide z-score" (Leary, et al., "Detection of Chromosomal Alterations in the Circulation of Cancer Patients with Whole-Genome Sequencing." *Sci Transl Med*, 4:162ra154 2012) or "PA-score" (Heitzer, et al., "Tumor-Associated Copy Number Changes in the Circulation of Patients with Prostate Cancer Identified through Whole-Genome Sequencing." *Genome Med*, 5:30 2013). However, these algorithms may not accurately reflect tumor DNA contribution to cfDNA because tumor genomes are not always altered in the genome segments.

In addition, calculations of these scores require cfDNAs derived from a group of normal individuals as reference controls. Due to the germline-determined CNVs pre-existing in any given individual, these algorithms may generate significant bias toward the regions with pre-existing CNVs. To address this issue, we normalized cfDNA read counts using lymphocyte gDNA read counts from the same patient, significantly minimizing the biases caused by pre-existing CNVs. Additionally, we developed the PGA scoring system by summing the most significant genomic regions, avoiding potential background noises from other scoring algorithms. Our data show that PGA scores and TEff indexes are potentially useful to assess treatment response and overall survival.

Targeted sequencing in cfDNA has demonstrated potential clinical utility in guiding selection of targeted therapies (Narayan, et al., "Ultrasensitive Measurement of Hotspot Mutations in Tumor DNA in Blood Using Error-Suppressed Multiplexed Deep Sequencing." *Cancer Res*, 72:3492-3498 2012). By analyzing mutational profiles before and after initiating ADT, we were able to detect increased mutant genes after approximately 4 months of ADT in several pathways, including protein kinase A signaling, the PPARα/RXRα activation and GNRH signaling pathways. These pathways are associated with AR activation (Nazareth and Weigel, "Activation of the Human Androgen Receptor through a Protein Kinase a Signaling Pathway." *J Biol Chem*, 271:19900-19907 1996) and androgen biosynthesis (Limonta and Manea, "Gonadotropin-Releasing Hormone Receptors as Molecular Therapeutic Targets in Prostate Cancer: Current Options and Emerging Strategies." *Cancer Treat Rev*, 39:647-663 2013). One mutated gene in these pathways is EP300, a gene for prostate cancer cell proliferation (Heemers, et al., "Androgen Deprivation Increases P300 Expression in Prostate Cancer Cells." *Cancer Res*, 67:3422-3430 2007) and hormone responsiveness of AR (Choi, et al., "Procyanidin B3, an Inhibitor of Histone Acetyltransferase, Enhances the Action of Antagonist for Prostate Cancer Cells Via Inhibition of P300-Dependent Acetylation of Androgen Receptor." *Biochem J*, 433:235-244 2011). We also found more gene mutations in the glucocorticoid receptor (GR) signaling pathway after ADT. GR expression is stimulated by castration therapy, a mechanism that compensates for AR signaling blockade and promotes CRPC progression (Arora, et al., "Glucocorticoid Receptor Confers Resistance to Antiandrogens by Bypassing Androgen Receptor Blockade." *Cell*, 155:1309-1322 2013; Xie, et al., "The Expression of Glucocorticoid Receptor Is Negatively Regulated by Active Androgen Receptor Signaling in Prostate Tumors." *Int J Cancer*, 136:E27-38 2014). Currently, preclinical models are often used to define the mechanisms of resistance to a specific treatment, but it is generally difficult to confirm these findings in clinical samples. Our results suggest that the cfDNA-based genetic analysis described herein, provide a superior approach for studying and predicting tumor resistance in real patient samples.

Many mutations detected after treatments were not present in pre-treatment samples. These non-overlapping mutations are of interest as they may provide novel insights into the evolution of tumor genomes in response to therapy or serve as predictive biomarker for treatment response and/or prognostic biomarkers for survival. For example, mutations in PRKAR1A and NFKB2 were found after chemotherapy treatment. PRKAR1A is functionally linked to AR during the progression of prostate cancer (Sarwar, et al., "Protein Kinase A (PKA) Pathway Is Functionally Linked to Androgen Receptor (AR) in the Progression of Prostate Cancer." *Urol Oncol*, 32:25 e21-12 2014). Its overexpression is observed in advanced prostate cancer (Merkle and Hoffmann, "Roles of cAMP and cAMP-Dependent Protein Kinase in the Progression of Prostate Cancer: Cross-Talk with the Androgen Receptor." *Cell Signal*, 23:507-515 2011; Sarwar, et al., "Protein Kinase A (PKA) Pathway Is Functionally Linked to Androgen Receptor (Ar) in the Progression of Prostate Cancer." *Urol Oncol*, 32:25 e21-12 2014) and may cause resistance to chemotherapy (Loilome, et al., "Prkar1a Is Overexpressed and Represents a Possible Therapeutic Target in Human Cholangiocarcinoma." *Int J Cancer*, 129:34-44 2011). NFKB can be activated by the chemotherapy drug (docetaxel) and contributes to treatment resistance in prostate cancer (Codony-Servat, et al., "Nuclear Factor-Kappa B and Interleukin-6 Related Docetaxel Resistance in Castration-Resistant Prostate Cancer." *Prostate*, 73:512-521 2013; Marin-Aguilera, et al., "Epithelial-to-Mesenchymal Transition Mediates Docetaxel Resistance and High Risk of Relapse in Prostate Cancer." *Mol Cancer Ther*, 13:1270-1284 2014; O'Neill, et al., "Characterisation and Manipulation of Docetaxel Resistant Prostate Cancer Cell Lines." *Mol Cancer*, 10:126 2011). These results are consistent with the common notion that stage-specific therapies increase tumor cell subpopulations carrying treatment-resistant mutations and proportionally reduce cell subpopulations carrying treatment-sensitive mutations.

In summary, next generation sequencing was used to test cfDNAs for somatic variations in advanced prostate cancer. We developed a new scoring algorithm to estimate tumor DNA burden and predict patient's response to a specific therapy. We found that genetic and genomic profile changes after treatments are clinically and biologically associated with response to stage-specific therapies. Although the study examined a limited number of patients, the results from this study strongly support that DNA-based liquid biopsy has great potential to serve as alternative means to examine tumor genetic changes in advanced prostate cancer. Further studies are needed to evaluate the clinical utility of cfDNA as useful biomarker to predict treatment response and clinical outcomes.

F. Materials And Methods.

The following are exemplary materials and methods used during the development of the present inventions.

1. Sample Collection.

Plasma specimens from two separate cohorts of advanced prostate cancer patients were randomly selected from a hospital-based registry for biomarker development in advanced prostate cancer. Details of patient enrollment have been previously reported (Huang, et al., "Exosomal Mir-1290 and Mir-375 as Prognostic Markers in Castration-Resistant Prostate Cancer." *Eur Urol*, 67:33-41 2015). The plasma was derived from EDTA-treated blood. Plasma was separated within 2 hours after blood draw and frozen immediately at −80° C. without a freeze-thaw cycle before use. Patient characteristics are presented in Table 1. Each patient provided plasma collected just before treatment and plasma collected approximately four months after initiating stage-specific therapy. The treatments were initiated after collection of the first specimen. Castration levels of testosterone (total testosterone <50 ng/dl) were confirmed at the time of the second sample collection. This study was approved by Institutional Review Boards at both the Medical College of Wisconsin and Mayo Clinic.

2. DNA Extraction And Sequencing Library Preparation.

Blood plasma samples underwent a second centrifugation at 3000 rpm for 10 min before DNA extraction. The cfDNAs were extracted from 400-800 μl of plasma using QIAamp DNA Blood Mini Kit (QIAGEN, Valencia, Calif., USA). The final DNA eluent (50 μl) was quantified by a Qubit 2.0 Fluorometer (Life Technology, Carlsbad, Calif., USA) and stored at −80° C. until use. DNA libraries were prepared using a NEXTflex DNA-Seq Kit (BIOO Scientific Corporation, Austin, Tex., USA). Libraries were pooled for paired-end sequencing on a HiSeq2000 Sequencing System (Illumina, San Diego, Calif., USA).

3. CNV Calculation.

Raw sequencing data (fastq files) were first mapped to the human genome (hg19) (DNASTAR, Madison, Wis.). Read counts from the mapped sequence files were then binned into 1 Mb windows (total 3113 genomic bins) and adjusted to the global mean count for each sample. The read count ratio in each genomic bin was calculated by comparing cfDNA to lymphocyte gDNA derived from the same patient to account for constitutional CNVs. The resulting ratios were further log 2 transformed and corrected for GC content (Diskin, et al., "Adjustment of Genomic Waves in Signal Intensities from Whole-Genome Snp Genotyping Platforms." *Nucleic Acids Res*, 36:e126 2008). The fully normalized log 2 ratios in genomic bins were subjected to segmentation using the copy number analysis method (CNAM) algorithm (Golden Helix, Bozeman, Mont.).

4. PGA Score And TEff Index.

Figure 9:
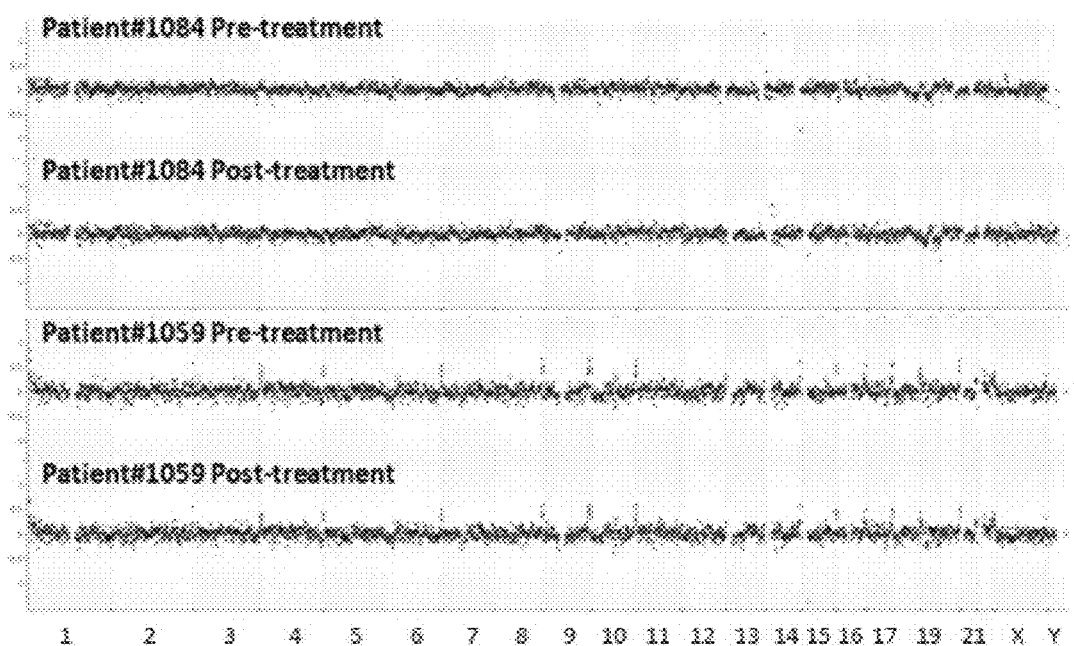
FIG. 9: shows exemplary extensive CNVs at telomere and centromere regions in patient #1059. Chromosomes were shown on the x-axis while GC-adjusted log 2 ratios (black dots) in 1 Mb windows were on the y-axis. Red lines indicate the trend of copy number variations. Extensive CNV at telomere and centromere regions were clearly observed in samples from patient #1059 but not in patient #1084.

To quantify the genomic abnormality and facilitate comparison between different samples, we defined the ith percentile of absolute log 2 ratios (ALRs) as ALR.i and calculated the sum of the squared ALRs between ALR.95 and ALR.99, where ALR.95 was considered as the minimum threshold of genomic abnormality. We named this summed value "Plasma Genomic Abnormality (PGA) score". A higher score indicates greater tumor DNA fraction in the cfDNA. The top one percentile ALRs were excluded to avoid over-estimation of genomic abnormalities because some samples showed extensive CNVs at telomere or centromere regions (FIG. 9). Although we did not exclude possibility of true CNV changes (for example, gene amplification), we believe that the extreme CNV changes in the regions were more likely caused by high sequence homologs and relatively low quality sequencing libraries. To quantify treatment response in each patient, we defined the TEff (Treatment Efficacy) index as the log 2 ratio of PGA scores between the pre- and post-treatments: TEff index=log 2(prePGA/postPGA)×10. A TEff index of less than or close to zero indicates no response to treatment while a higher TEff index is indicative of a better treatment response.

5. Targeted Sequencing.

The Comprehensive Cancer Panel (Roche NimbleGen, Madison, Wis.) was used for targeted sequencing. The panel covers 4 Mb genomic sequences and targets 578 cancer-related genes. The genes were captured from sequencing libraries made for CNV analysis according to Roche NimbleGen's manual. Final enriched libraries were subjected to 100 bp PE sequencing on a HiSeq2000 Sequencing System. Gene mutations were detected by comparing cfDNA to lymphocyte gDNA in the same patient with 2% variant alleles as the cutoff for mutation calls. HMGC Sequencing Core at Medical College of Wisconsin provided DNA sequencing service and Great Lakes Genomics Center for provided the computational resources.

6. Allele Specific PCR.

Allele specific PCR (AS-PCR) was used to validate sequencing-detected mutations. For each mutation, three primers were designed with one common primer and two mutant-specific primers. Reactions were performed in a 25 µl reaction with 4 ng of pre-amplified DNA and 0.5 unit of Taq DNA polymerase (New England Biolab, Ipswich, Mass.). This DNA polymerase does not have 3'-5' exonuclease activity and therefore is suitable for AS-PCR. Amplifications were carried out in a thermal cycler (Eppendorf Mastercycler pro S) including initial denaturation for 60 sec at 95° C., 40 cycles of denaturation for 30 sec at 95° C., annealing for 30 sec at primer-dependent temperatures (Supplementary Table S5), and extension for 40 sec at 72° C.

7. Mutation Pathway Enrichment Analysis.

To examine the functional classifications of mutant genes, we applied Ingenuity Pathway Analysis (IPA, Qiagen, Calif.) and treated the 578 cancer-related genes as background reference. For mutant genes, we searched for mutational profile differences between pre- and post-treatment samples. We defined >3 gene differences in a specific pathway between pre- and post-treatments as the cutoff for mutational profile changes. This analysis was useful to determine pathways that respond to stage-specific therapy.

II. Genomic Abnormality of Urine Cell Free DNA and Plasma Cell Free DNA as Biomarkers in Advanced Prostate Cancer: Based Upon 10 Prostate Tumor Associated Genes.

The following describes the development of an exemplary predictive Urine Genomic Abnormality (10-UGA) scores and Plasma Genomic Abnormality (10-PGA) scores based upon analysis of 10 genes isolated from cell-free DNA from both urine and blood samples collected from a set of prostate cancer patients. The 10 genes used in this exemplary analysis are: AR, MYC, CHD1, PTEN, RB1, TP53, ZBTB16, CCND1, PIK3CA/B and TMPRSS2-ERG. Additionally, observations of genetic abnormities discovered in the patient's cell-free DNA samples are shown.

A. Overview of Genetic Profiling of Urine Cell Free DNA (cfDNA) Biomarkers.

Genetic profiling of urine cell free DNA (cfDNA) biomarkers was evaluated in advanced prostate cancer during the development of the present inventions. As described herein, urine samples collected immediately before and 3 months after initiating androgen deprivation therapy for nine HSPC patients and docetaxel chemotherapy for ten CRPC patients were analyzed. This patient set is within the set used for the total genomic analysis described in section I. We performed whole genome sequencing of urine cfDNAs to detect tumor-associated genomic abnormalities. Our log 2 ratio-based copy number analysis showed common genomic abnormalities of prostate cancer including AR amplification in 5/10 CRPC patients. Other abnormalities were also detected such as TMPRSS2-ERG fusion, PTEN gene deletion, NOTCH1 locus amplification along with genomic amplifications at 8q24.3, 9q34.3, 11p15.5 and 14q11.2, and deletions at 4q35.2, 5q31.3, 7q36.3, 12q24.33, and 16p11.2. By compared copy number between pre- and post-treatment, we found significant copy number changes in 34 genomic loci. To estimate tumor DNA fraction in urine cfDNAs, we developed a Urine Genomic Abnormality (UGA) score algorithm that summed top ten most significant segments with copy number changes. We found that UGA scores were associated with tumor burden and UGA score change after stage-specific therapies reflected disease progression status and overall survival. The study result demonstrates potential clinical utility of urine cfDNAs in predicting treatment response and monitoring disease progression.

B. Overview of Using Urine Cell Free DNA as Biomarkers in Advanced Prostate Cancer.

Prostate cancer is the most common non-skin cancer among US men with 220,800 new cases estimated in 2015 and more than 27,500 projected deaths[1]. Advanced hormone sensitive prostate cancer has traditionally been treated initially with androgen deprivation therapy (ADT) that slows disease progression. Recently it has been shown that addition of docetaxel chemotherapy prolongs survival in this stage [2]. Despite these advances, emergence of castration-resistant prostate cancer (CRPC) is inevitable for which stage traditionally chemotherapy with docetaxel has been used [3-7]. Several novel systemic anti-cancer therapies currently being used after ADT failure to treat CRPC [8-17], have prolonged longevity of life. Despite these advances, predictive biomarkers for response, efficacy or toxicity to traditional hormonal therapy for hormone sensitive state or the novel castration resistant treatments are lacking and the practice of prostate cancer therapeutics continues to be based on best clinical estimates. Molecular classifiers of disease outcome or therapeutic benefit and toxicity are needed for individualizing therapeutic choices.

Body fluid based biomarkers are appealing in advanced prostate cancer because they are less invasive and easily accessible. Cell free DNA (cfDNA) based somatic aberrations in plasma [15, 18, 19] of cancer patients has been extensively reported. In advanced prostate cancer patients' plasma cfDNA is detected in hormone sensitive and castrate resistant stages [20]. It remains unclear if genomic profiling to detect cfDNA aberrations in urine is feasible and may associate with clinical or treatment outcomes in advanced prostate cancer patients. To determine somatic genomic changes, we performed whole-genome sequencing and analyzed copy number variations in matched urine specimens of advanced prostate cancer patients previously sequenced for plasma cfDNA [20]. We first evaluated the UGA algorithm based on genome-wide copy number variation (CNVs) for determining association with treatment response and clinical outcomes in patients receiving standard advanced prostate cancer treatments. We then compared cfDNA based CNVs in urine with previously reported plasma cfDNA CNVs [20]. Our data showed that urine cfDNAs may generate comparable results as plasma cfDNA in CNVs analysis and UGA score may have clinical application in accessing treatment response and clinical outcomes.

C. Observed Genomic Abnormality of Urine Cell Free DNA and Plasmas Cell Free DNA in Patients Having Advanced Prostate Cancer as HSPC Prostate Cancer Patients Treated with ADT Alone or CRPC Patients Treated with ADT and Chemotherapy.

1. Patients' Clinical Characteristics.

Matched urine specimens for patients with previous cfDNA sequencing of plasma specimens were available for 9 of 10 hormone sensitive prostate cancer (HSPC) patients and the ten patients with castrate resistant prostate cancer (CRPC) disease. These samples were selected for cfDNA purification and profiling. Patient characteristics for these two advanced cancer cohorts are presented in Table 1U. Each subject had two serial urine specimens available before and after initiating stage-specific treatments. Patients in the HSPC sub cohort underwent continuous ADT and for the CRPC sub cohort received docetaxel chemotherapy which was added to ADT as a standard of care treatment. The mean time between two sample collections in the HSPC was 128 days, and the mean time between two sample collections in the CRPC was 112.4 days. The median follow up study time was and 64.00 months (40.93-69.13 months) and 20.97 months (range 6.77-72.83 months) for HSPC and CRPC the cohorts respectively.

2. Urine cfDNA Yield and Quality.

Figure 10:
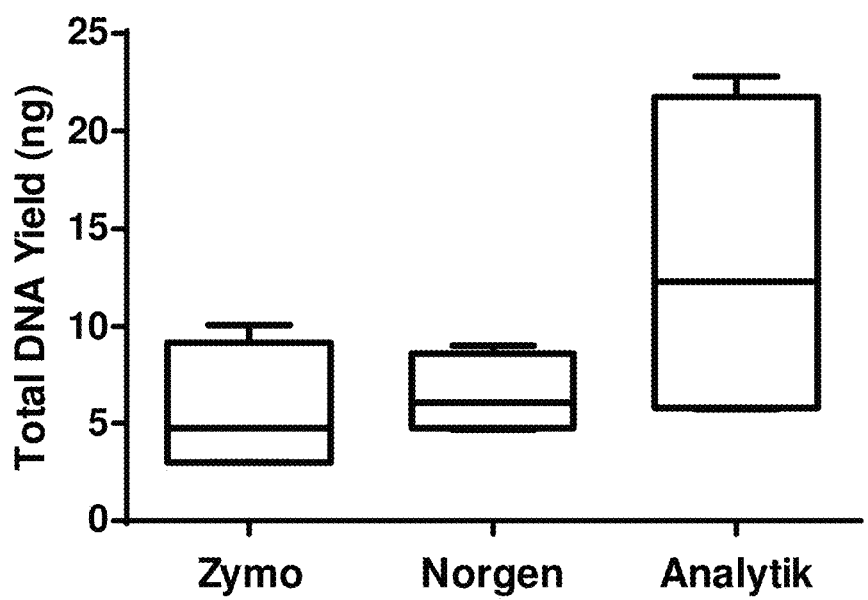
FIG. 10: shows exemplary extracted 15 ml normal adult male urine cfDNA final concentration by three different kits (Zymo, Norgen, and Analytikjena).
Figure 11:
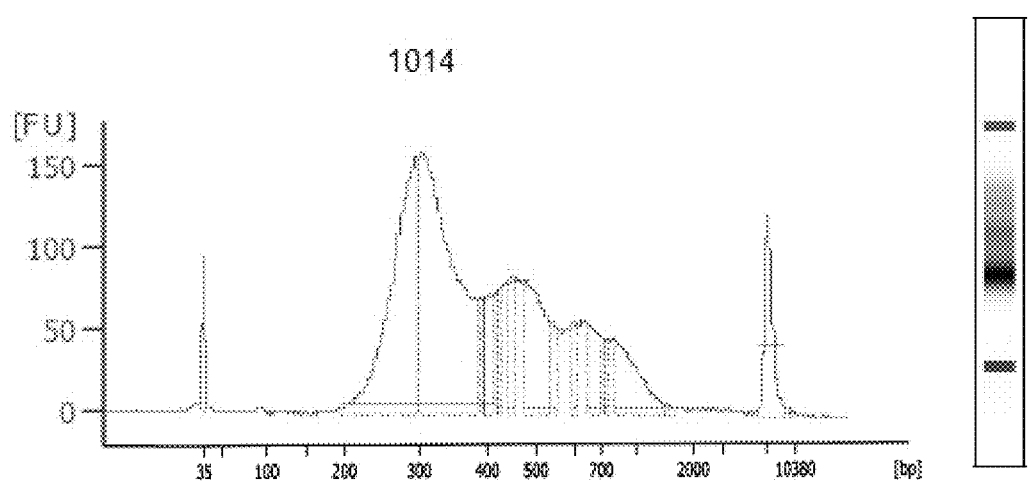
FIG. 11: shows exemplary representative electropherogram of sequencing library. Fragment sizes after adding sequencing adaptors range from 250 to 1500 bp with peak at approximately 300 bp.

To assess cfDNA yield, we tested three different kits using one single urine sample. We found that average cfDNA yields were 5.63 ng, 6.46 and 13.27 ng for Zymo, Norgen and Analytik, respectively (FIG. 10). The Analytik kit generated approximately 2 fold more cfDNA than two other kits. Due to relatively high yield, 2 ng cfDNAs extracted using the Analytik kit was directly used for sequencing library construction. However, qualities of the sequencing libraries made from Analytik-derived cfDNA were extremely poor in three separate evaluation tests as determined by lack of featured library fragment band at approximately 300-310 bp. Meanwhile, cfDNAs derived from Zymo kit generated consistent high quality sequencing library in three separate evaluation tests (FIG. 11).

3. Urine cfDNA and Sequencing Library Quality.

The final cfDNA yield from 15 ml urine samples ranged from undetectable (<0.02 ng/ul) to 1.6 ng/ul in 10 ul elution buffer. Among 19 patients with both pre and post-treatment urine specimen detectable cfDNAs was measurable in 33 of the 38 samples. cfDNA yields from the remaining 5 samples were too low for measurement. For the 33 samples with total cfDNA >0.25 ng, sequencing libraries were prepared with final concentration of library DNAs between 0.878 and 3.490 ng/ul. High sensitivity DNA chip showed multiple library fragments with peak size at approximately 300 bp (FIG. 11). Whole genome sequencing generated approximately 7.6 million (ranged from 4.3 to 15.2) raw reads and 6.9 million (ranged from 3.7 to 14.0) mappable reads. Corresponding mappable reads were observed from 77 to 93 percent of raw reads. The mean read count was approximately 134 per 60 kb genomic window (Table 2U).

4. Overall Urine cfDNA Genomic Abnormalities.

Figure 12:
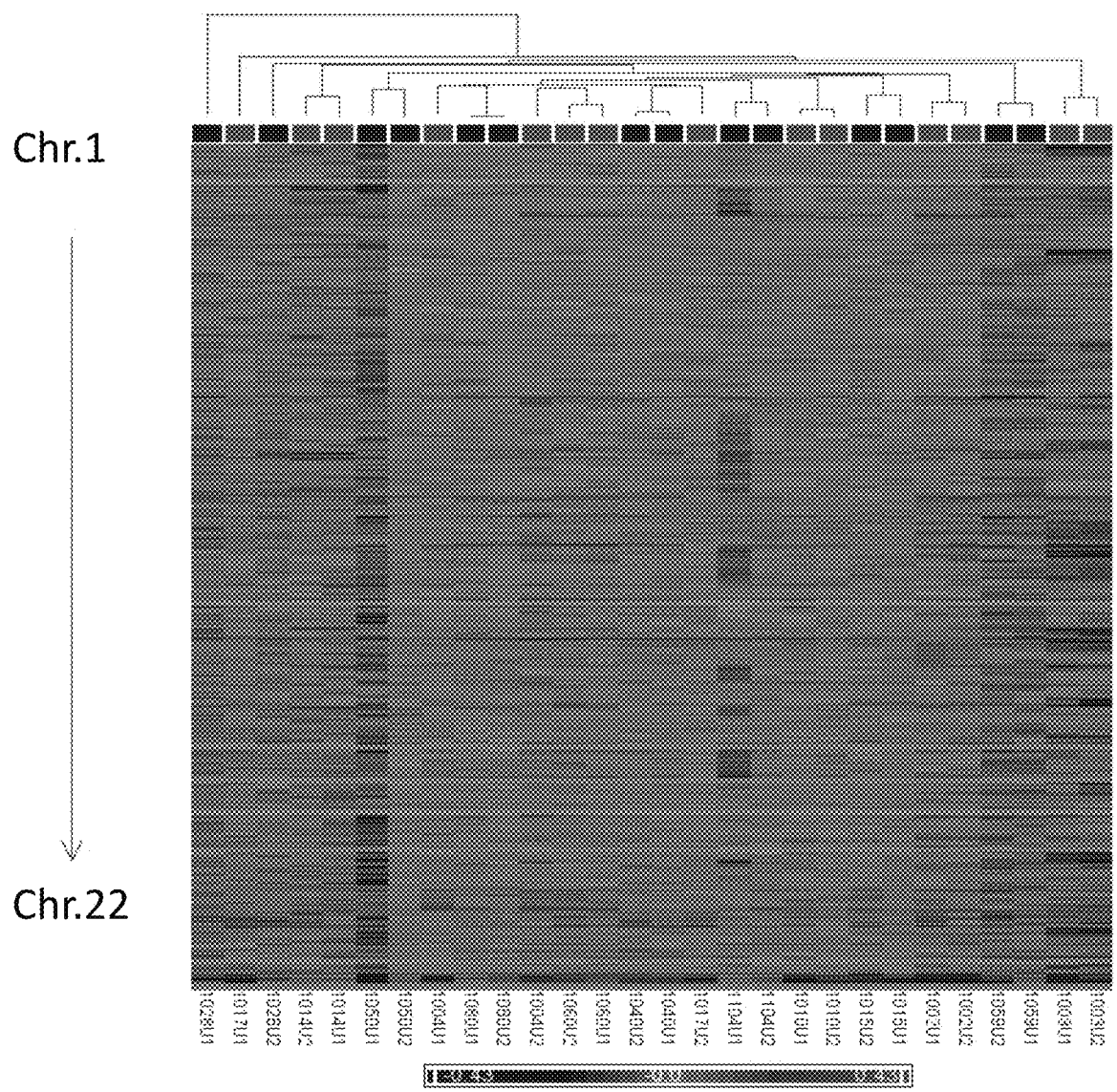
FIG. 12: shows exemplary Log 2 ratio-based clustering analysis in 14 urine pairs before and after stage-specific therapy.
Figure 13:
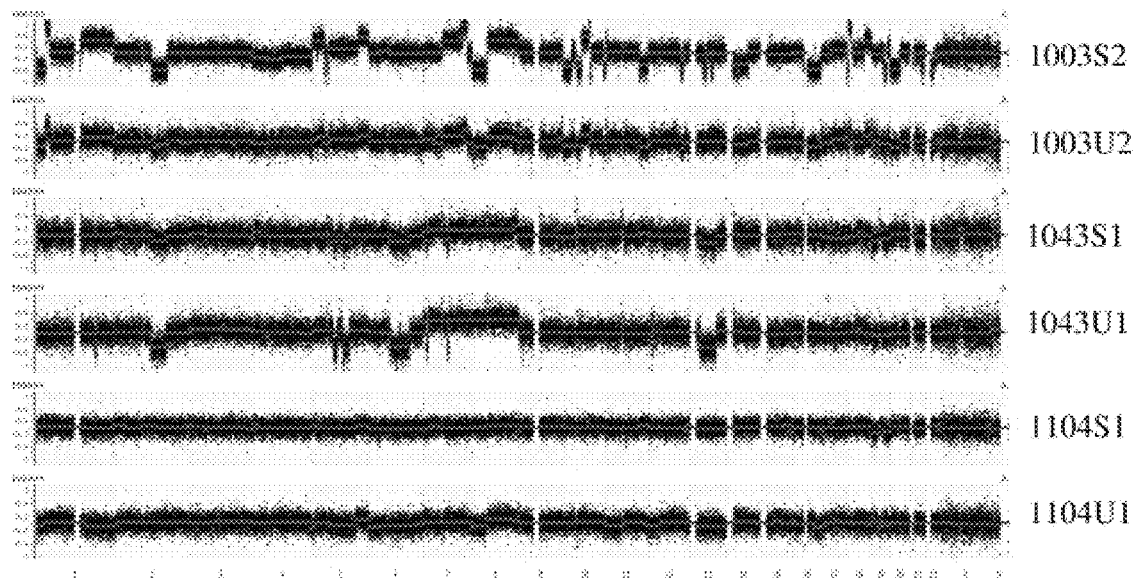
FIG. 13: shows an exemplary overall view of genomic abnormalities in plasma and urine.

To evaluate genomic abnormality, for each genomic bin, log 2 ratios between read counts from urine cfDNA and lymphocyte-derived genomic DNA (gDNA) in the same patient were calculated. Fragmentation-based CNV analysis showed that genomic abnormalities were detectable in the cfDNAs in the 19 patients tested. A greater number of genomic abnormalities were observed in the CRPC sub cohort undergoing chemotherapy than in the HSPC cohort receiving ADT alone. In fact, four of 10 CRPC patients (1003, 1004, 1014, 1017) and 2 of 9 HSPC patients (1050 and 1059) showed significant genomic abnormalities. Of the 33 successfully sequenced cfDNA specimens, five patients had either a pre- or post-treatment specimen cfDNA only while remaining 14 patients had both pre- and post-treatment cfDNAs. Among these 14 patients with paired samples, seven belonged to the HSPC sub cohort and other seven to the CRPC sub cohort. For these 14 patients, we performed unsupervised clustering analysis using log 2 ratios in each genomic window and found that 11 pairs were clustered together (FIG. 12). Among those, some samples such as patients 1050 and 1104 demonstrated significant CNV intensity differences between pre- and post-treatments. By comparing cfDNA based CNVs from urine and plasma in matched patient samples, we observed consistent tumor-associated CNVs, although differences in the degree of changes in the two specimen types was observed (FIG. 13).

5. Genomic Abnormalities at Specific Loci.

Figure 14:
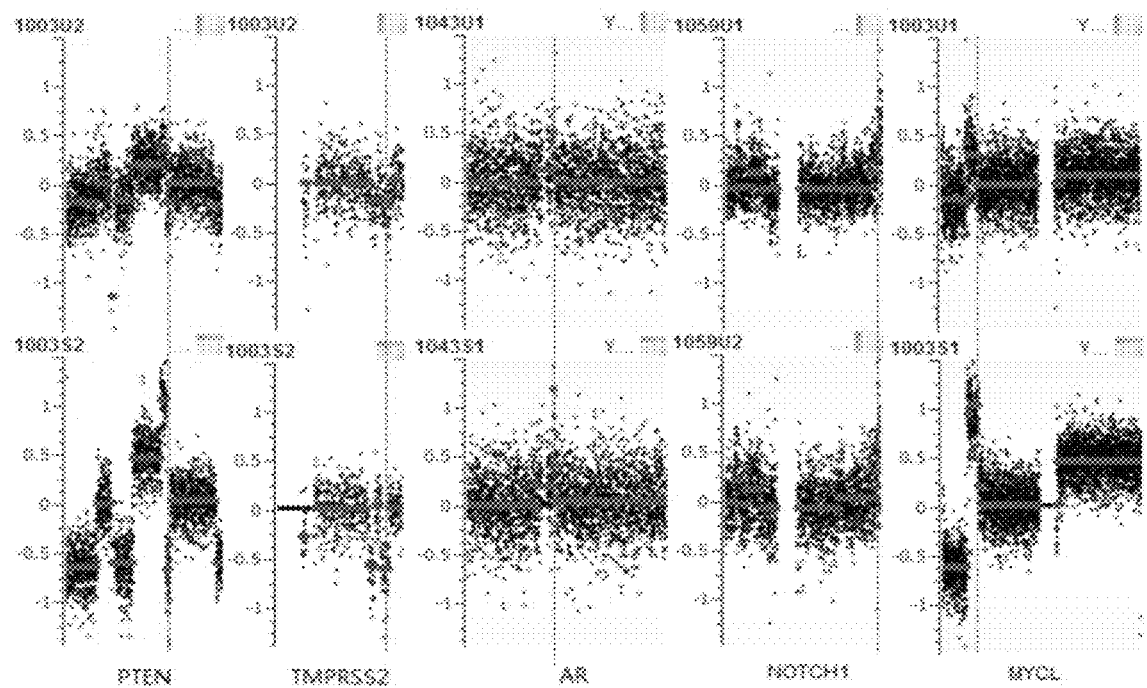
FIG. 14: shows exemplary representative genomic abnormalities detected at specific chromosomal loci. PTEN loss at chr 10, TMPRSS2 loss at chr 21, and AR amplification at chrX, and NOTCH1 amplification at chr 9, and MYCL amplification at chr 1 are shown. Vertical lines indicate the locations of these chromosomal aberrations.
Figure 15:
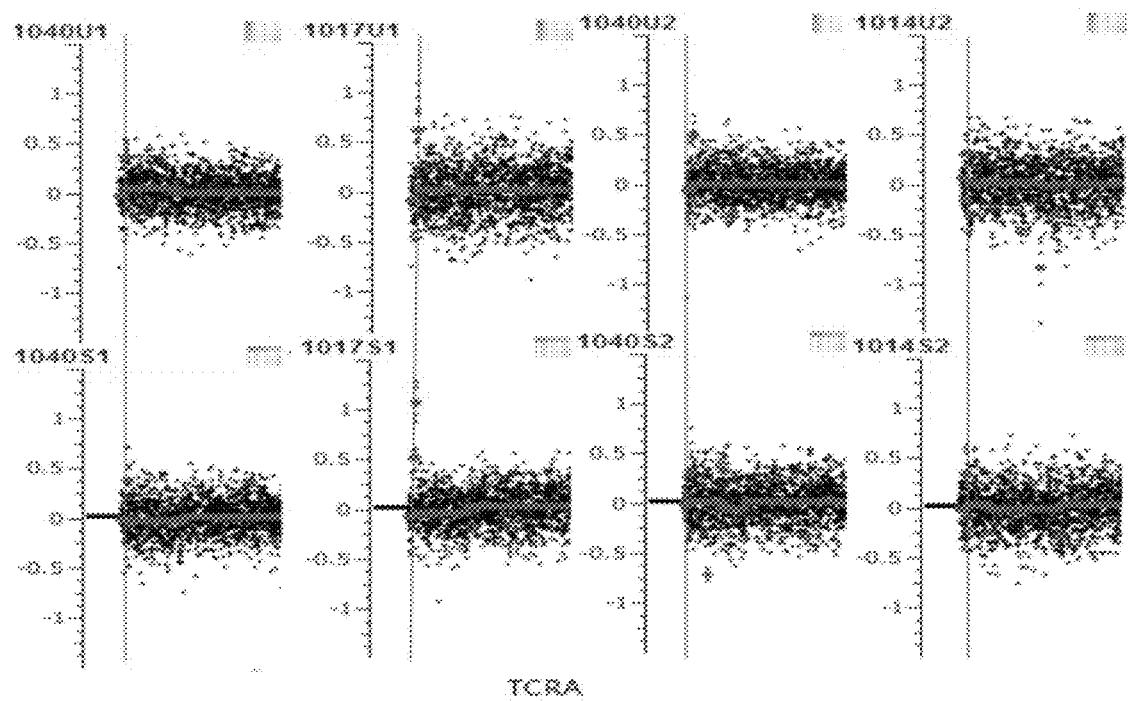
FIG. 15: shows an exemplary false positive (pseudo) amplification at TCRA locus.

To further define genomic abnormalities in urine, we performed detailed analysis at chromosomal regions with putative and frequent aberrations in prostate cancer. Among those, genomic region at androgen receptor (AR) is most frequently amplified in CRPC stage. To examine the amplification status, we zoomed to the genomic region containing AR and observed AR locus amplification in five of ten CRPC cases (#1003, #1005, #1010, #1017, and #1043) but none in nine HSPC cases. Although the amplicon boundaries varied they contained whole AR gene. Another common genomic aberration in prostate cancer is at TMPRSS2 locus where frequent rearrangements create various fusion genes. We observed urine TMPRSS2 genomic variations in four cases with CRPC (#1003, #1005, #1014 and #1017) and 2 cases with HSPC (#1040, and #1098). The breakpoints for two genomic losses occurred at the two gene (ERG and TMPRSS2) regions, therefore forming a TMPRSS2-ERG fusion gene. The third most common genomic abnormality observed in prostate cancer is PTEN gene deletion. We found the PTEN loss in 4 cases of our CRPC sub cohort (#1002, #1005, #1043 and #1060) and one case of HSPC (#1080) in the urine cfDNAs. Additionally, we found NOTCH1 locus amplification in one CRPC patients (#1014) and four HSPC patients (#1050, #1059, #1084 and #1098). Most of these abnormalities in urine cfDNAs were also observed and previously reported in the matched plasma cfDNAs [20] (FIG. 14 and Table 3U). Other chromosomal regions were also frequently altered in the tested samples with most having at least one common deletion or amplification per chromosome. From the common regions, we further defined the minimally overlapped regions that were involved in amplifications at 8q24.3, 9q34.3, 11p15.5 and 14q11.2 and deletions at 4q35.2, 5q31.3, 7q36.3, 12q24.33, and 16p11.2 (Table 4U). Among those, 7 regions including 5q31.3, 7q36.3, 8q24.3, 9q34.3, 11p15.54, 14q11.2 and 16p11.2 were reported to be associated with prostate cancer [21-26]. Meanwhile, gene mutations at these loci have also been reported in prostate cancer tissues [27-29]. In addition, frequent "amplification" at TCRA locus was observed in most urine samples. Because extensive rearrangements (deletions) at TCRA locus during T cell development, lymphocyte-derived gDNA may harbor partial deletions at this locus. Using such gDNAs as controls to normalize cfDNA may generate false positive amplification at this locus (FIG. 15).

6. Urine Genomic Abnormality (UGA) Score and its Clinical Association

Figure 16:
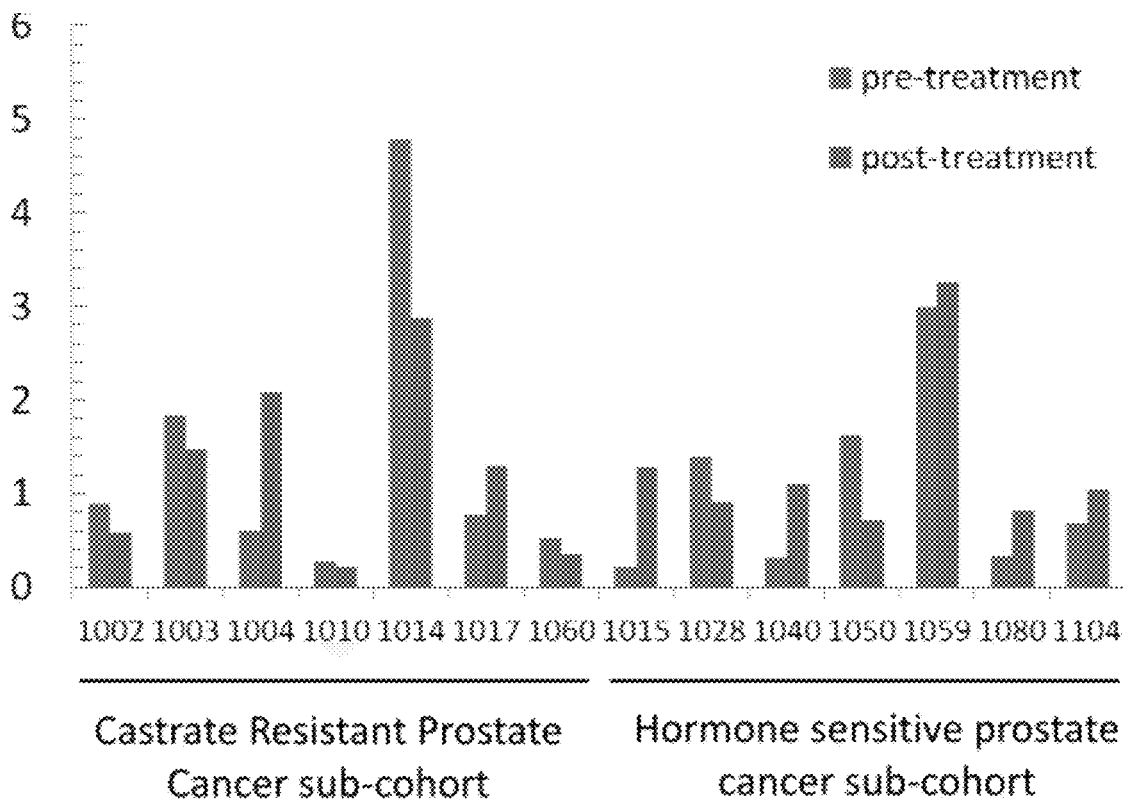
FIG. 16: shows exemplary Urine Genomic abnormality scores of 14 paired samples with pre- and post-stage specific therapies
Figure 17:
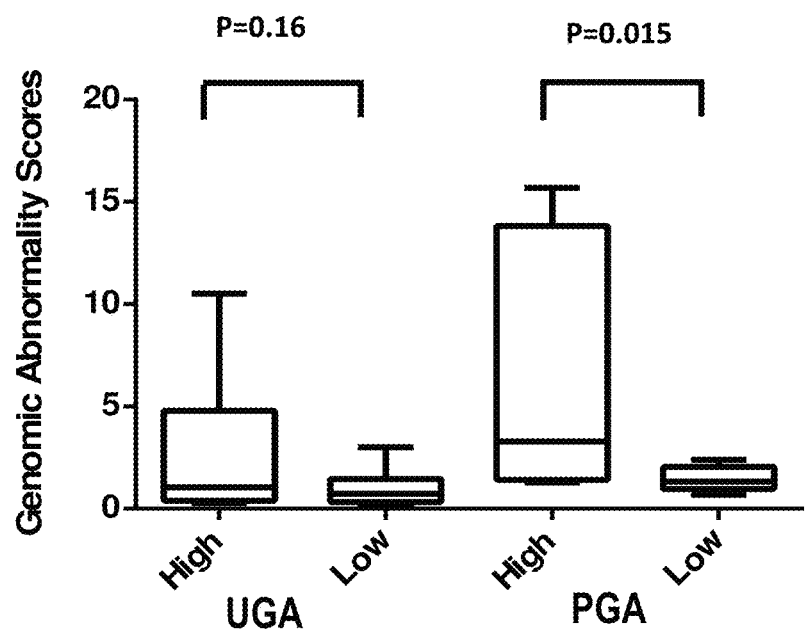
FIG. 17: shows exemplary UGA and PGA score differences between high and low volume prostate cancer patients. Average UGA score before treatment is lower in low volume patients (n=10, mean=0.98±0.84) than in high volume patients (n=7, mean=2.77±3.75). Average PGA score before treatment is significantly lower in low volume patients (n=11, mean=1.40±0.58) than in high volume patients (n=8, mean=6.41±6.20).

As described above, we calculated a PGA score based on multiple genomic abnormalities in plasma as a potential classifier for association with treatment response and survival [20]. To evaluate a similar UGA based classifier, we modified the previously reported PGA score algorithm and created UGA scores. The UGA score was calculated using the sum of absolute log 2 ratios of the top ten abnormal genomic segments. Both inter and intra patient UGA score variations (for the 14 paired specimens) were observed (FIG. 16). UGA scores in pre-treatment group were higher in patients with high volume disease than low volume disease although it did not reach statistical significance (p=0.16) (FIG. 17).

To see whether genomic abnormality change between treatment points predicted clinical outcomes, we calculated urine TEff index by comparing percent differences between pre and post-treatment UGA scores for the patients with the paired samples. Kaplan-Meier survival analysis showed that a higher TEff index was significantly associated with better survival (p≤0.04) in CRPC cohort (FIGS. 18A and 18B). Five of seven CRPC patients with a decrease in the post chemotherapy UGA score were alive during the follow-up time while the two patients' whose UGA score increased died (Table 5U). For HSPC sub cohort, the UGA based TEff index also showed a clear trend association of higher TEff index with longer progression time to castration resistance (FIG. 18C).

7. Treatment-Associated Genomic Abnormalities.

Figure 19:
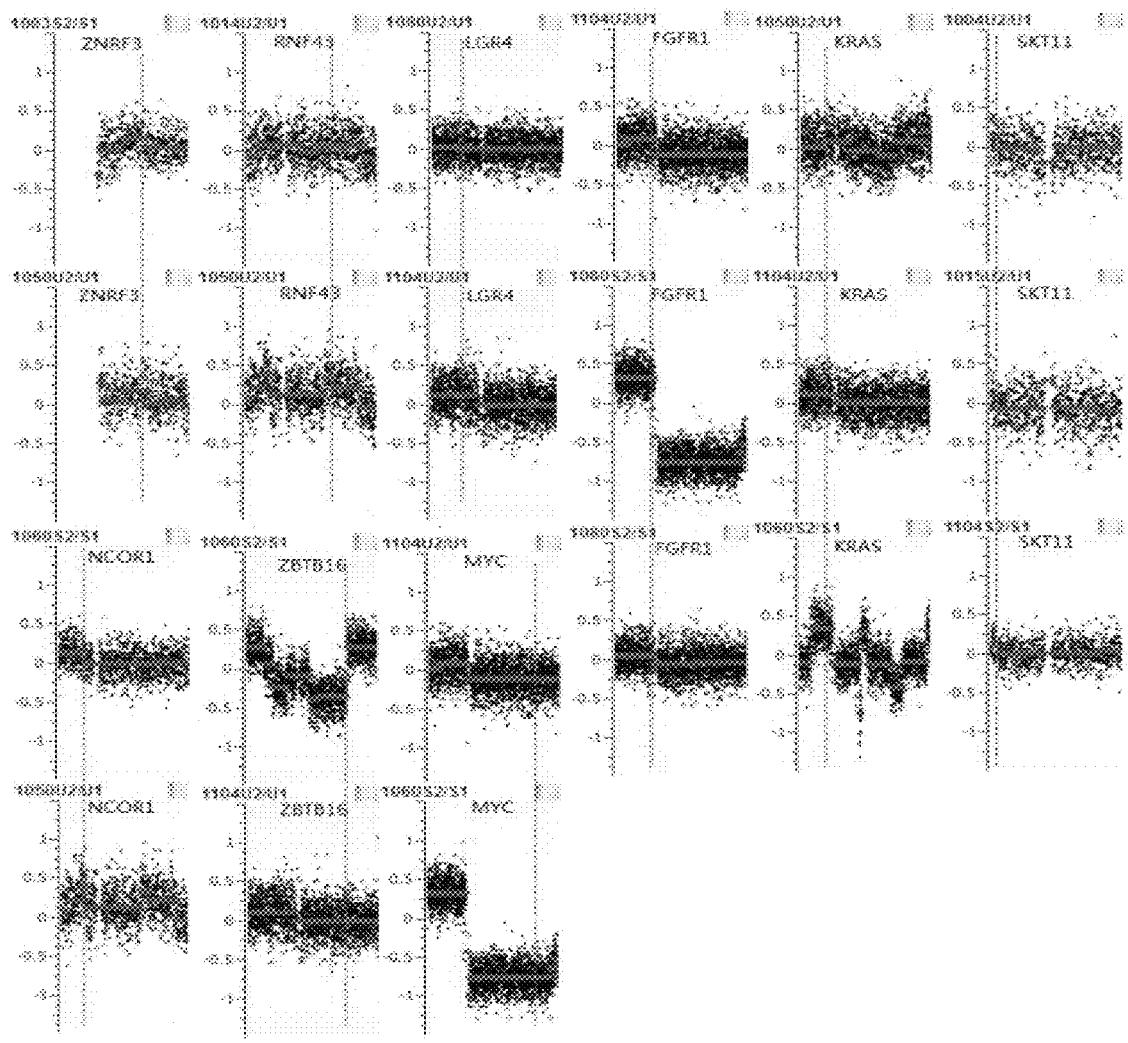
FIG. 19: shows exemplary treatment-related genomic regions and genes.
Figure 20:
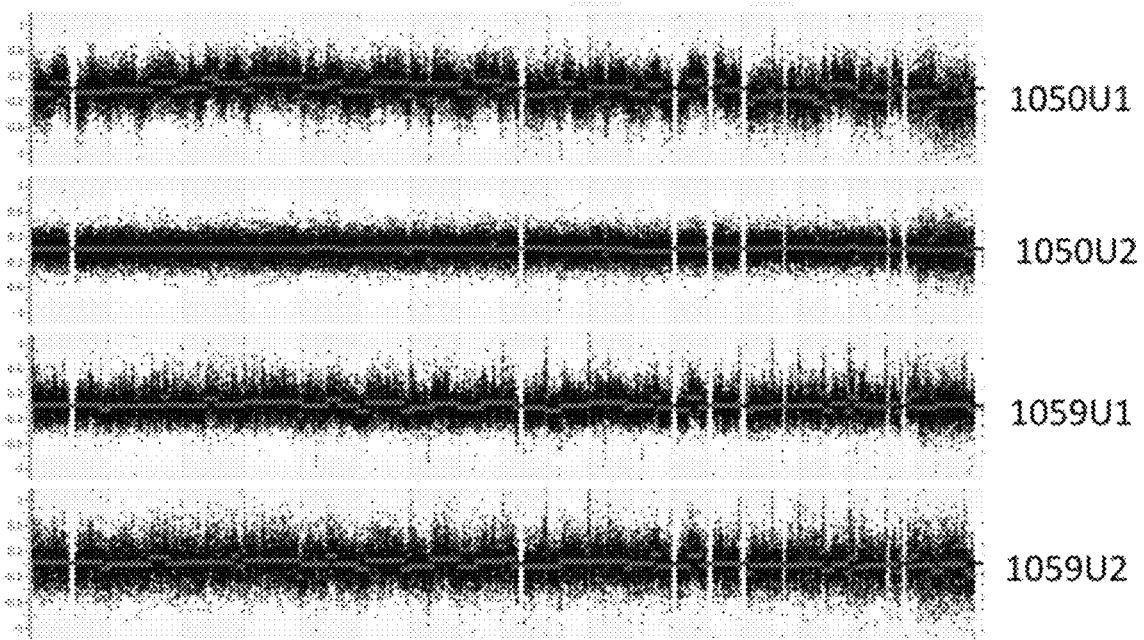
FIG. 20: shows exemplary representative figure of significant number of genomic abnormalities CNVs in two CRPC patients.

To examine treatment-associated genomic alterations, we generated log 2 ratios between pre- and post-treatment specimens directly from scaled read counts at each genomic window and performed segmentation analysis for treatment-related genomic gain or loss. Compared to pre-treatment, we observed a total of 34 genomic loci with copy number changes in the post treatment specimen. By defining minimal overlap regions at each locus, we identified commonly shared regions that covered nine genes (ZNRF3, RNF43, LGR4, NCOR1, ZBTB16, MYC, FGFR1, KRAS and STK11) (FIG. 19 and Table 6U). For example, after treatment, genomic region covering LGR4 was amplified in two cases of HSPC (#1080 and #1104), and genomic region covering ZBTB16 was deleted in two cases of CRPC (#1014 and #1060). The copy number changes in the remaining seven gene regions were found in both advanced HSPC and CRPC urine specimens.

Table 1U. Clinical characteristics of 19 advanced prostate cancer patients.

TABLE 1

Clinical Characteristics of 19 advanced prostate cancer patients (1)

| Patient ID | Age at time of Diagnosis (years) | Patient Group | Treatment | TNM staging at diagnosis | Metastatic status before treatment* | PSA (ng/ml) at time of 1st sample collection | PSA (ng/ml) at time of 2nd sample collection | Disease status* | Follow-up time (Months) | Time between two sample collections (Months) |
|---|---|---|---|---|---|---|---|---|---|---|
| 1001 | 62 | CRPC | Chemo | T4N1M1 | High Volume | 8.2 | 0.42 | 1 | 68.73 | 147 |
| 1002 | 66 | CRPC | Chemo | T2cNxM0 | Low Volume | 9.3 | 1.6 | 1 | 17.47 | 89 |
| 1003 | 54 | CRPC | Chemo | T3aN0M0 | High Volume | 107 | 162 | 1 | 6.77 | 84 |
| 1004 | 69 | CPPC | Chemo | T3aNxM0 | Low Volume | 3.4 | 4.6 | 0 | 72.83 | 92 |
| 1005 | 69 | CRPC | Chemo | T3bN2M1 | High Volume | 0.48 | 0.1 | 1 | 9.53 | 145 |
| 1010 | 72 | CRPC | Chemo | T3bN1M0 | High Volume | 5 | NA | 1 | 21.83 | 144 |
| 1014 | 61 | CRPC | Chemo | T2bN1M1 | High volume | 126 | 56.8 | 1 | 20.10 | 99 |
| 1017 | 63 | CRPC | Chemo | T2aN0M0 | Low Volume | 22 | 104 | 0 | 70.80 | 139 |
| 1043 | 73 | CRPC | Chemo | T2aNxM1 | High Volume | 15.5 | 8 | 1 | 40.13 | 80 |
| 1060 | 78 | CRPC | Chemo | TxNxM1 | High Volume | 3.7 | 1.4 | 1 | 18.93 | 104 |
| 1015 | 67 | HSPC | ADT | T2cNxM0 | Low Volume | 1 | 0.9 | 1 | 0.00 | 98 |
| 1028 | 49 | HSPC | ADT | T3bN0M0 | Low Volume | 0.33 | 0.12 | 0 | 68.77 | 154 |
| 1040 | 53 | HSPC | ADT | T2NxM0 | Low Volume | 2.5 | <0.10 | 0 | 40.93 | 168 |
| 1050 | 64 | HSPC | ADT | T3bN1M1 | Low Volume | 4.2 | <0.10 | 0 | 65.90 | 136 |
| 1059 | 62 | HSPC | ADT | T3bN1M0 | Low Volume | 2.9 | <0.10 | 1 | 0.37 | 116 |
| 1080 | 65 | HSPC | ADT | T3bN1M0 | Low Volume | 16 | 0.77 | 1 | 28.33 | 172 |
| 1084 | 57 | HSPC | ADT | T3bN0M0 | High Volume | 2.2 | 0.24 | 1 | 11.67 | 78 |
| 1098 | 78 | HSPC/LA | ADT | T2aNxM0 | Low Volume | 5.7 | 0.54 | 0 | 63.83 | 131 |
| 1104 | 67 | HSPC | ADT | T2cN1M1 | Low Volume | 37 | <0.10 | 1 | 1.93 | 99 |

*For CRPC group, 1 = dead, 0 = alive. For HSPCgroup, 1 = disease progression, 0 = no progression.

TABLE 2U

Statistics of whole genome sequencing

| Sample ID | Raw reads | Mappable reads | Percent mapped | Reads/60 kb |
|---|---|---|---|---|
| 1001U2 | 8,559,863 | 7,780,937 | 90.90 | 151 |
| 1002U1 | 5,834,360 | 5,359,747 | 91.87 | 104 |
| 1002U2 | 6,905,307 | 6,218,374 | 90.05 | 120 |
| 1003U1 | 8,466,006 | 6,717,216 | 79.34 | 130 |
| 1003U2 | 8,249,703 | 6,668,418 | 80.83 | 129 |
| 1004U1 | 5,695,192 | 5,239,912 | 92.01 | 101 |
| 1004U2 | 6,523,691 | 6,056,921 | 92.85 | 117 |
| 1005U1 | 8,028,779 | 7,146,997 | 89.02 | 138 |
| 1010U1 | 6,941,555 | 6,376,244 | 91.86 | 123 |
| 1010U2 | 8,066,311 | 7,392,163 | 91.64 | 143 |
| 1014U1 | 5,925,269 | 5,434,275 | 91.71 | 105 |
| 1014U2 | 5,709,509 | 5,264,081 | 92.20 | 102 |
| 1015U1 | 6,757,096 | 6,173,896 | 91.37 | 119 |
| 1015U2 | 5,082,468 | 4,680,443 | 92.09 | 91 |
| 1017U1 | 7,268,083 | 6,383,512 | 87.83 | 124 |
| 1017U2 | 8,751,507 | 7,962,944 | 90.99 | 154 |
| 1028U1 | 4,366,638 | 3,758,949 | 86.08 | 73 |
| 1028U2 | 6,505,105 | 5,927,164 | 91.12 | 115 |
| 1040U1 | 7,715,099 | 6,887,111 | 89.27 | 133 |
| 1040U2 | 8,481,528 | 7,888,688 | 93.01 | 153 |
| 1050U1 | 6,635,918 | 6,006,158 | 90.51 | 116 |
| 1043U1 | 7,398,308 | 6,791,284 | 91.80 | 131 |
| 1050U2 | 10,320,989 | 9,167,473 | 88.82 | 177 |
| 1059U1 | 15,250,498 | 14,061,397 | 92.20 | 272 |
| 1059U2 | 6,303,913 | 5,865,752 | 93.05 | 114 |
| 1060U1 | 10,515,071 | 9,691,459 | 92.17 | 188 |
| 1060U2 | 7,294,862 | 6,713,772 | 92.03 | 130 |
| 1080U1 | 9,525,919 | 8,793,277 | 92.31 | 170 |
| 1080U2 | 8,771,271 | 7,816,538 | 89.12 | 151 |
| 1084U1 | 10,930,339 | 10,145,924 | 92.82 | 196 |
| 1098U2 | 7,507,997 | 5,835,747 | 77.73 | 113 |
| 1104U1 | 5,670,174 | 5,231,642 | 92.27 | 101 |
| 1104U2 | 7,542,611 | 6,868,682 | 91.07 | 133 |
| Average | 7,681,847 | 6,918,397 | 90.06 | 134 |

Table 3U. Loss or gain of common prostate cancer-related genes.

TABLE 3

Loss or gain of common prostate cancer-related genes.

| Gene | Deletion or Amplification | Urine | Plasma |
|---|---|---|---|
| PTEN | Deletion | 1005U1, 1043U1, 1080U1, 1060U2, 1080U2, 1002U1 | 1003S1, 1005S1, 1003S2, 1060S1, 1005S2, 1043S2, 1080S1 |
| TMPRSS2 | Deletion | 1003U1, 1003U2, 1017U2, 1005U1, 1098U2, 1040U1, 1014U1 | 1003S1, 1003S2, 1043S1, 1005S1, 1005S2, 1014S1 |
| AR | Amplificaton | 1003U2, 1003U1, 1005U1, 1010U1, 1017U1, 1043U1 | 1003S2, 1005S2, 1010S1, 1010S2, 1028S2, 1043S1, 1060S1, 1060S2 |
| NOTCH1 | Amplificaton | 1059U1, 1059U2, 1098U2, 1084U1, 1050U1, 1014U1 | 1059S1, 1059S2, |
| MYCL | Amplificaton | 1003U1, 1003U2, 1104U1, | 1003S1, 1003S2, 1005S1, 1059S2 |

Table 4U. Co-deletion or co-amplification segment of minimal overlap region.

TABLE 4

Co-deletion or co-amplification segment of minimal overlap region

| Chr. | Start | Stop | Cytoband | Deletion or Amplification | Representative Genes | Sample ID Number | Sample ID(CRPC) | Sample ID(HSPC) | References |
|---|---|---|---|---|---|---|---|---|---|
| Chr4 | 189,361,841 | 191,048,481 | 4q35.2 | Deletion | | 14 | 1060U1, 1060U2, 1010U2, 1003U2, 1002U1, 1002U2 | 1104U1, 1104U2, 1098U2, 1080U1, 1080U2, 1059U1 1059U2, 1050U1, | ? |
| Chr5 | 140,501,206 | 140,700,782 | 5q31.3 | Deletion | NR3C1 | 7 | 1060U1, 1060U2, 1017U1, 1005U1, 1001U2, | 1040U1, 1040U2 | ? |
| Chr7 | 157,558,688 | 159,558,887 | 7q36.3 | Deletion | VIPR2 | 6 | 1060U1, 1060U2 | 1104U1, 1084U1, 1080U1, 1080U2 | ? |
| Chr8 | 144,345,765 | 146,121,832 | 8q24.3 | Amplification | NDR1. | 9 | 1014U2, 1010U2, 1003U2 1002U1, 1002U2, 1003U1, | 1104U1, 1104U2, 1098U2, 1059U1, 1059U2, 1050U1, | ? |
| Chr9 | 139,266,197 | 140,278,759 | 9q34.3 | Amplification | Notch1, RXRA | 10 | 101U2, 1014U1, 1060U1, 1002U2, 1003U1, | 1050U1, 1059U1, 1059U2, 1084U1, 1098U2 | ? |
| chr11 | 1 | 968,056 | 11p15.5 | Amplification | CD151, MUC6, MUC2, STIM1, CTSD, SLC22A18 | 9 | 1003U2, 1014U1 | 1059U1, 1059U2, 1084U1, 1050U1 1028U2, 1040U2, 1059U, | ? |
| Chr12 | 133,335,093 | 133,778,067 | 12q24.33 | Deletion | | 7 | 1001U2, 1017U2, 1043U1, 1017U1, 1017U2, 1014U2, 1010U1, 1010U2, 1003U2 | 1080U1, 1080U2, | ? |
| Chr14 | 22,322,547 | 22,914,657 | 14q11.2 | Amplification | NDRG2, TCRA | 10 | 1017U1, 1017U2, | 1084U1, 1040U1, 1040U2, 1104U1, 1104U2, 1059U1, 1059U2, 1050U2, 1028U1, | ? |
| Chr16 | 33,889,263 | 33,988,937 | 16p11.2 | Deletion | TMS1 | 12 | 1005U1, 1004U1, 1004U2 | 1015U2 | ? |

TABLE 5U

Genomic abnormality scores in 19 advanced prostate cancer patients

| | | | Plasma | | | Urine | | |
|---|---|---|---|---|---|---|---|---|
| Patient ID | Patient Group | Disease status* | Pre-PGA | Post-PGA | TEff | Pre-UGA | Post-UGA | TEff |
| 1001 | CRPC | 1 | 3.00 | 3.78 | −33.38 | NA | 1.55 | NA |
| 1002 | CRPC | 1 | 1.36 | 1.21 | 16.76 | 0.90 | 0.59 | 61.78 |
| 1003 | CRPC | 1 | 15.26 | 14.85 | 3.97 | 1.84 | 1.47 | 31.59 |
| 1004 | CRPC | 0 | 2.39 | 2.35 | 2.64 | 0.61 | 2.08 | −177.75 |
| 1005 | CRPC | 1 | 9.54 | 3.12 | 161.45 | 0.39 | NA | NA |
| 1010 | CRPC | 1 | 1.34 | 1.01 | 41.47 | 0.27 | 0.22 | 30.26 |

TABLE 5U-continued

Genomic abnormality scores in 19 advanced prostate cancer patients

| Patient ID | Patient Group | Disease status* | Plasma | | | Urine | | |
|---|---|---|---|---|---|---|---|---|
| | | | Pre-PGA | Post-PGA | TEff | Pre-UGA | Post-UGA | TEff |
| 1014 | CRPC | 1 | 1.60 | 1.22 | 39.21 | 4.78 | 2.89 | 72.68 |
| 1017 | CRPC | 0 | 2.05 | 2.03 | 1.74 | 0.77 | 1.29 | −74.01 |
| 1043 | CRPC | 1 | 3.54 | 2.10 | 75.13 | 10.50 | NA | NA |
| 1060 | CRPC | 1 | 15.69 | 1.05 | 390.57 | 0.53 | 0.34 | 63.26 |
| 1015 | HSPC | 1 | 0.68 | 1.45 | −110.29 | 0.22 | 1.28 | −253.59 |
| 1028 | HSPC | 0 | 0.96 | 1.26 | −38.89 | 1.39 | 0.92 | 59.60 |
| 1040 | HSPC | 0 | 1.33 | 1.08 | 29.58 | 0.31 | 1.10 | −182.76 |
| 1050 | HSPC | 0 | 0.79 | 1.22 | −62.90 | 1.62 | 0.71 | 118.61 |
| 1059 | HSPC | 1 | 2.24 | 2.21 | 1.91 | 2.99 | 3.27 | −12.62 |
| 1080 | HSPC | 1 | 0.99 | 1.16 | −23.07 | 0.33 | 0.81 | −129.06 |
| 1084 | HSPC | 1 | 1.28 | 1.58 | −29.83 | 1.05 | NA | NA |
| 1098 | HSPC | 0 | 1.40 | 1.28 | 12.42 | NA | 0.70 | NA |
| 1104 | HSPC | 1 | 1.28 | 0.99 | 37.18 | 0.67 | 1.06 | −65.47 |

*For CRPC group, 1 = dead, 0 = alive. For HSPC group, 1 = disease progression, 0 = no progression.

Table 6U. Treatment-related genomic regions and genes.

TABLE 6U

Treatment-related genomic regions and genes

| Chrom. | Location | Gene | Sample ID |
|---|---|---|---|
| Chr22 | 29,427,573-29,453,476 | ZNRF3 | 1003S2/S1(C) 1050U2/U1(H) |
| Chr17 | 56,431,037-56,494,931 | RNF43 | 1050U2/U1(H) 1014U2/U1(C) |
| Chr11 | 27,387,508-27,494,338 | LGR4 | 1104U2/U1(H) 1080U2/U1(H) |
| Chr17 | 15,933,864-16,101,195 | NCOR1 | 1060S2/S1(C) 1050U2/U1(H) |
| Chr11 | 113,933,133-114,126,702 | ZBTB16 | 1060S2/S1(C) 1014U2/U1(C) |
| Chr8 | 128,748,449-128,753,674 | MYC | 1104U2/U1(H) 1060S2/S1(C) |
| Chr7 | 55,177,416-55,279,262 | FGFR1 | 1104U2/U1(H) 1060S2/S1(C) 1080S2/S1(H) |
| Chr12 | 25,358,180-25,403,854 | KRAS | 1104U2/U1(H) 1060S2/S1(C) 1050U2/U1(H) |
| Chr19 | 1,205,798-1,228,434 | STK11 | 1104S2/S1(H) 1004U2/U1(C) 1015U2/U1(H) |

D. Summary.

The examination of tumor components including circulating tumor cells (CTC) and cfDNAs in body fluids referred to as a liquid biopsy [15, 18, 19] offers a non-invasive alternative to sampling metastatic site biopsy in determining prognostic or predictive molecular biomarkers. Successful development of a liquid biopsy program or this clinical application can limit risk from invasive biopsies in advanced cancer stages, which can also be challenging to perform. Additionally the ability to capture tumor associated genomic profiles in circulatory fluids also has the practical advantage of being performed on multiple time points with ease and the potential for offering molecular biomarker profiling in solid tumors in a more dynamic manner during treatments or during expectant monitoring [30]. For CRPC, liquid biopsy profiling is limited to enumeration of CTC, an FDA-approved test for assessing prognosis in metastatic castrate resistant stage. Due to technical limitation, high cost and because metastatic CRPC patients are known to have variable measurable CTC counts, a universal adoption of the CTC count for prognostication has not occurred in clinical practice. Furthermore genomic characterization of CTCs is technically challenging and has not yet been reproducible for clinical use [31]. With advances in high throughput sequencing technology, sensitive detection of tumor-associated cfDNAs in body fluids has become feasible to perform for applying in practice if detected to have clinical utility [32].

cfDNA in blood has been extensively reported and proposed as biomarkers for cancer diagnosis, prognosis and treatment efficacy estimation. It is known that a small amount of cfDNA in blood passes after renal filtration into urine and tumor specific sequences are detectable in cfDNA isolated from urine [33, 34]. However a systematic determination of somatic genomic abnormalities in urine cfDNAs evaluated by high throughput sequencing technology [15, 19, 35] in prostate cancer has not been performed. Several challenges have limited this determination including a lack of precise knowledge on factors that may impact levels of urine cfDNA being measured as the concentration of urine cfDNA stability and fragment size is not as reliable as in blood. In previous reports urine cfDNA profiling using PCR-based detection of candidate tumor-associated genes indicates that, an optimized and uniform method for cfDNA detection in urine that prevents degradation during extraction and storage [36, 37] should also include adequate volumes of specimens. Likely factors influencing cfDNA detection in urine may include processing time of the urine samples after patient donation; the use of preservatives while processing; the time of the urine samples in room temperature before storage in −80° C., and urine volumes. We used a set of specimens collected using a rigorous and uniform sample processing protocol in 15 ml of urine and were able to detect cfDNA concentration in most samples. Another variable that can impact yield and quality is the type of kit used for cfDNA extraction. In this study we evaluated three commercial kits to identify any association of extraction kit with cfDNA quality and yield. Although cfDNA yield using the Analytik kit were the highest, purity of the cfDNAs remained a concern since we were not able to make high quality sequencing library using direct eluent from the kit. The Zymo kit generated relatively low yield but high quality sequencing libraries were consistently observed even at extremely low input of 0.25 ng. This suggests that selection of cfDNA extraction kit and thorough examination of cfDNA quality are variables that should be considered for ensuring the success of sequencing library preparation and subsequent data analysis.

We were able to detect urine CNVs in the patient samples with adequate cfDNA quality and quantity, although the extent of detectable CNV per sample was stage dependent with higher CNVs observed for CRPC patients than in HSPC stage. CNVs were also associated with volume of disease regardless of cancer stage, with a lower level of CNVs observed with low volume disease compared to high volume disease. Upon comparison of urine to plasma CNVs in the matched urine samples a lower incidence of detectable CNVs in urine specimens were generally observed (FIG. 14). This indicates an effect of renal filtration on urine cfDNA content and is in concordance with previous reports in other tumor types [33, 34], suggesting that a smaller fraction of blood cfDNA is detectable in urine. However, the lower urine CNV content did not impact the ability to detect somatic genomic changes similar to plasma in the matched urine specimens. For example, shared specific genomic aberrations were observed in both plasma and urine cfDNAs at loci of PTEN, TMPRSS2 and AR (FIG. 14). These results suggest that both urine and plasma fractions can be used for developing liquid biopsy based biomarkers in advanced prostate cancer.

For identifying predictive biomarkers using urine cfDNA, we examined CNV changes between pre and post treatment, and identified treatment-associated CNV changes at nine gene loci, the majority of which have been reported to play a role in prostate cancer genomics. We were able to detect copy number changes after treatment in RNF43 and ZNRF3 loci. These two closely related single membrane spanning molecules has revealed the receptor-like functionalities of a ligand-binding ectodomain. Combined with the intracellular architecture and activity of an E3 ligase, the two genes may be implicated in the modulation of Wnt signaling [38]. Post treatment copy number changes were also detectable in LGR4 and MYC proto oncogene loci. LGR4 has been reported to function in mammary gland development and mammary stem cells by activating Sox2 via the Wnt/β-catenin/Lef1 signaling pathway [39] and MYC proto-oncogene is frequently deregulated in prostate cancers, activating genetic programs that orchestrate biological processes to promote growth and proliferation [40]. The ability to detect cfDNA and the tumor specific genomic aberrations strongly suggests that a urine based liquid biopsy in advanced stage prostate cancer is feasible and could be developed further for determining predictive and prognostic classifiers.

Figure 18:
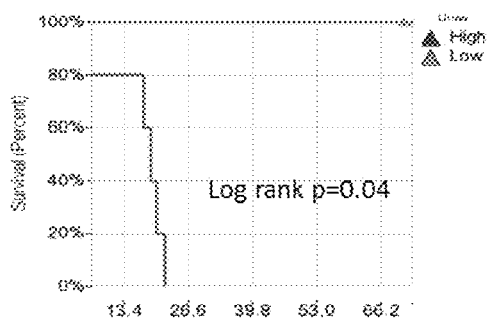
FIG. 18: shows an exemplary Kaplan-Meier analysis for the association of urine Teff(A) and Plasma Teff(B) with overall survival in CRPC, and the association of urine Teff(C) and Plasma Teff(D) with disease progression in HSPC.
Figure 18:
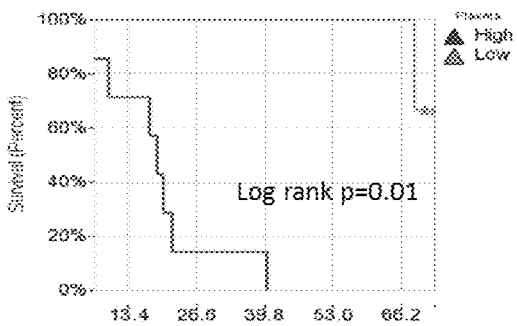
Figure 18:
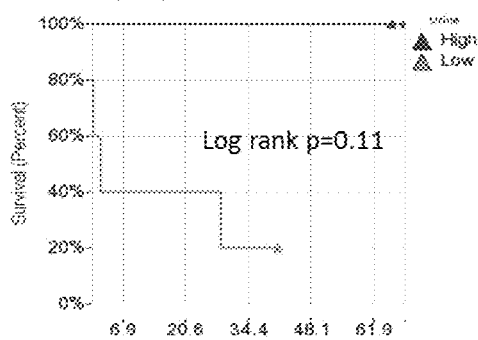
Figure 18:
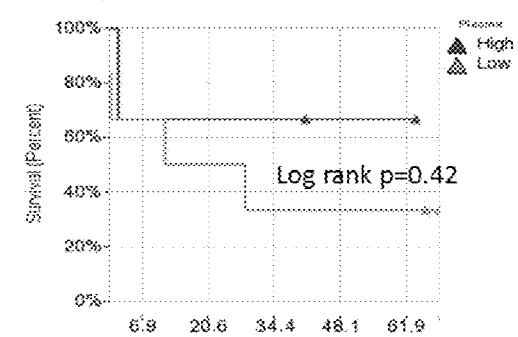

The feasibility approach adopted in our study for developing such classifiers is agnostic of specific gene/region changes and uses an algorithmic summation of the most common genetic abnormalities in urine. Since the mutational landscape of advanced prostate cancer is heterogeneous [41] this approach is likely to account for multiple genomic changes in tumor biology as a result of treatment effect. With this limited data set, we observed an association of the changes in CNVs with survival after treatments for both HSPC and CRPC stages (FIG. 18). Further development of this approach is needed in larger studies in future.

In conclusion, urine cfDNA based genomic abnormality tests provide a measurable classifier that is contemplated for use to assess treatment response and clinical outcomes in advanced prostate cancer patients. Thus, urine cfDNA analysis based on whole-genome sequencing is contemplated as a liquid biopsy tool that is contemplated as a noninvasive biomarker to monitor response to therapy and predict clinical outcomes in future.

E. Materials and Methods.

The following are exemplary materials and methods used during the development of the present inventions.

1. Patient Methods.

Urine specimens were obtained from advanced prostate cancer patients in metastatic hormone sensitive and metastatic castrate resistant stages. Patients were enrolled in a prospectively collected, institutional review board (IRB) approved study at a tertiary hospital while undergoing stage specific standard of care treatments. Informed consent was obtained from these patients enrolled in the registry. The primary purpose of the registry is for developing blood and urine based classifiers of disease and treatment outcomes in this patient population while patients receive standard of care treatments.

Twenty cases (ten hormone sensitive and ten castrate resistant stage patients) were selected for this study with each patient having two serial urine samples. Each patient provided the first of the two urine specimens before initiating stage specific treatment and a second specimen after starting treatments. Cases selected for this study had matched plasma cfDNA sequencing performed previously [20]. Urine specimens were collected at the same time as the plasma collections. Initial processing of urine specimens was performed uniformly within 45 minutes of receiving the sample from the patient. An initial centrifugation at 600 g for 10 minutes was followed by storage of the urine and pellet in −80° C. No urine specimen underwent any freeze-thaw cycles other than at the time of extraction of cfDNA. Peripheral blood mononuclear cell-derived germline DNA (gDNA) was collected at the same time as the plasma and urine specimens. Clinical outcomes of patients undergoing this prospective specimen banking was performed retrospectively as previously described [20].

2. Isolation of Cell Free DNA (cfDNA).

To determine the best urine cfDNA extraction kit, we tested three different commercial products using a single urine sample. The kits included Extract-all Urine DNA kit (Zymo research corp., CA, USA), Urine DNA isolation kit (Norgen Biotek Corp., Ontario, Canada), and PME free-circulating DNA Extraction kit (Analytik Jena Innuscreen GmbH, Berlin, Germany). After thawing the urine sample, it was placed on ice immediately and then centrifuging of 15 ml urine was performed at 3000 rpm for 15 minutes. The supernatant was used for DNA extraction according to each manufacturers' protocol. cfDNA was eluted in 30 ul elution buffer and concentration was measured using Qubit Fluorometer (Life Technology, Carlsbad, Calif.).

3. DNA Extraction and Sequencing Library Preparation.

After an initial evaluation of the yield and quality of cfDNA from the three commercial kits, the Zymo research urine DNA Kit (Zymo Research, Irvine, Calif.) was selected to extract cfDNAs from 15 ml according to the manufacturer's instructions. The extracted DNA was eluted in 10 ul water. 1 ul DNA eluent was quantified using Qubit. The remaining was stored at −80° C. until use. For each patient germline DNA (gDNA) was also extracted and quantified. Sequencing DNA libraries were prepared for the urine cfDNA using a ThruPLEX DNA-Seq Kit (Rubicon Genomics, Inc. Ann Arbor, Mich.). 24 indexed libraries were pooled for single-read sequencing on a HiSeq2000 Sequencing System (Illumina, San Diego, Calif.).

4. Copy Number Variation (CNV) Calculation.

Raw sequencing data (fastq files) were first mapped to the human genome (hg19) (DNASTAR, Madison, Wis.). Read counts from the mapped sequence files were then binned into 60 kb windows (total 51672 genomic bins) and adjusted to the global mean count for each sample. The read count ratio in each genomic bin was calculated by dividing cfDNA with peripheral blood mononuclear cell germline DNA (gDNA) in the same patient [20]. The resulting ratios were further transformed with log 2 and corrected for GC content [42]. The fully normalized log 2 ratios in genomic bins were subjected to segmentation using the copy number analysis method (CNAM) algorithm (Golden Helix, Bozeman, Mont.).

5. Urine Genome Abnormality (UGA) Score Algorithm Calculation and Comparison with Plasma Genome Abnormality Score (PGA).

To quantify genomic abnormality, we improvised the previously reported methodology for calculating global genomic abnormalities in plasma by calculating a plasma genome abnormality (PGA) score [20]. This was performed by summing the most significant log 2 ratios in top 95-99% genomic bins. For the current study, we modified the genome abnormality calculation by summing log 2 ratios of ten most significant genomic segments. We removed genomic regions containing centromeres and their surrounding +/−1 Mb. We also excluded genomic segments that were ≤4 bin windows (4×60 kb). From the remaining segments, we summed the top ten most significant segment values (using absolute numbers) and defined the summarized number as Urine Genomic abnormality (UGA) score. We reanalyzed the previously reported PGA score [43] in the same manner as the UGA score for consistency and comparability. A higher score is indicative of a greater tumor DNA fraction in the cfDNA. To quantify a treatment response index in each patient, we defined the TEff (Treatment Efficacy) index as the log 2 ratio of UGA (or PGA) scores between the pre- and post-treatments: TEff index=log 2 (prePGA/postPGA)×100 and TEff index=log 2 (preUGA/postUGA)×100.

6. Statistical Analysis.

For defining hormone sensitive and castrate resistant stage in this hospital-based registry a uniform definition was used as reported previously [20, 44]. Briefly, for the CRPC cohort, overall survival was recorded from the date of first plasma collection after ADT failure to death or last follow-up. For the HSPC cohort, disease progression was recorded from the date of first plasma collection at initiation of ADT to disease progression or last follow-up. To evaluate association of the UGA score with overall survival in the CRPC sub-cohort, time from developing castrate resistance to death was considered and Kaplan-Meier analysis was performed for the UGA score and TEff index associations with overall survival (prognostic classifier). For the HSPC cohort time from initiating androgen deprivation therapy (ADT) for hormone sensitive stage to development of castrate resistance was obtained (predictive classifier). We dichotomized each sub cohort into two risk groups using median UGA score or TEff index as a cut-off. A P-value of ≤0.05 was considered statistically significant for statistical analysis.

F. References.

1. Siegel, et al., "Cancer statistics, 2015. CA: a cancer journal for clinicians." 2015; 65(1):5-29.
2. Sweeney, et al., "Chemohormonal therapy in metastatic hormone-sensitive prostate cancer." New England Journal of Medicine. 2015; 373(8):737-746.
3. Petrylak, et al., "Docetaxel and estramustine compared with mitoxantrone and prednisone for advanced refractory prostate cancer." New England Journal of Medicine. 2004; 351(15):1513-1520.
4. Tannock, et al., "Docetaxel plus prednisone or mitoxantrone plus prednisone for advanced prostate cancer." New England Journal of Medicine. 2004; 351(15):1502-1512.
5. Denis, et al., "Maximal androgen blockade: final analysis of EORTC phase III trial 30853." EORTC Genito-Urinary Tract Cancer Cooperative Group and the EORTC Data Center." Eur Urol. 1998; 33(2):144-151.
6. Eisenberger, et al., "Bilateral orchiectomy with or without flutamide for metastatic prostate cancer." New England Journal of Medicine. 1998; 339(15):1036-1042.
7. "Maximum androgen blockade in advanced prostate cancer: an overview of the randomised trials. Prostate cancer Trialists' Collaborative Group." Lancet. 2000; 355(9214):1491-1498.
8. De Bono, et al., "Abiraterone and Increased Survival in Metastatic Prostate cancer." New England Journal of Medicine. 2011; 364(21):1995-2005.
9. Kantoff, et al., "Sipuleucel-T immunotherapy for castration-resistant prostate cancer." New England Journal of Medicine. 2010; 363(5):411-422.
10. de Bono, et al., "Prednisone plus cabazitaxel or mitoxantrone for metastatic castration-resistant prostate cancer progressing after docetaxel treatment: a randomised open-label trial." The Lancet. 2010; 376(9747):1147-1154.
11. Ryan, et al., "Abiraterone in metastatic prostate cancer without previous chemotherapy." New England Journal of Medicine. 2013; 368(2):138-148.
12. Cabot, et al., "Increased survival with enzalutamide in prostate cancer after chemotherapy." New England Journal of Medicine. 2012; 367(13):1187-1197.
13. Snedecor, et al., "Denosumab versus zoledronic acid for treatment of bone metastases in men with castration-resistant prostate cancer: a cost-effectiveness analysis." Journal of medical economics. 2012; 16(1):19-29.
14. Fizazi, et al., "Denosumab versus zoledronic acid for treatment of bone metastases in men with castration-resistant prostate cancer: a randomised, double-blind study." Lancet. 2011; 377(9768):813-822.
15. Crowley, et al., "Liquid biopsy: monitoring cancer-genetics in the blood." Nat Rev Clin Oncol. 2013; 10(8): 472-484.
16. Kohli and Tindall, "New Developments in the Medical Management of Prostate cancer." Mayo Clin Proc. 2010; 85(1):77-86.
17. Attard, et al., "Selective inhibition of CYP17 with abiraterone acetate is highly active in the treatment of castration-resistant prostate cancer." Journal of clinical oncology: official journal of the American Society of Clinical Oncology. 2009; 27(23):3742-3748.
18. Diaz and Bardelli, "Liquid biopsies: genotyping circulating tumor DNA." J Clin Oncol. 2014; 32(6):579-586.
19. Heitzer, et al., "Circulating tumor DNA as a liquid biopsy for cancer." Clin Chem. 2015; 61(1):112-123.
20. Xia, et al., "Plasma genetic and genomic abnormalities predict treatment response and clinical outcome in advanced prostate cancer." Oncotarget. 2015.
21. Witte, et al., "Genomewide scan for prostate cancer-aggressiveness loci." American journal of human genetics. 2000; 67(1):92-99.

22. Kim, et al., "Integrative analysis of genomic aberrations associated with prostate cancer progression." Cancer research. 2007; 67(17):8229-8239.
23. Tindall, et al., "Comprehensive analysis of the cytokine-rich chromosome 5q31.1 region suggests a role for IL-4 gene variants in prostate cancer risk." Carcinogenesis. 2010; 31(10):1748-1754.
24. Porkka, et al., "RAD21 and KIAA0196 at 8q24 are amplified and overexpressed in prostate cancer." Genes, Chromosomes and Cancer. 2004; 39(1):1-10.
25. Tuupanen, et al., "The common colorectal cancer predisposition SNP rs6983267 at chromosome 8q24 confers potential to enhanced Wnt signaling." Nature genetics. 2009; 41(8):885-890.
26. Saramaki, et al., "Genetic aberrations in prostate cancer by microarray analysis." International Journal Of Cancer. 119(6):1322-1329, 2006.
27. Ellen, et al., "NDRG1, a growth and cancer related gene: regulation of gene expression and function in normal and disease states." Carcinogenesis. 2008; 29(1):2-8.
28. Wang, et al., "Down-regulation of Notch-1 and Jagged-1 inhibits prostate cancer cell growth, migration and invasion, and induces apoptosis via inactivation of Akt, mTOR, and NF-κB signaling pathways." J Cell Biochem. 109(4):726-736, 2010.
29. Bin Hafeez, et al., "Targeted knockdown of Notch1 inhibits invasion of human prostate cancer cells concomitant with inhibition of matrix metalloproteinase-9 and urokinase plasminogen activator." Clinical Cancer Research: an official journal of the American Association for Cancer Research. 2009; 15(2):452-459.
30. Cree, "Liquid Biopsy for Cancer Patients: Principles and Practice." Pathogenesis. 2015.
31. Antonarakis, et al., "AR-V7 and resistance to enzalutamide and abiraterone in prostate cancer." N Engl J Med. 2014; 371(11):1028-1038.
32. Kato and Janku, "Cell-free DNA as a novel marker in cancer therapy. Biomarkers in medicine." 2015; 9(7):703-712.
33. Botezatu, et al., "Genetic analysis of DNA excreted in urine: a new approach for detecting specific genomic DNA sequences from cells dying in an organism." Clin Chem. 2000; 46(8 Pt 1):1078-1084.
34. Lichtenstein, et al., "Circulating nucleic acids and apoptosis Annals of the New York Academy of Sciences. 2001; 945(1):239-249.
35. De Mattos-Arruda L, et al., "Circulating tumour cells and cell-free DNA as tools for managing breast cancer. Nature Reviews Clinical Oncology. 2013; 10(7):377-389.
36. Emile, et al., "Recurrent RAS and PIK3CA mutations in Erdheim-Chester disease." Blood. 2014; 124(19):3016-3019.
37. Diamond, et al., "Detection of an NRAS mutation in Erdheim-Chester disease." Blood. 2013; 122(6):1089-1091.
38. Zebisch and Jones, "ZNRF3/RNF43—A direct linkage of extracellular recognition and E3 ligase activity to modulate cell surface signalling. Progress in biophysics and molecular biology." 118: 112-118, 2015.
39. Nakata, et al., "Emerging role for leucine-rich repeat-containing G-protein-coupled receptors LGR5 and LGR4 in cancer stem cells." Cancer Management And Research. 6:171 2014.
40. Hsieh, et al., "MYC and metabolism on the path to cancer." Semin Cell Dev Biol. 43:11-21, 2015.
41. Robinson, et al., "Integrative clinical genomics of advanced prostate cancer." Cell. 2015; 161(5):1215-1228.
42. Diskin, et al., "Adjustment of genomic waves in signal intensities from whole-genome SNP genotyping platforms." Nucleic Acids Res. 2008; 36(19):e126.
43. Xia, et al., "Plasma genetic and genomic abnormalities predict treatment response and clinical outcome in advanced prostate cancer." Oncotarget. 2015; 6(18): 16411-16421.
44. Huang, et al., "Exosomal miR-1290 and miR-375 as prognostic markers in castration-resistant prostate cancer." Eur Urol. 2015; 67(1):33-41.

III. Algorithmic Approach for Determining the Plasma Genome Abnormality (23-PGA) and the Urine Genome Abnormality (23-UGA) Scores Based on cfDNA Copy Number Variations in Plasma And Urine: 23 Gene Set.

As described herein, the inventors demonstrate that genomic changes such as copy number variations, mutations, fusions, etc., attributable to prostate tumor-derived DNA are found in the cell free DNAs (cfDNA) fraction of plasma and urine in advanced stages of prostate cancer. Genomic variations in cfDNA found in plasma and urine were measured that are ascribable to tumors. Based on these measurements, a composite scoring algorithm, called Plasma Genomic Abnormality (PGA) and Urine Genomic Abnormality (UGA) was developed as described herein in section II, using a set of 10 genes. Data shown herein demonstrates that 10-PGA/10-UGA scores are associated with tumor burden and clinical outcomes in advanced prostate cancer patients. Therefore, variations in copy numbers of these 10 specific genes are the underlying basis for development of a predictive algorithm for clinical application.

For development of this method, in one embodiment, the following 23 gene set is used for measuring 23-UGA and 23-PGA scores. These genes were discovered associated with prostate cancer progression by 1) genomic (wide) sequencing and analyzing these results from cell free DNA collected in plasma and urine from a set of advanced prostate cancer patients as described in section II, then choosing a set of genes whose genome wide copy number variations are attributable to prostate cancer, for example, genetic areas of significant genomic aberrations at specific genomic loci that contain genes for prostate cancer development and progression that are found in both urine and plasma, and by 2) choosing certain genes that are implicated in prostate cancer biology. These 23-UGA and 23-PGA scores are derived from the data analyzed after performing whole genome sequencing and copy number analysis and then summing the total of the most significant genomic changes across the entire genome.

Based on the analysis of copy number variations observed in the data set obtained during the development of the present inventions and genes implicated in prostate cancer biology we have refined the gene list as below:
AR, PTEN, RB1, TNPRESS2, MYCL1, MYC, NOTCH1, TP53, ETSFusions, FOXA1, NKX3.1, ZBTB16, NCOR1, NCOR2, COL22A1, PIK3CA, PIK3B, PIK3R1, BRAF, RAF1, SPOP, APOB and SOX2.

For prediction of treatment outcomes based on copy number variations in the above genes in the advanced prostate cancer setting, we will employ the partial Cox regression method to develop a progression free survival (PFS) prediction model to the baseline (pre-treatment) sample of CNVs and then separately also to a second serial measurement to introduce covariance modeling for predicting clinical outcomes of treatments.

For the predictive model with two-time measures, the risk score (RS) in this predictive algorithm will be calculated as $$RS_i = \sum_{j=1}^{G} \beta_j X_{ij} + \beta_j^* D_{ij},$$

where G represents the number of candidate genes, $\beta_j$ represents the estimated coefficient of the jth gene, $X_{ij}$ represents baseline (i.e., pre-ADT) absolute log ratios (ALR) of the jth gene in sample i, $D_{ij}$ is the differences in ALR of gene j between pre-treatment and post-treatment initiation in sample I, and $\beta^*_j$ represents the estimated coefficient of $D_j$.

Validation of Predictive Model:

The algorithm derived from the partial Cox regression is contemplated for use to calculate the risk score for each patient in the validation set. This risk score is then contemplated to be associated with PFS using the Cox regression model. Thus, in one embodiment, each patient will be classified into high- or low-risk groups according to the risk score calculated as described herein. In one embodiment, the difference in PFS between risk groups will be assessed and contemplated for use with the log-rank test. In one embodiment, a time-dependent AUC-ROC will be used to test the time frame where the use of this risk score will increase predictive accuracy in the presence of other clinical variables, such as with other copy number variation methods described herein, PSA scores, clinical evaluations, circulating tumor cells (CTC), other diagnostic tests, and the like.

In one embodiment, the present invention provides a method, comprising: i) isolating a first cell free DNA sample from a prostate cancer patient prior to treatment; ii) sequencing said cell free DNA from said first sample so as to determine copy number variability as compared to a control; iii) calculating a first cfDNA Plasma Genomic Abnormality (PGA) Score based on said copy number variability; iv) treating said prostate cancer patient with Androgen Deprivation Therapy (ADT); v) isolating a second cell free DNA sample from said prostate cancer patient after said treating of step (iv); vi) sequencing said cell free DNA from said second sample so as to determine copy number variability as compared to a control; vii) calculating a second cfDNA Plasma Genomic Abnormality (PGA) Score; viii) comparing said first PGA score with said second PGA score; and ix) administering a chemotherapy composition to said subject when said second cfDNA Plasma Genomic Abnormality (PGA) Score is equal to or greater than said first cfDNA Plasma Genomic Abnormality (PGA) Score. In one embodiment, said second cfDNA Plasma Genomic Abnormality Score is obtained at least two weeks after initiating Androgen Deprivation Therapy. In one embodiment, second cfDNA Plasma Genomic Abnormality Score is obtained at least two months after initiating Androgen Deprivation Therapy. In one embodiment, said control comprises genomic DNA from said patient's lymphocytes.

IV. Genomic Abnormality of Urine Cell Free DNA and Plasma Cell Free DNA as Biomarkers in Advanced Prostate Cancer: Based Upon 15 Prostate Tumor Associated Genes.

In this embodiment, genome-sequencing data for 15 additional CRPC patients was added to the previous 10 CRPC patients. The following exemplary description is based on an expanded total set of samples from 25 CRPC patients.

This embodiment for a PGA algorithm was based upon 25 CRPC patient's plasma cfDNA samples obtained at the time of ADT failure. The read count of each gene was normalized by the read count from its matching germline DNA sample, after which a ratio was calculated which was further logged transformed (base 2). The analysis hereafter for resulting in the 15-gene panel is based on this absolute value of this log 2 ratio, termed as absolute log ratio (ALR).

Figure 24:
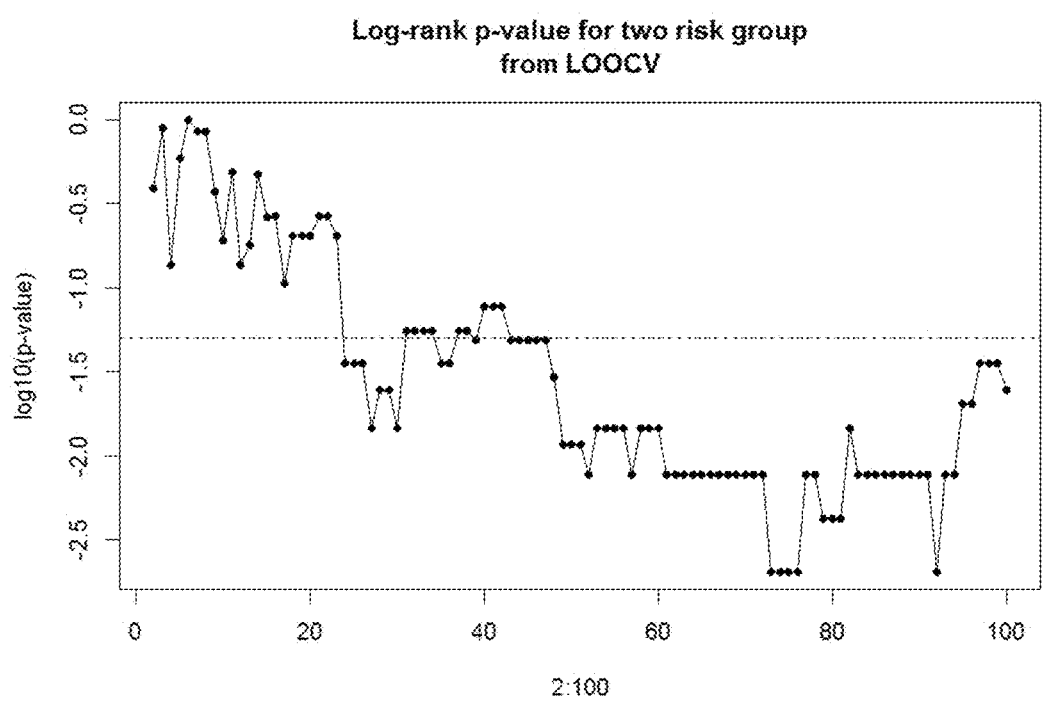
FIG. 24: shows exemplary V1 data for a two-risk group from LOOCV; log 10(p-value) vs. 2:100. LOOCV is based on the top 5,000 genes (Cox model from whole data).

For calculating a gene-based PGA score, first genes with length <10 kb and maximum ALR <0.6 were filtered out. Based on remaining genes from the whole genome scan, it was discovered that by using 60-90 genes, the high- and low-PGA groups show significantly differential association with overall survival (OS) (P=0.002 to approximately 0.004, log-rank test). Exemplary data is shown in FIG. 24 for LOOCV based on the top 5,000 genes, FIG. 25 for 4433 genes, and FIG. 26 for top 80 genes.

Figure 21:
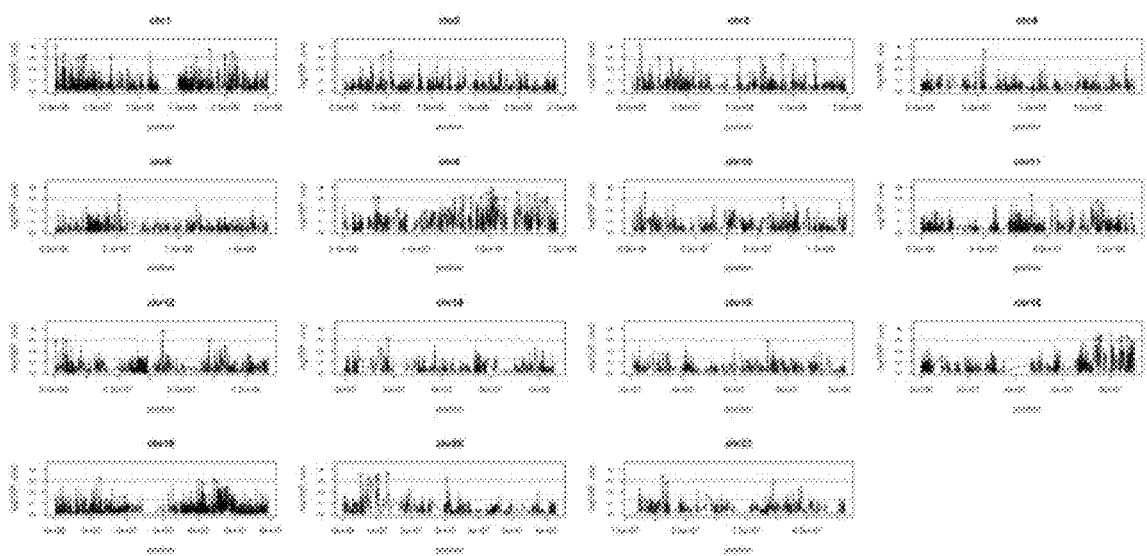
FIG. 21: shows an exemplary whole genome scan that revealed enrichment of survival-associated genes. X-axis demonstrates gene positions along each of 15 chromosomes with most significant gene association. Y-axis shows −log 10 p-values. Survival association shows clear clustering in certain chromosome regions (arms).

Thus, the entire set of 25 samples were used to identify the top 80 genes that showed discriminatory power for being associated with survival and with the smallest P-values (from Cox model). By examining chromosome positions of the selected genes, see FIG. 21, it was discovered that these genes were often enriched in certain chromosome regions such as chromosome 1 (15 genes), chr 3 (7 genes), chr 8 (20 genes), chr 16 (9 genes), and chr 20 (8 genes), especially in 1p (10 genes), 8q (18 genes), 16q (9 genes), and 20p (7 genes). FIG. 21: shows an exemplary whole genome scan that revealed enrichment of survival-associated genes. X-axis demonstrates gene positions along each of 15 chromosomes with most significant gene association. Y-axis shows −log 10 p-values. Survival association shows clear clustering in certain chromosome regions (arms). Cluster analysis further revealed strong correlation of their ALR values among genes in close-by genomic location, indicating sharing of genomic abnormality.

A. PGA Scores Including Top 80 Candidate Genes were Reduced Down to 13 Genes.

Based on this correlation structure and genomic information, the top 80 candidate genes were reduced down to 13 genes: ZDHHC18 (chr1), MRPS22, SAMD7 (chr3), DMTN, ZNF704, SPAG1, SNX31, SAMD12 (chr8), LOC101928197 (chr10), KLHDC4, SPG7, CHMP1A (chr16), PDRG1 (chr20). Due to importance of two other genes (PETN and RB1) from published literature and statistical significance of OS association in the dataset (Cox p<0.05) these two genes were included in the final PGA score calculation (total of 15 genes): 15-gene panel, e.g. 15-PGA score.

The PGA score based on the final 15 genes at the time of ADT failure show a more statistical strength for associations (i.e. correlations) with survival as the 15-gene PGA score was highly associated (correlated) with OS (FIGS. 22 and 23). FIG. 22: shows an exemplary scatter plot comparing a 15-gene-based PGA score vs. survival time among 25 CRPC patients. The higher PGA score is significantly associated with poor OS. Y-axis is PGA score. X-axis is follow-up time. P=5.88e-06. FIG. 23: shows an exemplary risk stratification (high PGA (red line) vs. low PGA (black line): median cut-off) using 15-gene PGA from LOOCV; survival probability vs. survival time (months). Kaplan-Meier analysis shows significant association of higher PGA score and shorter OS (HR=9.25, P=2.78E-05). As another way of determining OS, a Leave one out cross validation (LOOCV) value was calculated, as described in brief in Example IV, below. The LOOCV for risk prediction also showed significant difference in OS between the low and high PGA groups (P<0.0001, hazard ratio 9.25). In survival analysis, the hazard ratio (HR) refers to a ratio of hazard rates corresponding to conditions described by two levels of an explanatory variable. For example, in a population treated with a drug, the treated population may die at a different rate per unit time as the control population.

Thus, in one embodiment, genomic abnormalities in plasma and/or urine are contemplated for clinical application (use) in advanced prostate cancer patients. In some embodiments, a PGA and/or UGA score may be used to change a treatment, for example, start a treatment, stop a treatment or add one or more additional treatments. In other embodiments, a PGA and/or UGA score may be used to not change a treatment.

B. Optimization of PGA Score-Based upon a 15-Gene Panel.

Figure 25:
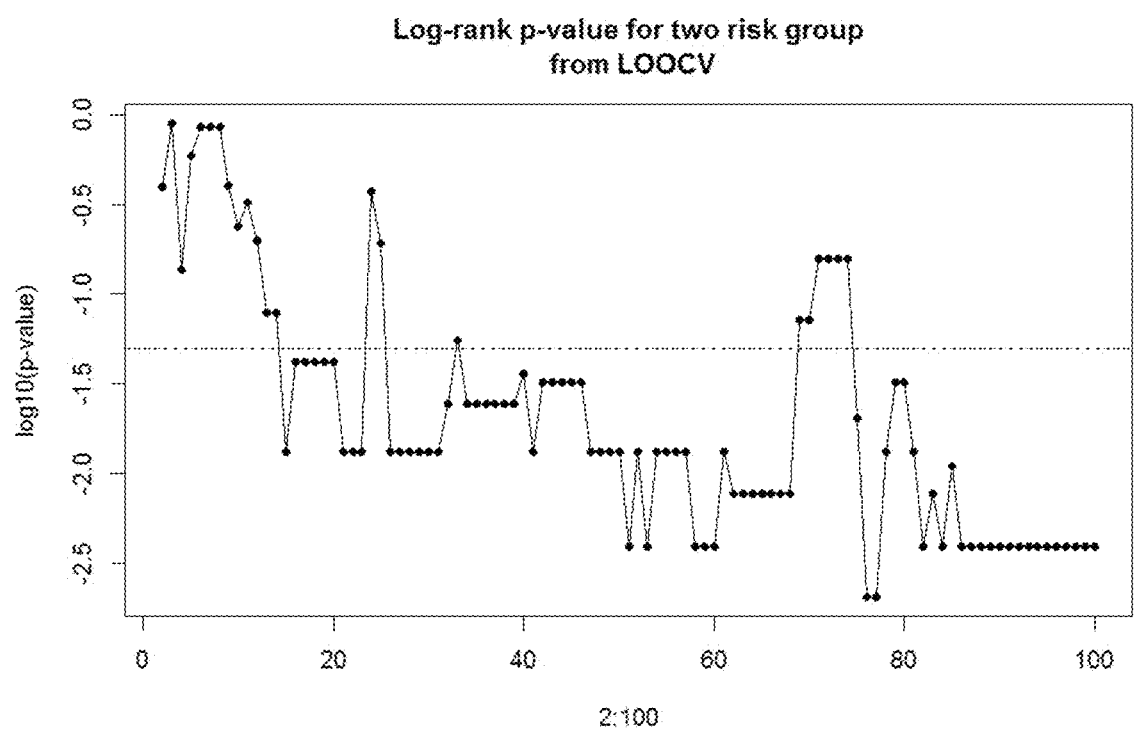
FIG. 25: shows exemplary data for a two-risk group from LOOCV; log 10(p-value) vs. 2:100. LOOCV is based on the 4433 genes with MAX>=25 and p<0.2 (Cox model from all data).
Figure 26:
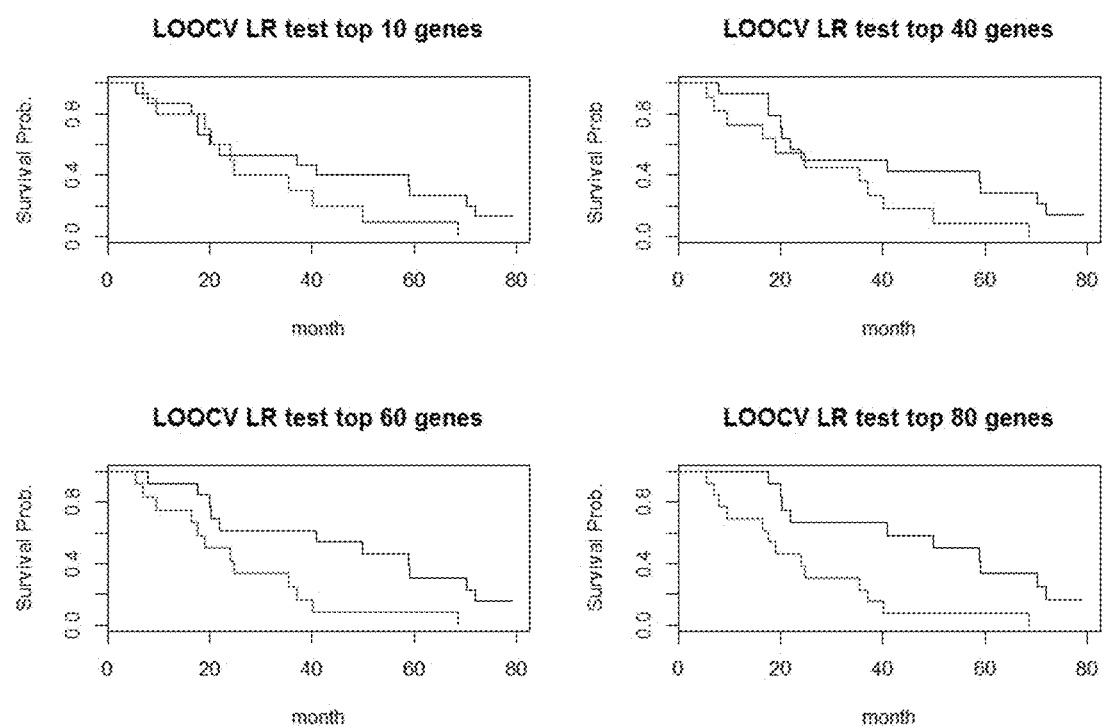
FIG. 26: shows an exemplary LOOCV LR (linear regression) test for A) top 10 genes. B) top 40 genes. C) top 60 genes and D) top 80 genes. P=0.0042 when K=80. P=0.0144 when K=60. Smallest P=0.002.

Optimization of the data obtained in this expanded preliminary dataset from 25 advanced prostate cancer patients indicates a use for a 15-gene panel derived from a top 80 gene group, as described above with supporting data shown in FIGS. 24-26. FIG. 24: shows exemplary V1 data for a two-risk group from LOOCV; log 10(p-value) vs. 2:100. LOOCV is based on the top 5,000 genes (Cox model from whole data). FIG. 25: shows exemplary data for a two-risk group from LOOCV; log 10(p-value) vs. 2:100. LOOCV is based on the 4433 genes with MAX>=25 and p<0.2 (Cox model from all data). FIG. 26: shows an exemplary LOOCV LR (linear regression) test for A) top 10 genes. B) top 40 genes. C) top 60 genes and D) top 80 genes. P=0.0042 when K=80. P=0.0144 when K=60. Smallest P=0.002.

However, additional genomic changes may be identified during sequencing of additional patient samples, and identified by adding new gene markers and deleting existing gene markers (e.g. gene markers in an exemplary gene panel described herein) in order to continue furthering "best" optimization for determining clinical outcomes. This continuous upgrade is typical in genomic-based tests, as more new information becomes known. Thus in additional embodiments, genes may be added or removed from the gene lists (panels) described herein. Regardless of the gene list used in predicting outcomes of prostate cancer treatment, the construction and evaluation of the PGA score, as described herein, will be used with modified gene lists.

C. Application of 15-Gene Panel.

The 15-gene panel described herein, is contemplated for use for predicting overall survival time of a prostate cancer patient. In some embodiments, a prostate patient is a HSPC. In some embodiments, a prostate patient is a CRPC. Thus in one embodiment, a PGA score is calculated using a 15-gene panel, e.g. 15-PGA score. In one embodiment, a UGA score is calculated using a 15-gene panel, e.g. 15-UGA score. In yet another embodiment, a 15-PGA/15-UGA score is calculated as described herein using a 15-gene panel. In one embodiment, a cfDNA sample is collected prior to treatment for use with a 15-gene panel. In one embodiment, a cfDNA sample is collected after treatment for use with a 15-gene panel. In yet another embodiment, a cfDNA sample is collected at the time of treatment failure, e.g. a time of ADT failure, for use with a 15-gene panel. In some embodiments, patients receiving ADT are also receiving chemotherapy. The use of a 15-gene panel enhances the prediction of clinical outcomes, such as survival time.

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); microM (micromolar); mol (moles); mmol (millimoles); micro.mol (micromoles); nmol (nanomoles); pmol (picomoles); g (grams); mg (milligrams); microg (micrograms); ng (nanograms); pg (picograms); L and (liters); ml (milliliters); microl (microliters); cm (centimeters); mm (millimeters); microm (micrometers); nm (nanometers); U (units); min (minute); s and sec (second); deg (degree); and ° C. (degrees Centigrade/Celsius).

Example I

This example describes the development of a predictive Plasma Genomic Abnormality (PGA) score based upon analysis of cell-free DNA from 2 blood samples collected from each patient, pre and post-treatment, in a set of prostate cancer patients. Plasma Genetic And Genomic Abnormalities Predict Treatment Response And Clinical Outcome In Advanced Prostate cancer. Xia, Kohli, Huang, Wang, et al., Oncotarget, Vol. 6, No. 18. Apr. 15, 2015.

A. Use of Liquid Biopsies During the Development of the Present Inventions.

Whole genome sequencing-based CNV and targeted sequencing-based mutational analysis in cfDNAs derived from a set of patients with advanced prostate cancer was done during the development of the present inventions. Tumor-related genomic abnormalities in plasma cfDNAs and their association with treatment response and clinical outcome was determined in relation to the patient's clinical status. In order to more precisely reflect tumor burden and estimate treatment response, two types of scoring algorithms were developed based on a composite score from the cfDNA genomic abnormality profiles. The results demonstrated herein, as shown below, indicate that non-invasive liquid biopsy technology can serve as a tool for personalized health-care management of advanced prostate cancer.

B. Observed Genomic Abnormalities and Total Genomic PGA Scores (T-PGA) from HSPC Prostate Cancer Patients Treated with ADT Alone or CRPC Patients Treated with ADT and Chemotherapy.

1. Overall cfDNA Genomic Abnormality in Advanced Prostate Cancer Patients.

We examined three samples for each patient including pre-treatment cfDNA, post-treatment cfDNA and matched lymphocyte-derived germline DNA (gDNA). Whole genome sequencing generated approximately 14.48 million (ranged from 9.19 to 21.72) mappable reads per sample and approximately 4,560 mappable reads per genomic bin window (1 Mb). CNV analysis using log 2 ratios between cfDNA and matched gDNA showed somatic genomic abnormalities in the 20 patients tested. Overall, we observed more genomic abnormalities in the CRPC cohort undergoing chemotherapy than in the HSPC cohort receiving ADT alone (FIG. 7).

To further define the CNVs, we performed a detailed analysis at chromosomal regions showing frequent aberrations in prostate cancer. Among these, the genomic region at the androgen receptor (AR) was most frequently reported to be amplified (Koivisto, et al., "Androgen Receptor Gene Amplification: A Possible Molecular Mechanism for Androgen Deprivation Therapy Failure in Prostate Cancer." *Cancer Res*, 57:314-319 1997; Taplin and Balk, "Androgen Receptor: A Key Molecule in the Progression of Prostate Cancer to Hormone Independence." *J Cell Biochem*, 91:483-490 2004). To examine the amplification status, we zoomed into the genomic region containing AR and observed AR locus amplification in 1 of 10 HSPC (#1080) and 3 of 10 CRPC cases (#1010, #1043 and #1060) (FIG. 1).

Another common genomic aberration in prostate cancer was various fusion genes at the TMPRSS2 locus (Loeb, et al., "Active Surveillance for Prostate Cancer: A Systematic Review of Clinicopathologic Variables and Biomarkers for Risk Stratification." *Eur Urol,* 67:619-626 2015; Yao, et al., "Evaluation of the Tmprss2:Erg Fusion for the Detection of Prostate Cancer: A Systematic Review and Meta-Analysis." *Tumour Biol,* 35:2157-2166 2014). We observed two CRPC patients (#1003 and #1005) with genomic loss and two patients with genomic gain-one CRPC patient (#1060) and one HSPC patient (#1050). Both genomic losses resulted in the TMPRSS2-ERG fusion gene (FIG. 1). The genomic loss at the TMPRSS2 locus was present in two CRPC patients with a pathological diagnosis of small cell carcinoma (neuro-endocrine origin). These two patients did not show AR amplification. The third most common genomic abnormality was PTEN deletion (Phin, et al., "Genomic Rearrangements of Pten in Prostate Cancer." *Front Oncol,* 3:240 2013; Yoshimoto, et al., "Pten Genomic Deletions That Characterize Aggressive Prostate Cancer Originate Close to Segmental Duplications." *Genes Chromosomes Cancer,* 51:149-160 2012), which was detected in four CRPC cases (#1003, #1005, #1014 and #1060) but not in any of the HSPC cases (FIG. 1).

2. Plasma Genomic Abnormality (PGA) Score and its Clinical Association.

To quantify the tumor DNA fraction in cfDNA, we summed the squared 95th-99th absolute log 2 ratios as the PGA score. Similar to gross chromosomal abnormality, the PGA scores were significantly higher in the CRPC cohort than in the HSPC cohort (FIG. 2). To estimate potential association of PGA scores with overall survival, we performed Cox regression analysis in 19 of the 20 patients with complete follow-up data. We found that elevated PGA scores in pre-treatment samples were significantly associated with short survival (p=0.01, 95% CI=1.01-1.08). We also observed this association in post-treatment samples (p=0.04, 95% CI=1.00-1.20). Among the 20 patients, 7 were classified as having high volume disease (Table 1), defined by the presence of either a visceral (non-lymph nodal) metastasis or >4 bone lesions with at least one present outside the spine or pelvis skeleton at the time of initiating chemotherapy for the CRPC stage. Five of the 7 high volume cancer patients showed high initial PGA scores (cutoff value >10) but only 1 of 13 low volume patients demonstrated high initial PGA score (p=0.005, unpaired t test) (FIG. 3).

For the 10 HSPC patients undergoing ADT, PGA score changes between treatments were minor. This was attributable to relatively low tumor burden in this group of patients. After a median follow-up time of 53.8 months (range 42-95 months), only one patient (#1054) was deceased due to disease. This patient showed relatively high PGA scores in both pre- and post-ADT in the HSPC cohort (FIG. 2). For the 10 CRPC patients receiving chemotherapy, the patients with the highest initial PGA score included #1003, 1005 and 1060. These three patients died with relatively short survival time. To estimate patients' response to treatment, we calculated their Treatment Efficacy (TEff) indexes by transforming PGA score differences between pre- and post-treatments (see method section). We found that the TEff indexes in patients 1003, 1005, and 1060 were 2, 8, and 42, respectively. Correspondingly, their overall survival times were 6, 9 and 18 months (FIG. 4).

3. Cancer Gene Mutational Profiles.

To identify somatic mutations in cfDNAs, we performed the targeted sequencing of 578 cancer-related genes in the 20 patients. The average mapped reads per patient was 14.46 million (range 9.11-19.74) with 44% of reads on target (range 41-48%). Sequences of the samples achieved a mean coverage of 79× (range 54-87). Among 10 HSPC patients, we identified somatic mutations in 66 genes in pre-ADT and 68 genes in post-ADT samples after removing constitutional polymorphisms (cfDNA vs. matched gDNA). Of these mutated genes, 17 were shared between pre- and post-treatment samples. Among 10 CRPC patients, we identified somatic mutations in 52 genes in pre-chemotherapy and 63 genes in post-chemotherapy samples, of which 18 genes were shared (Supplementary Tables S1-S4). To validate these mutations, we applied allele-specific PCR (AS-PCR) to examine 26 mutations in 41 samples with mutations found by sequencing technology. AS-PCR successfully confirmed 20 of these mutations (FIG. 8). The remaining 6 mutations were uncertain due to difficulty in establishing high quality AS-PCR assays.

4. Gene Mutation Profile Changes Between Pre- and Post-Treatment.

To examine treatment-associated pathway alterations, we analyzed the two patient cohorts separately. Overall, we observed 34 and 35 pathways showing >3 gene differences between pre- and post-treatment samples in the HSPC and CRPC cohorts, respectively. Compared to pre-treatment samples, mutations in post-treatment samples were more diverse, reflecting more pathways involved. For HSPC patients, we observed more gene mutations in post-than in pre-treatment samples in these pathways (FIG. 5). The genes involving androgen biosynthesis and metabolism including androgen signaling, estrogen receptor signaling and GNRH signaling pathways were among the most commonly mutated. For example, GNRH signaling pathway is a target of ADT and contains 22 genes. Of those, only 1 gene mutation was detected before ADT with 7 gene mutations detected after ADT.

For CRPC patients, 20 of 35 pathways had gene mutations in post-treatment patients, not in the pretreatment patients. The most common mutations in the post-treatment group included axonal guidance signaling, protein kinase A signaling and renin-angiotensin signaling pathways. Meanwhile, 6 pathways showed less gene mutations in post-than in pre-treatment samples (FIG. 6). The most common mutations before chemotherapy occurred in DNA repair-related hereditary breast cancer signaling genes. Among 41 genes in the pathway, 7 mutations were detected in the pre-treatment while merely 1 mutation was found in the post-treatment samples.

C. Summary.

Cancer is characterized by massive genomic abnormalities, some of which are targets for therapy or are used for monitoring response to specific treatments. Recent studies have reported that genomic abnormalities in cfDNA resemble genomic signatures of primary tumors in human cancers (Crowley, et al., "Liquid Biopsy: Monitoring Cancer-Genetics in the Blood." *Nat Rev Clin Oncol,* 10:472-484 2013; Diaz and Bardelli, "Liquid Biopsies: Genotyping Circulating Tumor DNA." *J Clin Oncol,* 32:579-586 2014; Farris and Trimarchi, "Plasma-Seq: A Novel Strategy for Metastatic Prostate Cancer Analysis." *Genome Med,* 5:35 2013; Heitzer, et al., "Tumor-Associated Copy Number Changes in the Circulation of Patients with Prostate Cancer Identified through Whole-Genome Sequencing." *Genome Med,* 5:30 2013). In this study, we examined plasma cfDNAs in advanced prostate cancer and were able to detect somatic mutations and genomic aberrations in the patient groups after accounting for constitutional genomic abnormalities. These aberrations were often different between pre- and post-treatment, reflecting dynamic genomic evolution during stage-specific therapies.

Our results indicate that somatic alterations in cfDNA may serve as sensitive biomarkers for predicting treatment response and clinical outcome in advanced prostate cancer. To examine the repertoire of genomic aberrations in tumor tissues, biopsies are often performed. However, tissue biopsy in advanced prostate cancer is challenging because bone metastasis are predominant. Many patients do not have residual disease at their primary site due to surgical removal of the prostate. Biopsies at sites of bone or nodal metastasis are invasive, morbid, and inaccurate. These biopsies are subject to sampling bias and may not represent the overall tumor mass. Due to these limitations, liquid biopsy by sensitive detection of tumor components has emerged as an attractive alternative option. This approach is minimally invasive and can be more frequently scheduled in clinical laboratories. Because blood stream contains the cfDNAs derived from the tumor sites, the liquid biopsy assay may detect more complete repertoire of tumor genome variations (Chan, et al., "Cancer Genome Scanning in Plasma: Detection of Tumor-Associated Copy Number Aberrations, Single-Nucleotide Variants, and Tumoral Heterogeneity by Massively Parallel Sequencing." Clin Chem, 59:211-224 2013; Crowley, et al., "Liquid Biopsy: Monitoring Cancer-Genetics in the Blood." Nat Rev Clin Oncol, 10:472-484 2013; Diaz and Bardelli, "Liquid Biopsies: Genotyping Circulating Tumor DNA." J Clin Oncol, 32:579-586 2014; Farris and Trimarchi, "Plasma-Seq: A Novel Strategy for Metastatic Prostate Cancer Analysis." Genome Med, 5:35 2013; Heitzer, et al., "Tumor-Associated Copy Number Changes in the Circulation of Patients with Prostate Cancer Identified through Whole-Genome Sequencing." Genome Med, 5:30 2013).

It was shown that tumor genomic abnormalities were well reflected in cfDNA during cancer progression (Heitzer, et al., "Tumor-Associated Copy Number Changes in the Circulation of Patients with Prostate Cancer Identified through Whole-Genome Sequencing." Genome Med, 5:30 2013; Leary, et al., "Detection of Chromosomal Alterations in the Circulation of Cancer Patients with Whole-Genome Sequencing." Sci Transl Med, 4:162ra154 2012). By comparing the differences between multiregional sequencing of 2 synchronous cancer tissues and shotgun sequencing of cfDNA, Chan, et al., (Chan, et al., "Cancer Genome Scanning in Plasma: Detection of Tumor-Associated Copy Number Aberrations, Single-Nucleotide Variants, and Tumoral Heterogeneity by Massively Parallel Sequencing." Clin Chem, 59:211-224 2013), show that cfDNA sequencing is able to detect genomic variations originated from different tumor sites. Recently, Schutz, et al. (Schutz, et al., "Chromosomal Instability in Cell-Free DNA Is a Serum Biomarker for Prostate Cancer." Clin Chem, 61:239-248 2015), found that cfDNA genomic variations are able to distinguish both benign prostatic hypertrophy and prostatitis from prostate cancer with accuracy of 90%. Clearly, liquid biopsy may provide a useful tool for cancer detection, monitoring and research.

To estimate tumor DNA content, previous studies applied "genomewide z-score" (Leary, et al., "Detection of Chromosomal Alterations in the Circulation of Cancer Patients with Whole-Genome Sequencing." Sci Transl Med, 4:162ra154 2012) or "PA-score" (Heitzer, et al., "Tumor-Associated Copy Number Changes in the Circulation of Patients with Prostate Cancer Identified through Whole-Genome Sequencing." Genome Med, 5:30 2013). However, these algorithms may not accurately reflect tumor DNA contribution to cfDNA because tumor genomes are not always altered in the genome segments.

In addition, calculations of these scores require cfDNAs derived from a group of normal individuals as reference controls. Due to the germline-determined CNVs pre-existing in any given individual, these algorithms may generate significant bias toward the regions with pre-existing CNVs. To address this issue, we normalized cfDNA read counts using lymphocyte gDNA read counts from the same patient, significantly minimizing the biases caused by pre-existing CNVs. Additionally, we developed the PGA scoring system by summing the most significant genomic regions, avoiding potential background noises from other scoring algorithms. Our data show that PGA scores and TEff indexes are potentially useful to assess treatment response and overall survival.

Targeted sequencing in cfDNA has demonstrated potential clinical utility in guiding selection of targeted therapies (Narayan, et al., "Ultrasensitive Measurement of Hotspot Mutations in Tumor DNA in Blood Using Error-Suppressed Multiplexed Deep Sequencing." Cancer Res, 72:3492-3498 2012). By analyzing mutational profiles before and after initiating ADT, we were able to detect increased mutant genes after approximately 4 months of ADT in several pathways, including protein kinase A signaling, the PPARα/RXRα activation and GNRH signaling pathways. These pathways are associated with AR activation (Nazareth and Weigel, "Activation of the Human Androgen Receptor through a Protein Kinase a Signaling Pathway." J Biol Chem, 271:19900-19907 1996) and androgen biosynthesis (Limonta and Manea, "Gonadotropin-Releasing Hormone Receptors as Molecular Therapeutic Targets in Prostate Cancer: Current Options and Emerging Strategies." Cancer Treat Rev, 39:647-663 2013). One mutated gene in these pathways is EP300, a gene for prostate cancer cell proliferation (Heemers, et al., "Androgen Deprivation Increases P300 Expression in Prostate Cancer Cells." Cancer Res, 67:3422-3430 2007) and hormone responsiveness of AR (Choi, et "Procyanidin B3, an Inhibitor of Histone Acetyltransferase, Enhances the Action of Antagonist for Prostate Cancer Cells Via Inhibition of P300-Dependent Acetylation of Androgen Receptor." Biochem J, 433:235-244 2011). We also found more gene mutations in the glucocorticoid receptor (GR) signaling pathway after ADT. GR expression is stimulated by castration therapy, a mechanism that compensates for AR signaling blockade and promotes CRPC progression (Arora, et al., "Glucocorticoid Receptor Confers Resistance to Antiandrogens by Bypassing Androgen Receptor Blockade." Cell, 155:1309-1322 2013; Xie, et al., "The Expression of Glucocorticoid Receptor Is Negatively Regulated by Active Androgen Receptor Signaling in Prostate Tumors." Int J Cancer, 136:E27-38 2014). Currently, preclinical models are often used to define the mechanisms of resistance to a specific treatment, but it is generally difficult to confirm these findings in clinical samples. Our results suggest that the cfDNA-based genetic analysis described herein, provide a superior approach for studying and predicting tumor resistance in real patient samples.

Many mutations detected after treatments were not present in pre-treatment samples. These non-overlapping mutations are of interest as they may provide novel insights into the evolution of tumor genomes in response to therapy or serve as predictive biomarker for treatment response and/or prognostic biomarkers for survival. For example, mutations in PRKAR1A and NFKB2 were found after chemotherapy treatment. PRKAR1A is functionally linked to AR during the progression of prostate cancer (Sarwar, et al., "Protein Kinase A (PKA) Pathway Is Functionally Linked to Androgen Receptor (Ar) in the Progression of Prostate Cancer."

*Urol Oncol,* 32:25 e21-12 2014). Its overexpression is observed in advanced prostate cancer (Merkle and Hoffmann, "Roles of Camp and Camp-Dependent Protein Kinase in the Progression of Prostate Cancer: Cross-Talk with the Androgen Receptor." *Cell Signal,* 23:507-515 2011; Sarwar, et al., "Protein Kinase A (PKA) Pathway Is Functionally Linked to Androgen Receptor (Ar) in the Progression of Prostate Cancer." *Urol Oncol,* 32:25 e21-12 2014) and may cause resistance to chemotherapy (Loilome, et al., "Prkar1a Is Overexpressed and Represents a Possible Therapeutic Target in Human Cholangiocarcinoma." *Int J Cancer,* 129: 34-44 2011). NFKB can be activated by the chemotherapy drug (docetaxel) and contributes to treatment resistance in prostate cancer (Codony-Servat, et al., "Nuclear Factor-Kappa B and Interleukin-6 Related Docetaxel Resistance in Castration-Resistant Prostate Cancer." *Prostate,* 73:512-521 2013; Marin-Aguilera, et al., "Epithelial-to-Mesenchymal Transition Mediates Docetaxel Resistance and High Risk of Relapse in Prostate Cancer." *Mol Cancer Ther,* 13:1270-1284 2014; O'Neill, et al., "Characterisation and Manipulation of Docetaxel Resistant Prostate Cancer Cell Lines." *Mol Cancer,* 10:126 2011). These results are consistent with the common notion that stage-specific therapies increase tumor cell subpopulations carrying treatment-resistant mutations and proportionally reduce cell subpopulations carrying treatment-sensitive mutations.

In summary, next generation sequencing was used to test cfDNAs for somatic variations in advanced prostate cancer. We developed a new scoring algorithm to estimate tumor DNA burden and predict patient's response to a specific therapy. We found that genetic and genomic profile changes after treatments are clinically and biologically associated with response to stage-specific therapies. Although the study examined a limited number of patients, the results from this study strongly support that DNA-based liquid biopsy has great potential to serve as alternative means to examine tumor genetic changes in advanced prostate cancer. Further studies are needed to evaluate the clinical utility of cfDNA as useful biomarker to predict treatment response and clinical outcomes.

D. Materials and Methods.

The following are exemplary materials and methods used during the development of the present inventions.

1. Sample Collection.

Plasma specimens from two separate cohorts of advanced prostate cancer patients were randomly selected from a hospital-based registry for biomarker development in advanced prostate cancer. Details of patient enrollment have been previously reported (Huang, et al., "Exosomal Mir-1290 and Mir-375 as Prognostic Markers in Castration-Resistant Prostate Cancer." *Eur Urol,* 67:33-41 2015). The plasma was derived from EDTA-treated blood. Plasma was separated within 2 hours after blood draw and frozen immediately at −80° C. without a freeze-thaw cycle before use. Patient characteristics are presented in Table 1. Each patient provided plasma collected just before treatment and plasma collected approximately four months after initiating stage-specific therapy. The treatments were initiated after collection of the first specimen. Castration levels of testosterone (total testosterone <50 ng/dl) were confirmed at the time of the second sample collection. This study was approved by Institutional Review Boards at both the Medical College of Wisconsin and Mayo Clinic.

2. DNA Extraction And Sequencing Library Preparation.

Blood plasma samples underwent a second centrifugation at 3000 rpm for 10 min before DNA extraction. The cfDNAs were extracted from 400-800 µl of plasma using QIAamp DNA Blood Mini Kit (QIAGEN, Valencia, Calif., USA). The final DNA eluent (50 µl) was quantified by a Qubit 2.0 Fluorometer (Life Technology, Carlsbad, Calif., USA) and stored at −80° C. until use. DNA libraries were prepared using a NEXTflex DNA-Seq Kit (BIOO Scientific Corporation, Austin, Tex., USA). Libraries were pooled for paired-end sequencing on a HiSeq2000 Sequencing System (Illumina, San Diego, Calif., USA).

3. CNV Calculation.

Raw sequencing data (fastq files) were first mapped to the human genome (hg19) (DNASTAR, Madison, Wis.). Read counts from the mapped sequence files were then binned into 1 Mb windows (total 3113 genomic bins) and adjusted to the global mean count for each sample. The read count ratio in each genomic bin was calculated by comparing cfDNA to lymphocyte gDNA derived from the same patient to account for constitutional CNVs. The resulting ratios were further log 2 transformed and corrected for GC content (Diskin, et al., "Adjustment of Genomic Waves in Signal Intensities from Whole-Genome Snp Genotyping Platforms." *Nucleic Acids Res,* 36:e126 2008). The fully normalized log 2 ratios in genomic bins were subjected to segmentation using the copy number analysis method (CNAM) algorithm (Golden Helix, Bozeman, Mont.).

4. PGA Score and TEff Index.

To quantify the genomic abnormality and facilitate comparison between different samples, we defined the ith percentile of absolute log 2 ratios (ALRs) as ALR.i and calculated the sum of the squared ALRs between ALR.95 and ALR.99, where ALR.95 was considered as the minimum threshold of genomic abnormality. We named this summed value "Plasma Genomic Abnormality (PGA) score". A higher score indicates greater tumor DNA fraction in the cfDNA. The top one percentile ALRs were excluded to avoid over-estimation of genomic abnormalities because some samples showed extensive CNVs at telomere or centromere regions (FIG. 9). Although we did not exclude possibility of true CNV changes (for example, gene amplification), we believe that the extreme CNV changes in the regions were more likely caused by high sequence homologs and relatively low quality sequencing libraries. To quantify treatment response in each patient, we defined the TEff (Treatment Efficacy) index as the log 2 ratio of PGA scores between the pre- and post-treatments: TEff index=log 2(prePGA/postPGA)×10. A TEff index of less than or close to zero indicates no response to treatment while a higher TEff index is indicative of a better treatment response.

5. Targeted Sequencing.

The Comprehensive Cancer Panel (Roche NimbleGen, Madison, Wis.) was used for targeted sequencing. The panel covers 4 Mb genomic sequences and targets 578 cancer-related genes. The genes were captured from sequencing libraries made for CNV analysis according to Roche NimbleGen's manual. Final enriched libraries were subjected to 100 bp PE sequencing on a HiSeq2000 Sequencing System. Gene mutations were detected by comparing cfDNA to lymphocyte gDNA in the same patient with 2% variant alleles as the cutoff for mutation calls. HMGC Sequencing Core at Medical College of Wisconsin provided DNA sequencing service and Great Lakes Genomics Center for provided the computational resources.

6. Allele Specific PCR.

Allele specific PCR (AS-PCR) was used to validate sequencing-detected mutations. For each mutation, three primers were designed with one common primer and two mutant-specific primers. Reactions were performed in a 250 reaction with 4 ng of 1.5 pre-amplified DNA and 0.5 unit of Taq DNA polymerase (New England Biolab, Ipswich, Mass.). This DNA polymerase does not have 3'-5' exonuclease activity and therefore is suitable for AS-PCR. Amplifications were carried out in a thermal cycler (Eppendorf Mastercycler pro S) including initial denaturation for 60 sec at 95° C., 40 cycles of denaturation for 30 sec at 95° C., annealing for 30 sec at primer-dependent temperatures (Supplementary Table 55), and extension for 40 sec at 72° C.

7. Mutation Pathway Enrichment Analysis.

To examine the functional classifications of mutant genes, we applied Ingenuity Pathway Analysis (IPA, Qiagen, Calif.) and treated the 578 cancer-related genes as background reference. For mutant genes, we searched for mutational profile differences between pre- and post-treatment samples. We defined >3 gene differences in a specific pathway between pre- and post-treatments as the cutoff for mutational profile changes. This analysis was useful to determine pathways that respond to stage-specific therapy.

Example II

This example describes the development of a predictive Urine Genomic Abnormality (UGA) scores and Plasma Genomic Abnormality (PGA) scores based upon analysis of 10 genes isolated from cell-free DNA from both urine and blood samples collected from a set of prostate cancer patients. Additionally, observations of genetic abnormalities discovered in the patient's cell-free DNA samples are shown.

As shown herein, a urine score (UGA) from the 10 gene analysis is a better predictor of outcome than plasma scoring (PGA) from the 10 gene analysis for HSPC patients, see FIG. 18 C vs. D. Thus in one embodiment, the 10 gene urine score provides an earlier outcome prediction by at least one or more months, up to 6.9, up to 20.6, up to 34.3 months, for predicting a faster disease progression in the HSPC patients with low disease than the 10 gene plasma score. In contrast, in one embodiment, the 10 gene plasma score provides an earlier outcome prediction 10 gene urine score by at least one or two months, for predicting a faster disease progression in the HSPC patients with high disease. For the CRPC patients, in one embodiment, the 10 gene plasma score provides an earlier outcome prediction between seven months and 21 months, than the 10 gene urine score for predicting a faster disease progression in the CRPC patients with high disease.

A. Observed Genomic Abnormality of Urine Cell Free DNA and Plasma Cell Free DNA in Patients Having Advanced Prostate Cancer as HSPC Prostate Cancer Patients Treated with ADT Alone or CRPC Patients Treated with ADT and Chemotherapy.

1. Patients' Clinical Characteristics.

Matched urine specimens for patients with previous cfDNA sequencing of plasma specimens were available for 9 of 10 hormone sensitive prostate cancer (HSPC) patients and the ten patients with castrate resistant prostate cancer (CRPC) disease. These samples were selected for cfDNA purification and profiling. Patient characteristics for these two advanced cancer cohorts are presented in Table 1U. Each subject had two serial urine specimens available before and after initiating stage-specific treatments. Patients in the HSPC sub cohort underwent continuous ADT and for the CRPC sub cohort received docetaxel chemotherapy which was added to ADT as a standard of care treatment. The mean time between two sample collections in the HSPC was 128 days, and the mean time between two sample collections in the CRPC was 112.4 days. The median follow up study time was and 64.00 months (40.93-69.13 months) and 20.97 months (range 6.77-72.83 months) for HSPC and CRPC the cohorts respectively.

2. Urine cfDNA Yield and Quality.

To assess cfDNA yield, we tested three different kits using one single urine sample. We found that average cfDNA yields were 5.63 ng, 6.46 and 13.27 ng for Zymo, Norgen and Analytik, respectively (FIG. 10). The Analytik kit generated approximately 2 fold more cfDNA than two other kits. Due to relatively high yield, 2 ng cfDNAs extracted using the Analytik kit was directly used for sequencing library construction. However, qualities of the sequencing libraries made from Analytik-derived cfDNA were extremely poor in three separate evaluation tests as determined by lack of featured library fragment band at approximately 300-310 bp. Meanwhile, cfDNAs derived from Zymo kit generated consistent high quality sequencing library in three separate evaluation tests (FIG. 11).

3. Urine cfDNA and Sequencing Library Quality.

The final cfDNA yield from 15 ml urine samples ranged from undetectable (<0.02 ng/ul) to 1.6 ng/ul in 10 ul elution buffer. Among 19 patients with both pre and post-treatment urine specimen detectable cfDNAs was measurable in 33 of the 38 samples. cfDNA yields from the remaining 5 samples were too low for measurement. For the 33 samples with total cfDNA >0.25 ng, sequencing libraries were prepared with final concentration of library DNAs between 0.878 and 3.490 ng/ul. High sensitivity DNA chip showed multiple library fragments with peak size at approximately 300 bp (FIG. 11). Whole genome sequencing generated approximately 7.6 million (ranged from 4.3 to 15.2) raw reads and 6.9 million (ranged from 3.7 to 14.0) mappable reads. Corresponding mappable reads were observed from 77 to 93 percent of raw reads. The mean read count was approximately 134 per 60 kb genomic window (Table 2U).

4. Overall Urine cfDNA Genomic Abnormalities.

To evaluate genomic abnormality, for each genomic bin, log 2 ratios between read counts from urine cfDNA and lymphocyte-derived genomic DNA (gDNA) in the same patient were calculated. Fragmentation-based CNV analysis showed that genomic abnormalities were detectable in the cfDNAs in the 19 patients tested. A greater number of genomic abnormalities were observed in the CRPC sub cohort undergoing chemotherapy than in the HSPC cohort receiving ADT alone. In fact, four of 10 CRPC patients (1003, 1004, 1014, 1017) and 2 of 9 HSPC patients (1050 and 1059) showed significant genomic abnormalities. Of the 33 successfully sequenced cfDNA specimens, five patients had either a pre- or post-treatment specimen cfDNA only while remaining 14 patients had both pre- and post-treatment cfDNAs. Among these 14 patients with paired samples, seven belonged to the HSPC sub cohort and other seven to the CRPC sub cohort. For these 14 patients, we performed unsupervised clustering analysis using log 2 ratios in each genomic window and found that 11 pairs were clustered together (FIG. 12). Among those, some samples such as patients 1050 and 1104 demonstrated significant CNV intensity differences between pre- and post-treatments. By comparing cfDNA based CNVs from urine and plasma in matched patient samples, we observed consistent tumor-associated CNVs, although differences in the degree of changes in the two specimen types was observed (FIG. 13).

5. Genomic Abnormalities at Specific Loci.

To further define genomic abnormalities in urine, we performed detailed analysis at chromosomal regions with putative and frequent aberrations in prostate cancer. Among those, genomic region at androgen receptor (AR) is most frequently amplified in CRPC stage. To examine the amplification status, we zoomed to the genomic region containing AR and observed AR locus amplification in five of ten CRPC cases (#1003, #1005, #1010, #1017, and #1043) but none in nine HSPC cases. Although the amplicon boundaries varied they contained whole AR gene. Another common genomic aberration in prostate cancer is at TMPRSS2 locus where frequent rearrangements create various fusion genes. We observed urine TMPRSS2 genomic variations in four cases with CRPC (#1003, #1005, #1014 and #1017) and 2 cases with HSPC (#1040, and #1098). The breakpoints for two genomic losses occurred at the two gene (ERG and TMPRSS2) regions, therefore forming a TMPRSS2-ERG fusion gene. The third most common genomic abnormality observed in prostate cancer is PTEN gene deletion. We found the PTEN loss in 4 cases of our CRPC sub cohort (#1002, #1005, #1043 and #1060) and one case of HSPC (#1080) in the urine cfDNAs. Additionally, we found NOTCH1 locus amplification in one CRPC patients (#1014) and four HSPC patients (#1050, #1059, #1084 and #1098). Most of these abnormalities in urine cfDNAs were also observed and previously reported in the matched plasma cfDNAs [20] (FIG. 14 and Table 3U). Other chromosomal regions were also frequently altered in the tested samples with most having at least one common deletion or amplification per chromosome. From the common regions, we further defined the minimally overlapped regions which were involved in amplifications at 8q24.3, 9q34.3, 11p15.5 and 14q11.2 and deletions at 4q35.2, 5q31.3, 7q36.3, 12q24.33, and 16p11.2 (Table 4U). Among those, 7 regions including 5q31.3, 7q36.3, 8q24.3, 9q34.3, 11p15.54, 14q11.2 and 16p11.2 were reported to be associated with prostate cancer [21-26]. Meanwhile, gene mutations at these loci have also been reported in prostate cancer tissues [27-29]. In addition, frequent "amplification" at TCRA locus was observed in most urine samples. Because extensive rearrangements (deletions) at TCRA locus during T cell development, lymphocyte-derived gDNA may harbor partial deletions at this locus. Using such gDNAs as controls to normalize cfDNA may generate false positive amplification at this locus (FIG. 15).

6. Urine Genomic Abnormality (UGA) Score and its Clinical Association.

As described above, we calculated a PGA score based on multiple genomic abnormalities in plasma as a potential classifier for association with treatment response and survival [20]. To evaluate a similar UGA based classifier, we modified the previously reported PGA score algorithm and created UGA scores. The UGA score was calculated using the sum of absolute log 2 ratios of the top ten abnormal genomic segments. Both inter and intra patient UGA score variations (for the 14 paired specimens) were observed (FIG. 16). UGA scores in pre-treatment group were higher in patients with high volume disease than low volume disease although it did not reach statistical significance (p=0.16) (FIG. 17).

To see whether genomic abnormality change between treatment points predicted clinical outcomes, we calculated urine TEff index by comparing percent differences between pre and post-treatment UGA scores for the patients with the paired samples. Kaplan-Meier survival analysis showed that a higher TEff index was significantly associated with better survival (p≤0.04) in CRPC cohort (FIGS. 18A and 18B). Five of seven CRPC patients with a decrease in the post chemotherapy UGA score were alive during the follow-up time while the two patients' whose UGA score increased died (Table 5U). For HSPC sub cohort, the UGA based TEff index also showed a clear trend association of higher TEff index with a longer progression time to castration resistance (FIG. 18C).

7. Treatment-Associated Genomic Abnormalities.

To examine treatment-associated genomic alterations, we generated log 2 ratios between pre- and post-treatment specimens directly from scaled read counts at each genomic window and performed segmentation analysis for treatment-related genomic gain or loss. Compared to pre-treatment, we observed a total of 34 genomic loci with copy number changes in the post treatment specimen. By defining minimal overlap regions at each locus, we identified commonly shared regions that covered nine genes (ZNRF3, RNF43, LGR4, NCOR1, ZBTB16, MYC, FGFR1, KRAS and STK11) (FIG. 19 and Table 6U). For example, after treatment, genomic region covering LGR4 was amplified in two cases of HSPC (#1080 and #1104), and genomic region covering ZBTB16 was deleted in two cases of CRPC (#1014 and #1060). The copy number changes in remaining seven gene regions were found in both advanced HSPC and CRPC urine specimens.

B. Summary.

The examination of tumor components including circulating tumor cells (CTC) and cfDNAs in body fluids referred to as a liquid biopsy [15, 18, 19] offers a non-invasive alternative to sampling metastatic site biopsy in determining prognostic or predictive molecular biomarkers. Successful development of a liquid biopsy program or this clinical application can limit risk from invasive biopsies in advanced cancer stages, which can also be challenging to perform. Additionally the ability to capture tumor associated genomic profiles in circulatory fluids also has the practical advantage of being performed on multiple time points with ease and the potential for offering molecular biomarker profiling in solid tumors in a more dynamic manner during treatments or during expectant monitoring [30]. For CRPC, liquid biopsy profiling is limited to enumeration of CTC, an FDA-approved test for assessing prognosis in metastatic castrate resistant stage. Due to technical limitation, high cost and because metastatic CRPC patients are known to have variable measurable CTC counts, a universal adoption of the CTC count for prognostication has not occurred in clinical practice. Furthermore, genomic characterization of CTCs is technically challenging and has not yet been reproducible for clinical use [31]. With advances in high throughput sequencing technology, sensitive detection of tumor-associated cfDNAs in body fluids has become feasible to perform for applying in practice if detected to have clinical utility [32].

cfDNA in blood has been extensively reported and proposed as biomarkers for cancer diagnosis, prognosis and treatment efficacy estimation. It is known that a small amount of cfDNA in blood passes after renal filtration into urine and tumor specific sequences are detectable in cfDNA isolated from urine [33, 34]. However a systematic determination of somatic genomic abnormalities in urine cfDNAs evaluated by high throughput sequencing technology [15, 19, 35] in prostate cancer has not been performed. Several challenges have limited this determination including a lack of precise knowledge on factors that may impact levels of urine cfDNA being measured as the concentration of urine cfDNA stability and fragment size is not as reliable as in blood. In previous reports urine cfDNA profiling using PCR-based detection of candidate tumor-associated genes indicates that, an optimized and uniform method for cfDNA detection in urine that prevents degradation during extraction and storage [36, 37] should also include adequate volumes of specimens. Likely factors influencing cfDNA detection in urine may include processing time of the urine samples after patient donation; the use of preservatives while processing; the time of the urine samples in room temperature before storage in −80° C., and urine volumes. We used a set of specimens collected using a rigorous and uniform sample processing protocol in 15 ml of urine and were able to detect cfDNA concentration in most samples. Another variable that can impact yield and quality is the type of kit used for cfDNA extraction. In this study we evaluated three commercial kits to identify any association of extraction kit with cfDNA quality and yield. Although cfDNA yield using the Analytik kit were the highest, purity of the cfDNAs remained a concern since we were not able to make high quality sequencing library using direct eluent from the kit. The Zymo kit generated relatively low yield but high quality sequencing libraries were consistently observed even at extremely low input of 0.25 ng. This suggests that selection of cfDNA extraction kit and thorough examination of cfDNA quality are variables that should be considered for ensuring the success of sequencing library preparation and subsequent data analysis.

We were able to detect urine CNVs in the patient samples with adequate cfDNA quality and quantity, although the extent of detectable CNV per sample was stage dependent with higher CNVs observed for CRPC patients than in HSPC stage. CNVs were also associated with volume of disease regardless of cancer stage, with a lower level of CNVs observed with low volume disease compared to high volume disease. Upon comparison of urine to plasma CNVs in the matched urine samples a lower incidence of detectable CNVs in urine specimens were generally observed (FIG. 14). This indicates an effect of renal filtration on urine cfDNA content and is in concordance with previous reports in other tumor types [33, 34], suggesting that a smaller fraction of blood cfDNA is detectable in urine. However, the lower urine CNV content did not impact the ability to detect somatic genomic changes similar to plasma in the matched urine specimens. For example, shared specific genomic aberrations were observed in both plasma and urine cfDNAs at loci of PTEN, TMPRSS2 and AR (FIG. 14). These results suggest that both urine and plasma fractions can be used for developing liquid biopsy based biomarkers in advanced prostate cancer.

For identifying predictive biomarkers using urine cfDNA, we examined CNV changes between pre and post treatment, and identified treatment-associated CNV changes at nine gene loci, the majority of which have been reported to play a role in prostate cancer genomics. We were able to detect copy number changes after treatment in RNF43 and ZNRF3 loci. These two closely related single membrane spanning molecules has revealed the receptor-like functionalities of a ligand-binding ectodomain. Combined with the intracellular architecture and activity of an E3 ligase, the two genes may be implicated in the modulation of Wnt signaling [38]. Post treatment copy number changes were also detectable in LGR4 and MYC proto oncogene loci. LGR4 has been reported to function in mammary gland development and mammary stem cells by activating Sox2 via the Wnt/β-catenin/Lef1 signaling pathway [39] and MYC proto-oncogene is frequently deregulated in prostate cancers, activating genetic programs that orchestrate biological processes to promote growth and proliferation [40]. The ability to detect cfDNA and the tumor specific genomic aberrations strongly suggests that a urine based liquid biopsy in advanced stage prostate cancer is feasible and could be developed further for determining predictive and prognostic classifiers.

The feasibility approach adopted in our study for developing such classifiers is agnostic of specific gene/region changes and uses an algorithmic summation of the most common genetic abnormalities in urine. Since the mutational landscape of advanced prostate cancer is heterogeneous [41] this approach is likely to account for multiple genomic changes in tumor biology as a result of treatment effect. With this data set, we observed an association of the changes in CNVs with survival after treatments for both HSPC and CRPC stages (FIG. 18).

In conclusion, urine cfDNA based genomic abnormality tests provide a measurable classifier that is contemplated for use to assess treatment response and clinical outcomes in advanced prostate cancer patients. Thus, urine cfDNA analysis based on whole-genome sequencing is contemplated as a liquid biopsy tool which is contemplated as a noninvasive biomarker to monitor response to therapy and predict clinical outcomes in future.

C. Materials and Methods.

The following are exemplary materials and methods used during the development of the present inventions.

1. Patient Methods.

Urine specimens were obtained from advanced prostate cancer patients in metastatic hormone sensitive and metastatic castrate resistant stages. Patients were enrolled in a prospectively collected, institutional review board (IRB) approved study at a tertiary hospital while undergoing stage specific standard of care treatments. Informed consent was obtained from these patients enrolled in the registry. The primary purpose of the registry is for developing blood and urine based classifiers of disease and treatment outcomes in this patient population while patients receive standard of care treatments. Twenty cases (ten hormone sensitive and ten castrate resistant stage patients) were selected for this study with each patient having two serial urine samples. Each patient provided the first of the two urine specimens before initiating stage specific treatment and a second specimen after starting treatments. Cases selected for this study had matched plasma cfDNA sequencing performed previously [20]. Urine specimens were collected at the same time as the plasma collections. Initial processing of urine specimens was performed uniformly within 45 minutes of receiving the sample from the patient. An initial centrifugation at 600 g for 10 minutes was followed by storage of the urine and pellet in −80° C. No urine specimen underwent any freeze-thaw cycles other than at the time of extraction of cfDNA. Peripheral blood mononuclear cell-derived germline DNA (gDNA) was collected at the same time as the plasma and urine specimens. Clinical outcomes of patients undergoing this prospective specimen banking was performed retrospectively as previously described [20].

2. Isolation of Cell Free DNA (cfDNA).

To determine the best urine cfDNA extraction kit, we tested three different commercial products using a single urine sample. The kits included Extract-all Urine DNA kit (Zymo research corp., Calif., USA), Urine DNA isolation kit (Norgen Biotek Corp., Ontario, Canada), and PME free-circulating DNA Extraction kit (Analytik Jena Innuscreen GmbH, Berlin, Germany). After thawing the urine sample, it was placed on ice immediately and then centrifuging of 15 ml urine was performed at 3000 rpm for 15 minutes. The supernatant was used for DNA extraction according to each manufacturers' protocol. cfDNA was eluted in 30 ul elution buffer and concentration was measured using Qubit Fluorometer (Life Technology, Carlsbad, Calif.).

3. DNA Extraction and Sequencing Library Preparation.

After an initial evaluation of the yield and quality of cfDNA from the three commercial kits, the Zymo research urine DNA Kit (Zymo Research, Irvine, Calif.) was selected to extract cfDNAs from 15 ml according to the manufacturer's instructions. The extracted DNA was eluted in 10 ul water. 1 ul DNA eluent was quantified using Qubit. The remaining was stored at −80° C. until use. For each patient germline DNA (gDNA) was also extracted and quantified. Sequencing DNA libraries were prepared for the urine cfDNA using a ThruPLEX DNA-Seq Kit (Rubicon Genomics, Inc. Ann Arbor, Mich.). 24 indexed libraries were pooled for single-read sequencing on a HiSeq2000 Sequencing System (Illumina, San Diego, Calif.).

4. Copy Number Variation (CNV) Calculation.

Raw sequencing data (fastq files) were first mapped to the human genome (hg19) (DNASTAR, Madison, Wis.). Read counts from the mapped sequence files were then binned into 60 kb windows (total 51672 genomic bins) and adjusted to the global mean count for each sample. The read count ratio in each genomic bin was calculated by dividing cfDNA with peripheral blood mononuclear cell germline DNA (gDNA) in the same patient [20]. The resulting ratios were further transformed with log 2 and corrected for GC content [42]. The fully normalized log 2 ratios in genomic bins were subjected to segmentation using the copy number analysis method (CNAM) algorithm (Golden Helix, Bozeman, Mont.).

5. Urine Genome Abnormality (UGA) Score Algorithm Calculation and Comparison with Plasma Genome Abnormality Score (PGA).

To quantify genomic abnormality, we improvised the previously reported methodology for calculating global genomic abnormalities in plasma by calculating a plasma genome abnormality (PGA) score [20]. This was performed by summing the most significant log 2 ratios in top 95-99% genomic bins. For the current study, we modified the genome abnormality calculation by summing log 2 ratios of ten most significant genomic segments, The 10 genes used in this exemplary analysis are: AR, MYC, CHD1, PTEN, RB1, TP53, ZBTB16, CCND1, PIK3CA/B and TMPRSS2-ERG.

We removed genomic regions containing centromeres and their surrounding +/−1 Mb. We also excluded genomic segments that were 4 bin windows (4×60 kb). From the remaining segments, we summed the top ten most significant segment values (using absolute numbers) and defined the summarized number as Urine Genomic abnormality (UGA) score. We reanalyzed the previously reported PGA score [43] in the same manner as the UGA score for consistency and comparability. A higher score is indicative of a greater tumor DNA fraction in the cfDNA. To quantify a treatment response index in each patient, we defined the TEff (Treatment Efficacy) index as the log 2 ratio of UGA (or PGA) scores between the pre- and post-treatments: TEff index=log 2 (preP GA/postP GA)×100.

6. Statistical Analysis.

For defining hormone sensitive and castrate resistant stage in this hospital-based registry a uniform definition was used as reported previously [20, 44]. Briefly, for the CRPC cohort, overall survival was recorded from the date of first plasma collection after ADT failure to death or last follow-up. For the HSPC cohort, disease progression was recorded from the date of first plasma collection at initiation of ADT to disease progression or last follow-up. To evaluate association of the UGA score with overall survival in the CRPC sub-cohort, time from developing castrate resistance to death was considered and Kaplan-Meier analysis was performed for the UGA score and TEff index associations with overall survival (prognostic classifier). For the HSPC cohort time from initiating androgen deprivation therapy (ADT) for hormone sensitive stage to development of castrate resistance was obtained (predictive classifier). We dichotomized each sub cohort into two risk groups using median UGA score or TEff index as a cut-off. A P-value of ≤0.05 was considered statistically significant for statistical analysis.

Example III

This example describes an algorithmic approach for determining the Plasma genome abnormality (23-PGA) and the Urine genome abnormality (23-UGA) scores based on cfDNA copy number variations in plasma and urine: 23 gene set.

As described herein, the inventors demonstrate that genomic changes such as copy number variations, mutations, fusions, etc., attributable to prostate tumor-derived DNA are found in the cell free DNAs (cfDNA) fraction of plasma and urine in advanced stages of prostate cancer. Genomic variations in cfDNA found in plasma and urine were measured that are ascribable to tumors.

Based on these measurements, a composite scoring algorithm, called Plasma Genomic Abnormality (PGA) and Urine Genomic Abnormality (UGA) was developed as described herein in section II, using a set of 10 genes. Data shown herein demonstrates that 10-PGA/10-UGA scores are associated with tumor burden and clinical outcomes in advanced prostate cancer patients. Therefore, variations in copy numbers of these 10 specific genes are the underlying basis for development of a predictive algorithm for clinical application.

A. 23-Gene Analysis.

For development of this method, in one embodiment, the following 23 gene set is used for measuring 23-UGA and 23-PGA scores. These genes were discovered associated with prostate cancer progression by 1) genomic (wide) sequencing and analyzing these results from cell free DNA collected in plasma and urine from a set of advanced prostate cancer patients as described in section II, then choosing a set of genes whose genome wide copy number variations are attributable to prostate cancer, for example, genetic areas of significant genomic aberrations at specific genomic loci that contain genes for prostate cancer development and progression that are found in both urine and plasma, and by 2) choosing certain genes that are implicated in prostate cancer biology. These 23-UGA and 23-PGA scores are derived from the data analyzed after performing whole genome sequencing and copy number analysis and then summing the total of the most significant genomic changes across the entire genome.

Based on the analysis of copy number variations observed in the data set obtained during the development of the present inventions and genes implicated in prostate cancer biology we have refined the gene list as below:
AR, PTEN, RB1, TNPRESS2, MYCL1, MYC, NOTCH1, TP53, ETSFusions, FOXA1, NKX3.1, ZBTB16, NCOR1, NCOR2, COL22A1, PIK3CA, PIK3B, PIK3R1, BRAF, RAF1, SPOP, APOB and SOX2.

For prediction of treatment outcomes based on copy number variations in the above genes in the advanced prostate cancer setting, we will employ the partial Cox regression method to develop a progression free survival (PFS) prediction model to the baseline (pre-treatment) sample of CNVs and then separately also to a second serial measurement to introduce covariance modeling for predicting clinical outcomes of treatments.

For the predictive model with two-time measures, the risk score (RS) in this predictive algorithm will be calculated as where G represents the number of candidate genes, bj represents the estimated coefficient of the jth gene, Xij represents baseline (i.e., pre-ADT) absolute log ratios (ALR) of the jth gene in sample i, Dij is the differences in ALR of gene j between pre-treatment and post-treatment initiation in sample I, and b*j represents the estimated coefficient of Dj.

B. Validation of Predictive Model.

The algorithm derived from the partial Cox regression is contemplated for use to calculate the risk score for each patient in the validation set. This risk score is then contemplated to be associated with PFS using the Cox regression model. Thus, in one embodiment, each patient will be classified into high- or low-risk groups according to the risk score calculated as described herein. In one embodiment, the difference in PFS between risk groups will be assessed and contemplated for use with the log-rank test. In one embodiment, a time-dependent AUC-ROC will be used to test the time frame where the use of this risk score will increase predictive accuracy in the presence of other clinical variables, such as with other copy number variation methods described herein, PSA scores, clinical evaluations, other diagnostic tests, and the like.

Example IV

Exemplary statistical analysis for Leave-one-out cross validation (LOOCV).

Cross-validation, sometimes called rotation estimation, refers to a model validation technique for assessing how the results of a statistical analysis will generalize to an independent data set. It is mainly used in settings where the goal is prediction, and one wants to estimate how accurately a predictive model will perform in practice. Leave-p-out cross-validation (LpO CV) involves using p observations as the validation set and the remaining observations as the training set. This is repeated on all ways to cut the original sample on a validation set of p observations and a training set. Leave-one-out cross-validation (LOOCV) refers to a particular case of leave-p-out cross-validation with p=1. LOOCV is applicable to small sample sizes having high dimensional data (such as one sample containing a large number of genes).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, oncology, molecular biology, cell biology, genetics, statistics or related fields are intended to be within the scope of the following claims.

The invention claimed is:

1. A method, comprising:
   i) isolating a first cell free (cf) DNA plasma sample from a prostate cancer patient prior to treatment with Androgen Deprivation Therapy (ADT);
   ii) sequencing genomic cfDNA from said first cfDNA plasma sample so as to determine a first copy number variation as compared to a control;
   iii) calculating a first cfDNA Plasma Genomic Abnormality (PGA) Score based on said copy number variation;
   iv) treating said prostate cancer patient with said ADT;
   v) isolating a second genomic cell free cfDNA sample from said prostate cancer patient after said treating of step (iv);
   vi) sequencing said second genomic cfDNA so as to determine a second copy number variation as compared to a control;
   vii) calculating a second cfDNA PGA Score based on said second copy number variation;
   viii) comparing said first PGA score with said second PGA score; and
   ix) administering a second type of treatment to said patient when said second cfDNA PGA Score is equal to or greater than said first cfDNA PGA Score.

2. The method of claim 1, wherein said second cfDNA PGA Score is obtained at least two weeks after initiating Androgen Deprivation Therapy.

3. The method of claim 1, wherein said second cfDNA PGA Score is obtained at least two months after initiating Androgen Deprivation Therapy.

4. The method of claim 1, wherein said control comprises genomic DNA from said patient's lymphocytes.

5. The method of claim 1, wherein said patient shows symptoms of Androgen Deprivation Therapy failure after step iv).

6. The method of claim 5, wherein said symptoms appear before step v).

7. The method of claim 1, wherein said second copy number variation is calculated from a IS-gene panel.

8. The method of claim 7, wherein said IS-genes are ZDHHCI8, MRPS22, SAMD7, DMTN, ZNF704, SPAG I, SNX3I, SAMDI2, LOCIOI928I97, KLHDC4, SPG7, CHMPIA, PDRG 1, PETN and RB 1.

9. The method of claim 1, wherein said second type of treatment is a chemotherapy composition.

10. The method of claim 1, wherein said second type of treatment is selected from the group consisting of hormonal therapy and radiotherapy.

* * * * *